United States Patent
Van Dijk et al.

(10) Patent No.: US 11,236,346 B2
(45) Date of Patent: Feb. 1, 2022

(54) DIPLOSPORY GENE

(71) Applicant: Keygene N.V., Wageningen (NL)

(72) Inventors: Peter Johannes Van Dijk, Wageningen (NL); Diana Rigola, Wageningen (NL); Marinus Willem Prins, Wageningen (NL); Adrianus Johannes Van Tunen, Wageningen (NL)

(73) Assignee: KEYGENE N.V., Wageningen (NL)

( * ) Notice: Subject to any disclaimer, the term of this patent is extended or adjusted under 35 U.S.C. 154(b) by 24 days.

(21) Appl. No.: 15/757,020

(22) PCT Filed: Sep. 5, 2016

(86) PCT No.: PCT/NL2016/050617
§ 371 (c)(1),
(2) Date: Mar. 2, 2018

(87) PCT Pub. No.: WO2017/039452
PCT Pub. Date: Mar. 9, 2017

(65) Prior Publication Data
US 2018/0216122 A1 Aug. 2, 2018

(30) Foreign Application Priority Data
Sep. 4, 2015 (NL) .................................... 2015398

(51) Int. Cl.
| C12N 15/82 | (2006.01) |
| C12Q 1/68 | (2018.01) |
| C12Q 1/6895 | (2018.01) |
| C12N 15/113 | (2010.01) |
| C12N 15/62 | (2006.01) |

(52) U.S. Cl.
CPC ........ *C12N 15/8201* (2013.01); *C12N 15/113* (2013.01); *C12N 15/625* (2013.01); *C12N 15/8202* (2013.01); *C12N 15/8223* (2013.01); *C12N 15/8287* (2013.01); *C12Q 1/68* (2013.01); *C12Q 1/6895* (2013.01); *C12Q 2525/207* (2013.01); *C12Q 2600/13* (2013.01)

(58) Field of Classification Search
CPC .................................................. C12N 15/8201
See application file for complete search history.

(56) References Cited

U.S. PATENT DOCUMENTS

| 2004/0148667 A1 | 7/2004 | Savidan et al. |
| 2004/0168216 A1 | 8/2004 | Carman |
| 2005/0155111 A1 | 7/2005 | Carman |
| 2006/0179498 A1 | 8/2006 | Dirks et al. |

FOREIGN PATENT DOCUMENTS

| CN | 104145805 A | 11/2014 |
| FR | 2759708 A1 | 8/1998 |
| WO | WO-97/10704 A1 | 3/1997 |
| WO | WO-2007/066214 A2 | 6/2007 |
| WO | WO-2011/055352 A1 | 5/2011 |

OTHER PUBLICATIONS

Bowie et al, (1990, "Deciphering the Message in Protein Sequences: Tolerance to Amino Acid Substitutions", Science 247:1306-1310).*
McConnell et al, (2001, "Radial Patterning of *Arabidopsis* Shoots By Class III HD-ZIP and KANADI Genes", Nature 411 (6838):709-713).*
Kano-Murakami et al (1993, "A Rice Homeotic Gene, OSH1, Causes Unusual Phenotypes in Transgenic Tobacco", FEBS 334:365-368).*
Matvienko et al (2011, NCBI Accession No. JI57399 7.1).*
Matvienko et al., (2011, NCBI Accession No. JI573997). (Year: 2011).*
Asker, "Progress in apomixes research", Hereditas, 1979, vol. 91, pp. 231-240.
Barrell et al., "Confocal microscopy of whole ovules for analysis of reproductive development: the elongate1 mutant affects meiosis II", The Plant Journal, 2005, vol. 43 pp. 309-320.
Bicknell et al., "Understanding apomixes: recent advances and remaining conundrums", The Plant Cell, Supplement 2004, vol. 16, pp. S228-S245.
Daniell, "Molecular strategies for gene containment in transgenic crops", Nat Biotechnol., 2002, vol. 20, No. 6, pp. 581-586.
Hermsen, "Breeding for apomixes in potato: pursuing a utopian scheme", Euphytica, 1980, vol. 29, pp. 595-607.
Morgan et al., "Seed set in an apomictic BC3 pearl millet", International Journal of Plant Sciences, 1998, vol. 159, No. 1, pp. 89-97.
Savidan, "Chapter 11: Transfer of Apomixis through wide crosses", The Flowering of Apomixis: From mechanisms to Genetic Engineering, 2001, pp. 153-167.
Vielle Calzada et al., "Apomixis: the asexual revolution", Science, Nov. 1996, vol. 274, pp. 1322-1323.
Catanach et al., "Deletion mapping of genetic regions associated with apomixis in Hieracium", PNAS, Dec. 2006, vol. 103, No. 49, pp. 18650-18655.
Khan et al., "Apomixis: The molecular perspectives and its utilization in crop breeding", Sep. 2015, retrieved from the Internet: URL:https://www.researchgate.net/profile/Anil_Singh23/publication/281490766_Apomixis_The_Molecular_Perspectives_and_its_Utilization_in_Crop_Breeding/links/55eab6e608ae65b6389c620a.pdf?origin=publication_detail.

(Continued)

*Primary Examiner* — Russell Kallis
(74) *Attorney, Agent, or Firm* — Foley & Lardner LLP; Sunit Talapatra

(57) ABSTRACT

The invention provides nucleotide sequences and amino acid sequences of the Dipgene as well as (functional) homologues, fragments and variants thereof, which provides diplospory as a part of apomixis. Also diplospory plants and methods for making these are provided, as are methods of using these, and methods of making apomictic seed.

11 Claims, 3 Drawing Sheets

Specification includes a Sequence Listing.

(56) References Cited

OTHER PUBLICATIONS

Ramulu et al., "Apomixis for crop improvement", Protoplasma, 1999, vol. 208, pp. 196-205.
Van Dijk et al., "An apomixes-gene's view on dandelions" In: "Lost Sex", 2009, pp. 475-493.
Vijverberg et al., "Chapter VIII genetic linkage mapping of apomixes loci", 2007, retrieved from the Internet: URL:https://pure.knaw.nl/portal/files/475814/Vijverberg_ea_3828.pdf, retrieved Nov. 17, 2016.
Vijverberg et al., "Genetic fine-mapping of Diplosporous in *Taraxacum* (dandelion; Asteraceae) indicates a duplicated DIP-gene", BMC Plant Biology, 2010, vol. 10, pp. 154 (17 pages).
International Search Report issued in International Patent Application No. PCT/NL2016/050617, dated Nov. 30, 2016.
Tas, et al. "Crosses between sexual and apomictic dandelions (*Taraxacum*). I. The inheritance of apomixis"; Heredity 83 (1999); pp. 707-714.
Van Dijk, et al. "Crosses between sexual and apomictic dandelions (*Taraxacum*). II. The inheritance of apomixis"; Heredity 83 (1999); pp. 715-721.
Van Baarlen, et al. "Comparative cyto-embryological investigations of sexual and apomictic dandelions (*Taraxacum*) and their apomictic hybrids"; Sex Plant Reprod 15 (2002); pp. 31-38.
Van Dijk, et al. "Formation of Unreduced Megaspores (Diplospory) in Apomictic Dandelions (*Tarazacum officinale*, s.l.) Is Controlled by a Sex-Specific Dominant Locus"; Genetics (Jan. 2004); 166: 483-492.
Vijverberg, et al. A genetic linkage map of the diplosporous chromosomal region in *Taraxacum officinale* (common dandelion; Asteraceae); Theor Appl Genet (2004) 108: 725-732.
Vasut, et al. "Fluorescent in situ hybridization shows Diplosporous located on one of the NOR chromosomes in apomictic dandelions (*Taraxacum*) in the absence of a large hemizygous chromosomal region"; Genome, 2014, 57(11/12): 609-620, https://doi.org/10.1139/gen-2014-0143.

* cited by examiner

Figure 2

```
DIP    1  GAAACCGAAGCAAACTCTACCACATCCGCCTCCGGGTCCGCCTCCCGAGACCGCTAACCC   60
          ||||||||||||||||||||||||||||||||||||||||||||| ||||||||||||||
dip    1  GAAACCGAAGCAAACTCTACCACATCCGCCTCCGGGTCCGCCTCCCAAGACCGCTAACCC   60

DIP   61  CCAACCAC####CCGTTAAAACCCTACTCGTGGGACCAAGCAGTCGGCCTCTCCGTCCTCA  120
          ||||||||    ||||||||||||||||||||||||||||||||||||||||||||||||
dip   61  CCAACCAC####CCGTTAAAACCCTACTCGTGGGACCAAGCAGTCGGCCTCTCCGTCCTCA  117

DIP  121  CCA####ATTCCAATTCCGATTCCGACCTCAAAGACGAAACCCTCGTCCTCTCCAAAT    180
          |||    ||||||||||||||||||||||||||||||||||||||||||||||||||
dip  118  CCA####ATTCCAATTCCGATTCCGACCTCAAAGACGAAACCCTCGTCCTCTCCAAAT    171

DIP  181  CCCTCAAACAAAAGGGCAAATTCGTCATTATCACCCAACGGTTACTCCTCATTGTTACCT  240
          |||||||||||||||||||||||||||||||||||||||||||||||||||||||||||
dip  172  CCCTCAAACAAAAGGGCAAATTCGTCATTATCACCCAACGGTTACTCCTCATTGTTACCT  231

DIP  241  CCTCGAGCCTAACGAATTTAGGTCAACCC#ATTTCAAAGGCGTCCCTGCGGACCCCGATT  300
          ||||||||||||||||||||||||||||| ||||||||||||||||||||||||||||||
dip  232  CCTCGAGCCTAACGAATTTAGGTCAACCC#ATTTCAAAGGCGTCCCTGCGGACCCCGATT  291

DIP  301  CGGTGGTTGAAGCCGAGATAACGTTGGATAGTGTGATACACGTGGATGTTGATGGAGAGC  360
          |||||||||||||||||||||||||||||||||||||||||||||||||||||||||||
dip  292  CGGTGGTTGAAGCCGAGATAACGTTGGATAGTGTGATACACGTGGATGTTGATGGAGAGG  351

DIP  361  TGGTGCATATTGTCGGGAGTAGTTCTGATGTGGTGGTTAGACAGAATGTTGGT######   413
          |||||||||||||||||||||||||||||||||||||||||||||||||||||
dip  352  TGGTGCATATTGTCGGGAGTAGTTCTGATGTGGTGGTTAGACAGAATGTTGGT######   411

DIP  414  ######GGGAAGCAGCGGTGGTATAAT######CCGTTGCCGCTGTTTCAGACGA      456
                |||||||||||||||||||||     ||||||||||||||||||||||
dip  412  ######GGGAAGCAGCGGTGGTATAAT######CCGTTGCCGCTGTTTCAGACGA      471

DIP  457  ATTTGGAGTGTTTAGGGAAGGAGGAGGCGGGGGAGTTGTTGAAGGTGTTGTTGGTGACGA  516
          ||||||||||||||||||||||||||||||||||||||||||||||||||||||||||||
dip  472  ATTTGGAGTGTTTAGGGAAGGAGGAGGCGGGGGAGTTGTTGAAGGTGTTGTTGGTGACGA  531

DIP  517  TTGAGAGAGGGAAGGAGAGAGGGTGGGGCCGGGGGTGTGTGTACCGTCTGCATCAGAGTA  576
          || |||||||||||||||||||||||||||||||||||||||||||||||||||||||||
dip  532  TTCAGAGAGGCAAGGAGAGAGGGTGGGGCCGCGGGTGTGTGTACCGTCTGCATCAGAGTA  591

DIP  577  ATGTTAGGTGATGTATA.........CTACATATAAAG-TTACTATAGGAGAAAAGGACT  635
          ||||||||||||||||         |||||||||||| ||||||||||||||||||||||
dip  592  ATGTTAGGTGATGTATATTTTTTTT#TACATATAAAGTTACTATAGGAGAAAAGGACT    651

DIP  636  GGATATTATATTATACATACCTG-AAACAAGGAAACGTTTTCTTTCAAAATTTTGGCTGT  694
          |||||||||||||||||||||| |||||||||||||||||||||||||||||||||||
dip  652  GGATATTATATTATACATACCTGAAAACAAGGAAACGTTTTCTTTCAAAATTTTGGCTGT  711

DIP  695  ATTATTATTTGTCGACCATGTTGGGCTAAAATGGCCAATTATTTACTTATGACATGGTT   754
          ||||||||||||||||||||||||||||||||||||||||||||||||||||||||||
dip  712  ATTATTATTTGTCGACCATGTTGGGCTAAAATGGCCAATTATTTACTTATGACATGGTT   771

DIP  755  AAAAAATATTGGTGTCTTGTTTTGTATAATTACAATTTATATT######AGTATCG-   804
          |||||||||||||||||||||||||||||||||||||||||||     | |||
dip  772  AAAAAATATTGGTGTCTTGTTTTGTATAATTACAATTTATATT######ACTATAAC   831

DIP  805  --ATGCAATGTAAGATTGTAGAAAGCGCTACCGTATAAAACAACATAAGTCATGAGGTTA  862
            |||||||||||||||| || |  |  | |  |  ||||||||||||||||| ||
dip  832  TTATGCAATGTAAGATTGTGTATAAAACAACATAAGTCATGAGGTTACACCCTAGTGGGA  891

DIP  863  CACCCTAGTGGGGTCAAGGGAACAAAAACATTTTAAACGTTTTCAG           909
          |      |   |||||||||||||||||||||||||||||||||||
dip  879  TCAAGGGGCTACACCCCGGAACAAAAACATTTTAAACGTTTTCAG             938
```

DIPLOSPORY GENE

CROSS-REFERENCE TO RELATED APPLICATIONS

This application is the National Phase of International Patent Application No. PCT/NL2016/050617, filed Sep. 5, 2016, published on Mar. 9, 2017 as WO 2017/039452 A1, which claims priority to Netherlands Patent Application No. 2015398, filed Sep. 4, 2015. The contents of these applications are herein incorporated by reference in their entirety.

SEQUENCE LISTING

The instant application contains a Sequence Listing which has been submitted in ASCII format via EFS-WEB and is hereby incorporated by reference in its entirety. Said ASCII copy, created on Sep. 27, 2018, is named 085342-2100 SL.txt and is 91,971 bytes.

FIELD OF THE INVENTION

The present invention relates to the field of biotechnology and in particular to plant biotechnology including asexual plant breeding. Particularly, the invention relates to the identification of genes, variants or fragments thereof as well as to the proteins and peptides they encode relating to the processes underlying apomixis, particularly gametophytic apomixis through diplospory. The invention also relates to methods using the genes, proteins, variants and fragments thereof of the invention for inducing gametophytic apomixis through diplospory in plants and crops, and methods for producing diplosporous plants and apomictic seeds.

BACKGROUND OF THE INVENTION

In botany, apomixis (also known as agamospermy) refers to the formation of seeds by asexual processes. Apomixis occurs via a series of developmental processes, which collectively convert the sexual developmental program of a plant to an asexual developmental program. Recurrent apomixis has been reported to occur in more than 400 flowering plant species (Bicknell and Koltunow 2004). Apomixis may occur in different forms including at least two forms known as gametophytic apomixis and sporophytic apomixis (also referred to as adventive embryony). Examples of plants where gametophytic apomixis occurs include dandelions (*Taraxacum* sp.), hawkweeds (*Hieracium* sp.), Kentucky blue grass (*Poa pratensis*), eastern gamagrass (*Tripsacum dactyloides*) and others. Examples of plants where sporophytic apomixis occurs include citrus (*Citrus* sp.), mangosteen (*Garcinia mangostana*), and others.

Interests in apomixis in general, but particularly in gametophytic apomixis, has increased over the last decades due to its potential usefulness in agriculture, particularly for the purpose of clonal seed production. Gametophytic apomixis is characterized by at least two developmental processes: (1) the avoidance of meiotic reduction (apomeiosis), and (2) development of the egg cell into an embryo, without fertilization (parthenogenesis). The seeds resulting from the process of gametophytic apomixis are referred to as apomictic seeds.

Since apomictic seeds are genetically identical to the maternal parent plant, they are considered to be a clone of the maternal parent plant and therefore the process that produces such seeds is termed clonal seed production. It has been recognized since long that apomixis can be extremely useful in plant breeding (Asker 1979, Hermsen, J. G. Th. 1980. Breeding for apomixis in potato: Pursuing a utopian scheme. Euphytica 29:595-607, Asker and Jerling 1990, DeVielle Calzada et al. 1995). An advantage of apomixis is the ability to perform true breeding of heterotic F1 hybrids (i.e. indefinite multiplication of F1 hybrids of uniform genetic quality). In most crops, F1 hybrids are the best varieties because they are often associated with higher yields, a phenomenon often called 'heterosis'. Because self-fertilization of F1 hybrids causes loss of heterosis by recombination in the F2 sexual crops, F1 hybrids have to be produced each generation again by crossing of inbred homozygous parents. Producing sexual F1 seeds is a complicated and costly process, which needs to be repeated perpetually. In contrast, apomictic F1 hybrids are true breeding organisms, i.e. which are capable of breeding true.

Apomixis is of great interest in agriculture because it has the power to fix favourable genotype, regardless of its genetic complexity, and allows production of organisms that can breed true in one step. This implies that apomixis could be used for immediate fixation of polygenic quantitative traits of interest. It should be noted that most yield traits are polygenic. Apomixis could be used for the stacking (or pyramiding) of multiple traits (for example various resistances, several transgenes, or multiple quantitative trait loci). Without apomixis, in order to fix such suite of traits, each trait locus must be made homozygous individually and later on combined again into the hybrid. As the number of loci involved in a trait increases, generating homozygous trait loci by crossing is laborious, time-consuming and a logistical challenge. Similarly, selection of suitable parental lines for the F1 hybrid requires great investments in time and effort. Moreover specific epistatic interactions between alleles are lost in the homozygous (parental line) phase and may not return upon combination in the F1 hybrid. With apomixis, it becomes possible to fix this type of non-additive genetic variation.

Besides the instantaneously fixing of any genotype, whatever its complexity, there are important additional agricultural uses of apomixis. Sexual interspecific hybrids and autopolyploids often suffer from sterility due to meiotic problems. Since apomixis skips meiosis, these problems occurring in interspecific hybrids and autopolyploids would be solved. Since apomixis prevents female hybridization, apomixis coupled with male sterility has been proposed for the containment of transgenes, preventing transgene introgression in wild relatives of transgenic crops (Daniell, H. 2002. Molecular strategies for gene containment in transgenic crops. Nature biotechnology 20: 581-586). In insect-pollinated crops (e.g. *Brassica*), apomictic seed set would not be limited by insufficient pollinator services. This is becoming more important in the light of the increasing health problems of pollinating bee populations (*Varroa* mite infections, African killer bees etc.). As most viruses are not transmitted by seed, tuber propagated crops, like potato, apomixis could be exploited to maintain the superior genotype clonally, but remove the risk of virus transmission through tubers. Also the storage costs of apomictic seeds would be much lower than that of tubers. In ornamentals apomixis could replace labour intensive and expensive tissue culture propagation. It is well understood that in general apomixis strongly reduces the costs of cultivar development and propagation.

Apomixis does not occur in the major crops, most of which are sexual seed crops. There have been numerous attempts to introduce apomixis in sexual crops. Specifically, since apomixis in under genetic control, many have sought to identify genes involved in apomixis processes. Apomixis in natural apomicts have been investigated as a sources of apomixis genes (Ozias-Akins, P. and P. J. van Dijk. 2007 in: Annu. Rev. Genet. 41:509-537). However, the genetics and molecular background of apomixis still remains poorly understood and attempts at identifying apomixis genes have not produced genes suitable for use in agriculture so far. This is mainly due to the fact that identification and isolation of apomixis genes has proven to be a difficult task. Natural apomicts are often polyploids and positional cloning in polyploidy plants is difficult to perform. Other complicating factors are suppression of recombination in apomixis-specific chromosomal regions, repetitive sequences and segregation distortion in crosses. Further, the genomes of apomictic plants have not yet been sequenced, which complicates the search for apomixis genes overall. Hence, apomixis genes have not been cloned and/or isolated. Attempts to introduce apomixis in sexual crops can be summarized as follows:

a) Introgression of apomixis (apomictic) genes from wild apomictic plants into crop species through wide crosses have not been successful so far, e.g. attempts to transfer apomixis from *Tripsacum dactyloides* into maize and millet [Savidan, Y. (2001). Transfer of apomixis through wide crosses. In Flowering of Apomixis: From Mechanisms to Genetic Engineering, Y.; apomixis from *Pennisetum squamulatum* into pearl millet. Savidan, J. G. Carman, and T. Dresselhaus, eds (Mexico: CIMMYT, IRD, European Commission DG VI), pp. 153-167; Morgan, R., Ozias-Akins, P., and Hanna, W. W. (1998). Seed set in an apomictic BC3 pearl millet. Int. J. Plant Sci. 159, 89-97.; WO97/10704.]

b) Mutants of sexual model species, especially in *Arabidopsis*. For example, WO2007066214 describes the use of an apomeiosis mutant called Dyad in *Arabidopsis*. However, the Dyad is a recessive mutation with very low penetrance. The practical use of this mutant in a crop species this mutation would be of very limited practical use.

c) Generation of apomixis de novo by hybridization between two sexual ecotypes has not resulted in agronomically interesting apomicts (US20040168216 and US20050155111).

d) Cloning of candidate apomixis genes by transposon tagging in maize. US20040148667 discloses orthologs of the elongate gene, which were hypothesized to induce apomixis. However, according to Barrell and Grossniklaus (2005) in Plant Journal Vol: 34, pp 309-320, the elongate gene skips meiosis II and therefore does not maintain the maternal genotype.

Further, it has been described in US20060179498 that so-called 'reverse breeding' could serve as an alternative for apomixis. However, reverse breeding represents a complicated and laborious in vitro laboratory procedure compared to apomixis which does not require any laboratory procedures since it is an in vivo procedure that is carried out by the plant itself without any external (human) intervention. Moreover, with reverse breeding, once the parental lines have been reconstructed (doubled gamete homozygotes) crossing still has to be carried out.

Therefore there is a need for alternative procedures for inducing apomixis in sexual crops, which are devoid of at least some of the limitations of the present state of the art. Particularly, there is a need for methods for producing diplosporous plants and apomictic seeds. There is also a need to uncover alternative genes and proteins involved in the processes of apomixis, particularly diplospory, which are suitable for use in the methods above and which can substantially mimic the apomictic pathways in sexual crops.

SUMMARY OF THE INVENTION

The invention provides nucleotide sequences and amino acid sequences of the Dip gene as well as (functional) homologues, fragments and variants thereof, which provides diplospory as a part of apomixis. Also diplospory plants and methods for making these are provided, as are methods of using these, and methods of making apomictic seed.

DETAILED DESCRIPTION OF THE INVENTION

Definitions

The term 'sexual plant reproduction' as used herein refers to a developmental pathway where a diploid somatic cell referred to as the 'megaspore mother cell' undergoes meiosis to produce four reduced megaspores. One of these megaspores divides mitotically to form the megagametophyte (also known as the embryo sac), which contains a reduced egg cell (i.e. cell having a reduced number of chromosomes compared to the mother) and two reduced polar nuclei. Fertilization of the egg cell by one sperm cell of the pollen grain generates a diploid embryo, while fertilization of the two polar nuclei by the second sperm cell generates the triploid endosperm (process referred to as double fertilization).

The term 'megaspore mother cell' or 'megasporocyte' as used herein refers to a diploid cell that produces megaspores by reduction, usually meiosis, to create four haploid megaspores which will develop into female gametophytes. In angiosperms (also known as flowering plants), the megaspore mother cell produces a megaspore that develops into a megagametophyte through two distinct processes including megasporogenesis (formation of the megaspore in the nucellus, or megasporangium), and megagametogenesis (development of the megaspore into the megagametophyte).

The term 'asexual plant reproduction' as used herein is a process by which plant reproduction is achieved without fertilization and without the fusion of gametes. Asexual reproduction produces new individuals, genetically identical to the parent plants and to each other, except when mutations occur. Plants have two main types of asexual reproduction including vegetative reproduction (i.e. involves budding tillering, etc of a vegetative piece of the original plant) and apomixis.

The term 'apomixis' as used herein refers to the formation of seeds by asexual processes.

The term 'diplospory' as used herein refers to a situation where an unreduced embryo sac is derived from the megaspore mother cell either directly by mitotic division or by aborted meiotic events. Three major types of diplospory have been reported, named after the plants in which they occur, and they are the *Taraxacum*, Ixeris and Antennaria types. In the *Taraxacum* type, the meiotic prophase is initiated but then the process is aborted resulting in two unreduced dyads one of which gives rise to the embryo sac by mitotic division. In the Ixeris type, two further mitotic divisions of the nuclei to give rise to an eight-nucleate embryo sac follow equational division following meiotic prophase. The *Taraxacum* and Ixeris types are known as meiotic diplospory because they involve modifications of meiosis. By contrast, in the Antennaria type, referred to as mitotic diplospory, the megaspore mother cell does not initiate meiosis and directly divides three times to produce the unreduced embryo sac. In gametophytic apomixis by diplospory, an unreduced gametophyte is produced from an unreduced megaspore. This unreduced megaspore results from either a mitotic-like division (mitotic displory) or a modified meiosis (meiotic displory). In both gametophytic apomixis by apospory and gametophytic apomixis by diplospory, the unreduced egg cell develops parthenogenetically into an embryo. Apomixis in *Taraxacum* is of the diplosporous type, which means that the first female reduction division (meiosis I) is skipped, resulting in two unreduced megaspores with the same genotypes as the mother plant. One of these megaspores degenerates and the other surviving unreduced megaspore gives rise to the unreduced megagametophyte (or embryo sac), containing an unreduced egg cell. This unreduced egg cell develops without fertilization into an embryo with the same genotype as the mother plant. The seeds resulting from the process of gametophytic apomixis are referred to as apomictic seeds.

The term 'diplospory function' refers to the capability to induce diplospory in a plant, preferably in the female ovary, preferably in a megaspore mother cell and/or in a female gamete. Thus a plant in which diplospory function is introduced, is capable of performing the diplospory process, i.e. producing unreduced gametes via a meiosis I restitution.

The term 'diplospory as part of gametophytic apomixis' refers to the diplospory component of the process of apomixis, i.e. the role that diplospory plays in the formation of seeds by asexual processes. In particular, next to diplospory function, parthenogenesis function is required as well in establishing the process of apomixis. Thus, a combination of diplospory and parthenogenesis functions may result in apomixis.

Apomixis is known to occur in different forms including at least two forms known as gametophytic apomixis and sporophytic apomixis (also referred to as adventive embryony). Examples of plants where gametophytic apomixis occurs include dandelion (*Taraxacum* sp.), hawkweed (*Hieracium* sp.), Kentucky blue grass (*Poa pratensis*), eastern gamagrass (*Tripsacum dactyloides*) and others. Examples of plants where sporophytic apomixis occurs include *citrus* (*Citrus* sp.) mangosteen (*Garcinia mangostana*) and others.

The term 'diplosporous plant' as used herein refers to a plant, which undergoes gametophytic apomixis through diplospory or a plant that has been induced (e.g. by genetic modifications) to undergo gametophytic apomixis through diplospory. In both cases, diplosporous plants produce apomictic seeds when combined with an parthenogenesis factor.

The term 'apomictic seeds' as used herein refers to seeds, which are obtained from apomictic plant species or by plants or crops induced to undergo apomixis, particularly gametophytic apomixis through diplospory. Apomictic seeds are characterised in that they are a clone and genetically identical to the parent plant and germinate plants that are capable of true breeding.

A 'clone' of a cell, plant, plant part or seed is characterized in that they are genetically identical to their siblings as well as to the parent plant from which they are derived. Genomic DNA sequences of individual clones are nearly identical, however, mutations may cause minor differences.

The term 'true breeding' or 'true breeding organism' (also known as pure-bred organism) as used herein refers to an organism that always passes down a certain phenotypic trait unchanged or nearly unchanged to its offspring. An organism is referred to as true breeding for each trait to which this applies, and the term 'true breeding' is also used to describe individual genetic traits.

The term 'F1 hybrid' (or filial 1 hybrid) as used herein refers to the first filial generation of offspring of distinctly different parental types. F1 hybrids are used in genetics, and in selective breeding, where it may appear as F1 crossbreed. The offspring of distinctly different parental types produce a new, uniform phenotype with a combination of characteristics from the parents. 'F1 hybrids' are associated with distinct advantages such as heterosis, and thus are highly desired in agricultural practice. In an embodiment of the invention, the methods, genes, proteins, variants or fragments thereof as taught herein can be used to fix the genotype of F1 hybrids, regardless of its genetic complexity, and allows production of organisms that can breed true in one step.

The term 'allele(s)' as used herein refers to any of one or more alternative forms of a gene at a particular gene locus. In a diploid cell of an organism, alleles of a given gene are located at a specific location, or locus (loci plural) on a chromosome. One allele is present on each chromosome of the pair of homologous chromosomes. A diploid, or polyploid plant species may comprise a large number of different alleles at a particular locus. In an embodiment, the Dip locus of wild *Taraxacum* accessions as taught herein, may comprise various Dip or dip alleles, which may vary slightly in nucleotide and/or encoded amino acid sequence.

The term 'locus' (loci plural) as used herein refers to one or more specific locations or sites on a chromosome where, for example, one or more genes or genetic markers is/are located. For example, the "Dip locus" as taught herein refers to the position in the genome where the Dip gene (and two (or more) dip alleles) as taught herein is (are) found.

The term 'dominant allele' as used herein refers the relationship between alleles of one gene in which the effect on phenotype of one allele (i.e. the dominant allele) masks the contribution of a second allele (the recessive allele) at the same locus. The first allele is dominant and the second allele is recessive. For genes on an autosome (any chromosome other than a sex chromosome), the alleles and their associated traits are autosomal dominant or autosomal recessive. Dominance is a key concept in Mendelian inheritance and classical genetics. For example, a dominant allele may code for a functional protein whereas the recessive allele does not. In an embodiment, the genes and fragments or variants thereof as taught herein refer to dominant alleles of the Dip gene.

The term 'female ovary' (plural form is 'ovaries') as used herein refers to an enclosure in which spores are formed. It can be composed of a single cell or can be multicellular. All plants, fungi, and many other lineages form ovaries at some point in their life cycle. Ovaries can produce spores by mitosis or meiosis. Generally, within each ovary, meiosis of a megaspore mother cell produces four haploid megaspores. In gymnosperms and angiosperms, only one of these four megaspores is functional at maturity, and the other three degenerate. The megaspore that remains divides mitotically and develops into the female gametophyte (megagametophyte), which eventually produces one egg cell.

The term 'female gamete' as used herein refers to a cell that fuses with another ('male') cell during fertilization (conception) in organisms that sexually reproduce. In species that produce two morphologically distinct types of gametes, and in which each individual produces only one type, a female is any individual that produces the larger type of gamete (called an ovule (ovum) or egg). In plants, the female ovule is produced by the ovary of the flower. When mature, the haploid ovule produces the female gamete which is then ready for fertilization. The male cell is (mostly) haploid) pollen and is produced by the anther.

The term 'pollination' or 'pollinating' as used herein refers to the process by which pollen is transferred from the anther (male part) to the stigma (female part) of the plant, thereby enabling fertilization and reproduction. It is unique to the angiosperms, the flower-bearing plants. Each pollen grain is a male haploid gametophyte, adapted to being transported to the female gametophyte, where it can effect fertilization by producing the male gamete (or gametes), in the process of double fertilization. A successful angiosperm pollen grain (gametophyte) containing the male gametes is transported to the stigma, where it germinates and its pollen tube grows down the style to the ovary. Its two gametes travel down the tube to where the gametophyte(s) containing the female gametes are held within the carpel. One nucleus fuses with the polar nuclei to produce the endosperm tissues, and the other with the ovule to produce the embryo. Even most natural apomicts need pollination for the sexual development of the endosperm. However in a small number of apomicts, for example in *Taraxacum* and in *Hieracium* (hawkweeds), the endosperm develops without fertilisation of the polar nuclei by a process known as autonomous endosperm development. In *Arabidopsis* a number a mutation are known which cause autonomous endosperm development.

The term 'parthenogenesis' as used herein refers to a form of asexual reproduction in which growth and development of embryos occur without fertilization. The genes and proteins of the invention can in combination with a parthenogenesis factor, for instance a gene or chemical factor, produce apomictic offspring.

The term 'vacuolar protein sorting-associated protein type 13' (abbreviated as VPS13) as used herein refers to a protein encoded by the Vps13 gene, which is involved in controlling the steps in the cycling of proteins through the trans-Golgi network to vacuoles and the cell membrane.

The term 'genetic marker' or 'polymorphic marker' as used herein refers to a region on the genomic DNA, which can be used to 'mark' a particular location on the chromosome. If a genetic marker is tightly linked to a gene or is 'in' a gene ('in gene marker) it "marks" the DNA on which the gene is found and can therefore be used in the (molecular) marker analysis as taught herein to select for or against the presence of the gene, e.g. in marker assisted breeding/selection (MAS) methods. Non-limiting examples of genetic markers are AFLP (amplified fragment length polymorphism, EP534858), microsatellite, RFLP (restriction fragment length polymorphism), STS (sequence tagged site), SNP (Single Nucleotide Polymorphism), SFP (Single Feature Polymorphism; see Borevitz et al. (2003) In: Genome Research Vol: 13, pp 513-523), SCAR (sequence characterized amplified region), CAPS markers (cleaved amplified polymorphic sequence) and the like. The further away the marker is from the gene, the more likely it is that recombination (crossing over) takes place between the marker and the gene, whereby the linkage (and co-segregation of marker and gene) is lost. The distance between genetic loci is measured in terms of recombination frequencies and is given in cM (centiMorgans; 1 cM is a meiotic recombination frequency between two markers of 1%). As genome sizes vary greatly between species, the actual physical distance represented by 1 cM (i.e. the kilobases, kb, between two markers) also varies greatly between species. It is understood that, when referring to 'linked' markers herein, this also encompasses markers 'in' the gene itself.

The term 'marker assisted selection' (abbreviated as 'MAS') as used herein refers to a process whereby plants are screened for the presence and/or absence of one or more genetic and/or phenotypic markers in order to accelerate the transfer of the DNA region comprising the marker (and optionally lacking flanking regions) into an (elite) breeding line. The term 'molecular maker assay' (or test) as used herein refers to a (DNA based) assay that indicates (directly or indirectly) the presence or absence of a particular allele (e.g. Dip allele) in a plant or plant part. Preferably, it allows one to determine whether a particular allele is homozygous or heterozygous at the Dip locus in any individual plant. For example, in one embodiment a nucleic acid linked to the Dip locus is amplified using PCR primers, the amplification product is digested enzymatically and, based on the electrophoretically resolved patterns of the amplification product, one can determine which Dip alleles are present in any individual plant and the zygosity of the allele at the Dip locus (i.e. the genotype at each locus). Non-limiting examples of molecular maker assay include the sequence characterized amplified region (SCAR) marker assay, the cleaved amplified polymorphic sequence (CAPS) marker assay and the like.

The term 'heterozygous' as used herein refers to a genetic condition existing if two (or more in case of polyploids) different alleles reside at a specific locus, such as the Dip locus (e.g. dominant Dip allele/recessive dip allele), but are positioned individually on corresponding pairs of homologous chromosomes in the cell.

The term 'homozygous' as used herein refers to a genetic condition existing when two (or more in case of polyploidy) identical alleles reside at a specific locus (e.g. homozygous for the dominant allele Dip, or homozygous for the recessive allele dip), but are positioned individually on corresponding homologous chromosomes in the cell.

The term 'variety' as used herein is in conformity with the UPOV convention and refers to a plant grouping within a single botanical taxon of the lowest known rank, which grouping can be defined by the expression of the characteristics resulting from a given genotype or combination of genotypes, can be distinguished from any other plant grouping by the expression of at least one of the said characteristics and is considered as a unit with regard to its suitability for being propagated unchanged (stable).

The terms 'polypeptide' and 'protein' as used herein are used interchangeably and refer to molecules consisting of a chain of amino acids, without reference to a specific mode of action, size, 3-dimensional structure or origin.

The terms 'isolated polypeptides' or 'isolated proteins' as used herein are used interchangeably and refer to a protein that is no longer in its natural environment, for example a protein present in a tube (in vitro) or in a recombinant bacterial or plant host cell is an isolated protein.

As used herein, the term 'nucleic acid' refers to any polymers or oligomers of pyrimidine and purine bases, preferably cytosine, thymine, and uracil, and adenine and guanine, respectively (See Albert L. Lehninger, Principles of Biochemistry, at 793-800 (Worth Pub. 1982) which is herein incorporated by reference in its entirety for all purposes). The present invention contemplates any deoxyribonucleotide, ribonucleotide or peptide nucleic acid component, and any chemical variants thereof, such as methylated, hydroxymethylated or glycosylated forms of these bases, and the like. The polymers or oligomers may be heterogenous or homogenous in composition, and may be isolated from naturally occurring sources or may be artificially or synthetically produced.

The terms 'polynucleotide', 'nucleic acid molecule', 'nucleic acid sequence' or 'nucleotide sequence' refer to a polymeric DNA or RNA molecule in single or double stranded form, particularly a DNA encoding a protein, variants or fragments thereof according to the invention.

The term 'isolated polynucleotide', 'isolated nucleic acid molecule', 'isolated nucleic acid sequence', or 'isolated nucleotide sequence' as used herein refers to a polynucleotide which is no longer in the natural environment, i.e. substantially separated from other cellular components which naturally accompany a native sequence or protein, e.g. ribosomes, polymerases, many other sequences and proteins. The term embraces a polynucleotide which has been removed from its naturally-occurring environment and includes recombinant or cloned nucleic acid isolates and chemically synthesized analogs or analogs biologically synthesized by heterologous systems e.g., the nucleic acid sequence in a bacterial host cell or in the plant nuclear or plastid genome.

The term 'functional DIP gene or protein' or 'functional DIP gene or protein variant or fragments' (such as orthologs or mutants, and part of a gene) as used herein refers to the capability of the gene and/or encoded protein to modify or induce in a plant (quantitative and/or qualitative) the processes underlying apomixis, particularly gametophytic apomixis through diplospory, by altering the expression level of one or more genes (e.g. by overexpression or silencing) in said plant. For example, the functionality of a putative DIP protein obtained from plant species X can be tested by various methods. Preferably, if the protein is functional, silencing of the Dip gene encoding the protein in plant species X, using e.g. gene silencing vectors, will lead to a reduction (i.e. the chromosome number will be reduced) or suppression of diplospory while overexpression in a susceptible plant will lead to enhanced diplospory. Also, complementation with a functional DIP protein will be capable of restoring or conferring diplospory. The skilled person will have no difficulties in testing functionality.

The term 'gene' as used herein refers to a DNA sequence comprising a region (transcribed region), which is transcribed into an RNA molecule (e.g. an mRNA) in a cell, operably linked to suitable regulatory regions (e.g. a promoter). A gene may thus comprise several operably linked sequences, such as a promoter, a 5' leader sequence comprising e.g. sequences involved in translation initiation, a (protein) coding region (cDNA or genomic DNA) and a 3' non-translated sequence comprising e.g. transcription termination sites.

The term 'chimeric gene' or 'recombinant gene' as used herein refers to any gene, which is not normally found in nature in a species, in particular a gene in which one or more parts of the nucleic acid sequence are present that are not associated with each other in nature. For example the promoter is not associated in nature with part or all of the transcribed region or with another regulatory region. The term 'chimeric gene' is understood to include expression constructs in which a promoter or transcription regulatory sequence is operably linked to one or more coding sequences or to an antisense (reverse complement of the sense strand) or inverted repeat sequence (sense and antisense, whereby the RNA transcript forms double stranded RNA upon transcription).

The term '3' UTR' or '3' non-translated sequence' (also known as '3' untranslated region' or '3'end') refers to the nucleic acid sequence found downstream of the coding sequence of a gene, which comprises for example a transcription termination site and (in most, but not all eukaryotic mRNAs) a polyadenylation signal (such as e.g. AAUAAA or variants thereof). After termination of transcription, the mRNA transcript may be cleaved downstream of the polyadenylation signal and a poly(A) tail may be added, which is involved in the transport of the mRNA to the cytoplasm (where translation takes place).

The term '5' UTR' or 'leader sequence' or '5' untranslated region' as used herein refers to a region of the mRNA transcript, and the corresponding DNA, between the +1 position where mRNA transcription begins and the translation start codon of the coding region (usually AUG on the mRNA or ATG on the DNA). The 5'UTR usually contains sites important for translation, mRNA stability and/or turnover, and other regulatory elements.

The term 'expression of a gene or variants or fragments thereof' as used herein refers to the process wherein a DNA region, which is operably linked to appropriate regulatory regions, particularly a promoter, is transcribed into an RNA, which is biologically active, i.e. which is capable of being translated into a biologically active protein or peptide (or active peptide fragment) or which is active itself (e.g. in posttranscriptional gene silencing or RNAi). An active protein in certain embodiments refers to a protein being constitutively active. The coding sequence is preferably in sense-orientation and encodes a desired, biologically active protein or peptide, or an active peptide fragment. In gene silencing approaches, the DNA sequence is preferably present in the form of an antisense DNA or an inverted repeat DNA, comprising a short sequence of the target gene in antisense or in sense and antisense orientation. "ectopic expression" refers to expression in a tissue in which the gene is normally not expressed.

The term 'transcription regulatory sequence' as used herein refers to a nucleic acid sequence that is capable of regulating the rate of transcription of a (coding) sequence operably linked to the transcription regulatory sequence. A transcription regulatory sequence as herein defined will thus comprise all of the sequence elements necessary for initiation of transcription (promoter elements), for maintaining and for regulating transcription, including e.g. attenuators or enhancers. Although mostly the upstream (5') transcription regulatory sequences of a coding sequence are referred to, regulatory sequences found downstream (3') of a coding sequence are also encompassed by this definition.

The term 'promoter' as used herein refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. Optionally the term 'promoter' may also include the 5'UTR region (e.g. the promoter may herein include one or more parts upstream (5') of the translation initiation codon of a gene, as this region may have a role in regulating transcription and/or translation.

The term 'constitutive promoter' as used herein refers to a promoter that is active in most tissues under most physiological and developmental conditions.

The term 'inducible promoter' as used herein refers to a promoter that is physiologically (e.g. by external application of certain compounds) or developmentally regulated.

The term 'tissue-specific promoter' as used herein refers to a promotor that is only active in specific types of tissues or cells. A "promoter active in plants or plant cells" refers to the general capability of the promoter to drive transcription within a plant or plant cell. It does not make any implications about the spatiotemporal activity of the promoter.

The term 'operably linked' as used herein refers to a linkage of polynucleotide elements in a functional relationship. A nucleic acid is 'operably linked' when it is placed into a functional relationship with another nucleic acid sequence. For instance, a promoter, or rather a transcription regulatory sequence, is operably linked to a coding sequence if it affects the transcription of the coding sequence. Operably linked means that the DNA sequences being linked are typically contiguous and, where necessary to join two protein encoding regions, contiguous and in reading frame so as to produce a chimeric protein.

The term 'chimeric protein' or 'hybrid protein' as used herein refers to a protein composed of various protein domains or motifs, which are not found as such in nature but which are joined to form a functional protein, which displays the functionality of the joined domains. A chimeric protein may also be a fusion protein of two or more proteins occurring in nature.

The term 'domain' as used herein refers to any part(s) or domain(s) of the protein with a specific structure or function that can be transferred to another protein for providing a new hybrid protein with at least the functional characteristic of the domain.

The terms 'target peptide' as used herein refers to amino acid sequences which target a protein, or protein fragment, to intracellular organelles such as plastids, preferably chloroplasts, mitochondria, or to the extracellular space or apoplast (secretion signal peptide). A nucleic acid sequence encoding a target peptide may be fused (in frame) to the nucleic acid sequence encoding the amino terminal end (N-terminal end) of the protein or protein fragment, or may be used to replace a native targeting peptide.

The term 'nucleic acid construct' or 'vector' as used herein refers to a man-made nucleic acid molecule resulting from the use of recombinant DNA technology and which is used to deliver exogenous DNA or RNA into a host cell. The vector backbone may for example be a binary or superbinary vector (see e.g. U.S. Pat. No. 5,591,616, US2002138879 and WO9506722), a co-integrate vector or a T-DNA vector, as known in the art and as described elsewhere herein, into which a chimeric gene is integrated or, if a suitable transcription regulatory sequence is already present, only a desired nucleic acid sequence (e.g. a coding sequence, an antisense or an inverted repeat sequence) is integrated downstream of the transcription regulatory sequence. Vectors usually comprise further genetic elements to facilitate their use in molecular cloning, such as e.g. selectable markers, multiple cloning sites and the like (see below).

The term 'host cell' or a 'recombinant host cell' or 'transformed cell' or 'transgenic cell' as used herein refer to a new individual cell (or organism) arising as a result of at least one nucleic acid molecule, especially comprising a chimeric gene encoding a desired protein or a nucleic acid sequence which upon transcription yields an antisense RNA or an inverted repeat RNA (or hairpin RNA) or an siRNA or miRNA for silencing of a target gene/gene family, having been introduced into said cell. The host cell is preferably a plant cell or a bacterial cell. The host cell may contain the nucleic acid construct as an extra-chromosomally (episomal) replicating molecule, or more preferably, comprises the chimeric gene integrated in the nuclear or plastid genome of the host cell.

The term 'recombinant plant' or 'recombinant plant part' or 'transgenic plant' as used herein refer to a plant or plant part (e.g. seed or fruit or leaves) comprising the chimeric gene as taught herein in all cells and plant parts at the same locus, even though the gene may not be expressed in all cells.

The term 'elite event' as used herein refers to a recombinant plant which has been selected to comprise the recombinant gene at a position in the genome which results in good or desired phenotypic and/or agronomic characteristics of the plant. The flanking DNA of the integration site can be sequenced to characterize the integration site and distinguish from other transgenic plants comprising the same chimeric gene at other locations in the genome.

The term 'selectable marker' as used herein refers to a commonly known term in the art and is used herein to describe any genetic entity which, when expressed, can be used to select for a cell or cells containing the selectable marker. Selectable marker gene products confer for example antibiotic resistance, or more preferably, herbicide resistance or another selectable trait such as a phenotypic trait (e.g. a change in pigmentation) or a nutritional requirement. The term 'reporter' is mainly used to refer to visible markers, such as green fluorescent protein (GFP), eGFP, luciferase, GUS and the like.

The term 'ortholog of a gene' or 'ortholog of protein' as used herein refers to the homologous gene or homologous protein found in another species, which has the same function as the gene or protein, but (usually) diverged in sequence from the time point on when the species harboring the genes diverged (i.e. the genes evolved from a common ancestor by speciation). In an embodiment, orthologs of the *Taraxacum* Dip gene may thus be identified in other plant species based on both sequence comparisons (e.g. based on percentages sequence identity over the entire sequence or over specific domains) and functional analysis.

The expression 'syntenic region' as used herein refers to a term used in comparative genomics and refers to the same region on a chromosome of two related species.

The term 'stringent hybridization conditions' as used herein refers to a situation which can be used to identify nucleotide sequences, which are substantially identical to a given nucleotide sequence. Stringent conditions are sequence-dependent and will be different in different circumstances. Generally, stringent conditions are selected to be about 5° C. lower than the thermal melting point (Tm) for the specific sequences at a defined ionic strength and pH. The Tm is the temperature (under defined ionic strength and pH) at which 50% of the target sequence hybridizes to a perfectly matched probe. Typically stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridizations (Northern blots using a probe of e.g. 100 nt) are for example those which include at least one wash in 0.2×SSC at 63° C. for 20 min, or equivalent conditions. Stringent conditions for DNA-DNA hybridization (Southern blots using a probe of e.g. 100 nt) are for example those which include at least one wash (usually 2) in 0.2×SSC at a temperature of at least 50° C., usually about 55° C., for 20 min, or equivalent conditions. See also Sambrook et al. (1989) and Sambrook and Russell (2001).

The term 'high stringency conditions' as used herein refers to condition that can be achieved for example, by hybridization at 65° C. in an aqueous solution containing 6×SSC (20×SSC contains 3.0 M NaCl, 0.3 M Na-citrate, pH 7.0), 5×Denhardt's (100×Denhardt's contains 2% Ficoll, 2% Polyvinyl pyrollidone, 2% Bovine Serum Albumin), 0.5% sodium dodecyl sulphate (SDS), and 20 µg/ml denatured carrier DNA (single-stranded fish sperm DNA, with an average length of 120-3000 nucleotides) as non-specific competitor. Following hybridization, high stringency washing may be done in several steps, with a final wash (about 30 min) at the hybridization temperature in 0.2-0.1×SSC, 0.1% SDS.

The term 'moderate stringency' as used herein refers to conditions equivalent to hybridization in the above described solution but at about 60-62° C. In that case the final wash is performed at the hybridization temperature in 1×SSC, 0.1% SDS.

The term 'low stringency' as used herein refers to conditions equivalent to hybridization in the above described solution at about 50-52° C. In that case, the final wash is performed at the hybridization temperature in 2×SSC, 0.1% SDS. See also Sambrook et al. (1989) and Sambrook and Russell (2001).

The term 'substantially identical' or 'substantial identity' or 'essentially similar' or essential similarity' or 'variant' or 'sequence identity' as used herein, when used in the context of amino acid sequences or nucleic acid sequences, refers to two amino acid sequences or two nucleotide sequences, when optimally aligned, such as by the programs GAP or BESTFIT using default parameters, share at least a certain percent sequence identity. GAP uses the Needleman and Wunsch global alignment algorithm to align two sequences over their entire length, maximizing the number of matches and minimizes the number of gaps. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919). It is clear that when RNA sequences are said to be essentially similar or have a certain degree of sequence identity with DNA sequences, thymine (T) in the DNA sequence is considered equal to uracil (U) in the RNA sequence. Sequence alignments and scores for percentage sequence identity may be determined using computer programs, such as the GCG Wisconsin Package, Version 10.3, available from Accelrys Inc., 9685 Scranton Road, San Diego, Calif. 92121-3752 USA. or using in EmbossWIN (version 2.10.0) the program "needle", using the same GAP parameters as described above or using gap opening penalty 10.0 and gap extension penalty 0.5, using DNAFULL as matrix. For comparing sequence identity between sequences of dissimilar lengths, it is preferred that local alignment algorithms are used, such as the Smith Waterman algorithm (Smith T F, Waterman M S (1981) J. Mol. Biol 147(1); 195-7), used e.g. in the EmbossWIN program "water". Default parameters are gap opening penalty 10.0 and gap extension penalty 0.5, using Blosum62 for proteins and DNAFULL matrices for nucleic acids.

The terms 'comprising' and 'to comprise', and their conjugations as used herein refer to a situation wherein said terms are used in their non-limiting sense to mean that items following the word are included, but items not specifically mentioned are not excluded. It also encompasses the more limiting verb "to consist of". In addition, reference to an element by the indefinite article 'a' or 'an' does not exclude the possibility that more than one of the element is present, unless the context clearly requires that there be one and only one of the elements. The indefinite article 'a' or 'an' thus usually means 'at least one'. It is further understood that, when referring to 'sequences' herein, generally the actual physical molecules with a certain sequence of subunits (e.g. amino acids) are referred to.

The term 'plant' as used herein includes plant cells, plant tissues or organs, plant protoplasts, plant cell tissue cultures from which plants can be regenerated, plant calli, plant cell clumps, and plant cells that are intact in plants, or parts of plants, such as embryos, pollen, ovules, sporangia, fruit, flowers, leaves (e.g. harvested lettuce crops), seeds, roots, root tips and the like.

The term 'gene silencing' as used herein refers to the down-regulation or complete inhibition of gene expression of one or more target genes (e.g. endogenous Dip genes). The use of inhibitory RNA to reduce or abolish gene expression is well established in the art and is the subject of several reviews (e.g Baulcombe 1996, Stam et al. 1997, Depicker and Van Montagu, 1997). There are a number of technologies available to achieve gene silencing in plants, such as chimeric genes which produce antisense RNA of all or part of the target gene (see e.g. EP 0140308 B1, EP 0240208 B1 and EP 0223399 B1), or which produce sense RNA (also referred to as co-suppression), see EP 0465572 B1. The most successful approach so far has however been the production of both sense and antisense RNA of the target gene ('inverted repeats'), which forms double stranded RNA (dsRNA) in the cell and silences the target gene. Methods and vectors for dsRNA production and gene silencing have been described in EP 1068311, EP 983370 A1, EP 1042462 A1, EP 1071762 A1 and EP 1080208 A1. A vector according to the invention may, therefore, comprise a transcription regulatory region which is active in plant cells operably linked to a sense and/or antisense DNA fragment of a DIP gene according to the invention. Generally short (sense and antisense) stretches of the target gene sequence, such as 17, 18, 19, 20, 21, 22 or 23 nucleotides of coding or non-coding sequence are sufficient. Longer sequences can also be used, such as 50, 100, 200 or 250 nucleotides or more. Preferably, the short sense and antisense fragments are separated by a spacer sequence, such as an intron, which forms a loop (or hairpin) upon dsRNA formation. Any short stretch of SEQ ID NO: 4 and/or SEQ ID NO:5, or fragments or variants thereof, may be used to make a DIP gene-derived silencing vector, and a transgenic plant in which one or more target genes are silenced in all or some tissues or organs (depending on the promoters used).

A convenient way of generating hairpin constructs is to use generic vectors such as pHANNIBAL and pHELLSGATE, vectors based on the Gateway® technology (see Wesley et al. 2004, Methods Mol Biol. 265:117-30; Wesley et al. 2003, Methods Mol Biol. 236:273-86 and Helliwell & Waterhouse 2003, Methods 30(4):289-95.), all incorporated herein by reference.

BRIEF DESCRIPTION OF THE FIGURES

FIG. 2. Association sequence polymorphism and diplospory phenotype within a broad *Taraxacum* germplasm panel. The differences between the sexual (dip) and the diplosporous alleles (Dip) are indicated in grey. FIG. 2 discloses SEQ ID NOS 4 and 13, respectively, in order of appearance.

DETAILED DESCRIPTION OF THE INVENTION

Figure 1A:
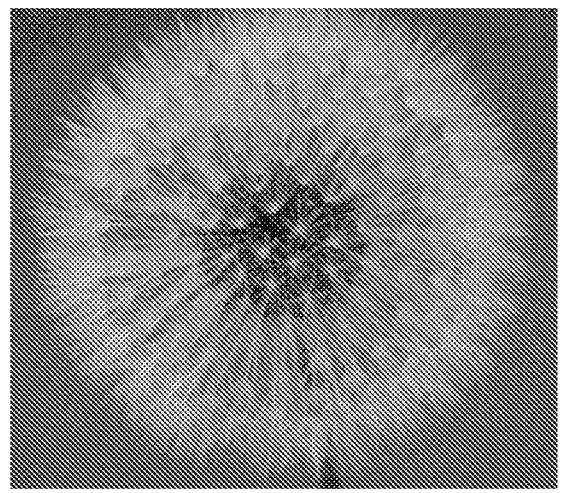
FIG. 1A. Seed head of fully apomictic triploid plant A68 (wildtype), in the absence of cross-pollination. Note the dark center of fully developed seeds.

In a first aspect, the present invention relates to an isolated polynucleotide comprising the nucleic acid sequence of SEQ ID NO:1, or a nucleic acid sequence having at least 50% or 70%, preferably at least 80%, more preferably at least 90%, even more preferably at least 95%, yet even more preferably at least 96% or 97%, most preferably at least 98% or 99% sequence identity to the nucleic acid sequence of SEQ ID NO:1.

In a second aspect, the invention relates to an isolated polynucleotide comprising the nucleic acid sequence of SEQ ID NO:2, or a nucleic acid sequence having at least 50% or 70%, preferably at least 80%, more preferably at least 90%, even more preferably at least 95%, yet even more preferably at least 96% or 97%, most preferably at least 98% or 99% sequence identity to the nucleic acid sequence of SEQ ID NO:2.

The isolated polynucleotides comprising the nucleic acid sequence of SEQ ID NO:1 or SEQ ID NO:2 were identified to be part of the putative Vacuolar Protein Sorting associated protein gene, Vps13, of *Taraxacum officinale* sensu lato. The Vps13 gene is a large gene. Hence, said nucleic acid sequences of SEQ ID NO:1 and SEQ ID NO:2 may be comprised in a single isolated nucleic acid sequence, i.e. being part of the same nucleic acid sequence. The isolated nucleic acid sequence may hence comprise both SEQ ID NO:1 and SEQ ID NO:2 or variants thereof. It is understood that the Vps13 gene may comprise many exons and introns, and other gene related sequences, such as promoter and terminator sequences encompassed in SEQ ID NO:1, extending to the 5' and 3' of the indicated protein encoding sequence (open reading frame; ORF) (SEQ ID NO:2) and may thus be larger than SEQ ID NO:2. Hence, the percentage of sequence identity may thus be relative not to the complete sequence of the isolated nucleic acid sequence. Rather, only the nucleic acid sequences comprised in said isolated nucleic acid sequence may have the said percentage of sequence identity with SEQ ID NO:1 or SEQ ID NO:2. It is thus understood that the percentage of sequence identity is then to be calculated relative to the nucleic acid sequence, which is comprised in the isolated nucleic acid sequence, of which the first and last nucleotide of the nucleic acid sequence align with the nucleic acid sequence of SEQ ID NO:1 and/or SEQ ID NO:2. Hence, when the percentage of sequence identity is to be calculated preferably it is only relative to the sequence corresponding to SEQ ID NO:1 and/or SEQ ID NO:2. It is also understood that SEQ ID NO:1 and SEQ ID NO:2 or variants thereof, are coding sequences, i.e. encode amino acid sequences. Hence, such coding sequences may in DNA be interspersed by intronic sequences. Hence, in case sequence identity is calculated from a DNA sequence, parts of sequences that do not show an alignment with SEQ ID NO. 1 and/or SEQ ID NO:2, such as introns, are not to be taken into account.

In an embodiment, the isolated polynucleotides as taught herein have the nucleic acid sequence of SEQ ID NO:1 or SEQ ID NO:2 or variants thereof as taught herein.

In an embodiment, the isolated polynucleotides as taught herein comprising the nucleic acid sequence of SEQ ID NO:1 or SEQ ID NO:2 or variants or fragments thereof as taught herein may be referred to as 'Dip, or DIP polynucleotides' or 'Dip or DIP genes' or 'apomixis polynucleotides or apomixis genes' or 'diplospory polynucleotides or diplospory genes'.

In an embodiment, the isolated polynucleotides as taught herein comprising the nucleic acid sequence of SEQ ID NO:1 or SEQ ID NO:2 or variants thereof as taught herein and/or the expression product of said polynucleotides and/or the protein encoded by said polynucleotides are capable of providing diplospory function to a plant or plant cell or capable of inducing diplospory or diplospory as part of gametophytic apomixis, preferably the type that occurs though diplospory, preferably in crops that are currently considered to be sexual crops. Gametophytic apomixis through diplospory produces offspring that are genetically identical to the parent plant. Thus in an embodiment, the isolated polynucleotides or variants thereof as taught herein may be used to produce offspring that are genetically identical to the parent plant without the need for fertilization and cross-breeding.

In a preferred embodiment, the Dip polynucleotides or genes and variants thereof as taught above and/or the expression product of said polynucleotides and/or the protein encoded by said polynucleotides are capable of providing diplospory function to a plant or plant cell, preferably the type that occurs though diplospory, in sexual crops when introduced into a plant or plant cell.

It is understood that the term 'isolated polynucleotides' or variants thereof (e.g. genomic DNA cDNA, or mRNA) includes naturally-occurring, artificial or synthetic nucleic acid molecules. The nucleic acid molecules may encode any of the polypeptides or variants thereof as taught herein. Said nucleic acid molecules may be used to produce the polypeptides or proteins or variants thereof as taught herein. Due to the degeneracy of the genetic code various nucleic acid molecules may encode the same polypeptide (e.g. polypeptides or proteins or variants thereof as taught herein comprising the amino acid sequence of SEQ ID NO:3 and/or SEQ ID NO: 7 or 12).

In an embodiment, the isolated polynucleotides as taught herein include any variant nucleic acid molecules, which encompass any nucleic acid molecules comprising a nucleotide sequence having more than 50%, preferably more than 55%, preferably more than 60%, preferably more than 65%, preferably more than 70%, preferably more than 75%, preferably more than 80%, preferably more than 85%, preferably more than 90%, preferably more than 95%, preferably more than 96%, preferably more than 97%, preferably more than 98%, and preferably more than 99% sequence identity with the nucleic acid sequence of SEQ ID NO: 1 or SEQ ID NO:2. Variants also include nucleic acid molecules, which have been derived, by way of one or more nucleic acid substitutions, deletions or insertions, from the nucleic acid molecule having the nucleic acid sequence of SEQ ID NO: 1 or SEQ ID NO:2. Preferably, such nucleic acid molecules comprise from 1, 2, 3, 4, 5, 6, 7, 8, 9, 10 or more up to about 100, 90, 80, 70, 60, 50, 45, 40, 35, 30, 25, 20, 15 nucleic acid substitutions, deletions or insertions as compared to SEQ ID NO: 1 or SEQ ID NO:2. Sequence identity may be determined by any suitable means available in the art. For instance, bioinformatics may be used to perform pairwise alignment between nucleic acid sequences to identify regions of similarity that may be due to functional, structural, or evolutionary relationships between the sequences. It is also understood that many methods can be used to identify, synthesize or isolate variants of the polynucleotide as taught herein, such as nucleic acid hybridization, PCR technology, in silico analysis and nucleic acid synthesis, and the like.

In an embodiment, the term 'variant' also encompasses natural variants, which are found in nature, e.g. in other *Taraxacum* species or in other plants. Said variant nucleotide sequences isolated from other *Taraxacum* species or in other plants may encompass dominant Dip alleles as well as recessive dip alleles from different plant species, e.g. encompassing different *Taraxacum* species, cultivars, accessions or breeding lines. For example, without being bound by theory, the EMS mutations identified in the examples are variants that may be regarded as recessive dip, as diplospory function was lost, whereas the wild-type sequence may be regarded as dominant Dip, as the wild-type sequence provided diplospory function.

In an embodiment, variant isolated polynucleotides according to the invention, such as homologous or orthologs, may also be found in and/or isolated from plants other than those belonging to the genus *Taraxacum*. Said isolated polynucleotides may be isolated from other wild or cultivated apomictic or non-apomictic plants and/or from other plants, using known methods such as PCR, stringent hybridization methods, and the like. Thus, variants of SEQ ID NO:1 and/or SEQ ID NO:2 include also nucleotide sequences found e.g. naturally in other *Taraxacum* plants, lines or cultivars, and/or found naturally in other plants of other species. Such nucleotides may for example be identified in a Blast search, or by identifying corresponding sequences de novo in planta.

In an embodiment, the isolated polynucleotide variants as taught herein include, for example, isolated polynucleotides according to the invention derived from a different 'origin' than that of SEQ ID NO:1 and/or SEQ ID NO:2, which are of *Taraxacum* origin. Thus, in particular the invention encompasses the genes or alleles derived from an plant wherein diplospory (as part of gametophytic apomixis through diplospory) is present, such as a wild or cultivated plant and/or from other plants. Such homologues can be easily isolated using the provided nucleotide sequences and/or complementary sequences thereof, or parts thereof as primers or probes. For example, moderately stringent, stringent or highly stringent nucleic acid hybridization methods can be used. For example, fragments of the sequences of SEQ ID NO. 1 and/or SEQ ID NO:2, or complementary sequences thereof may be used. Said fragments to be used in such hybridization methods may comprise at least 10, 20, 30, 40, 50, 100, 150, 200, 250, 300, 400, 500, 600, 700, 800, 900, 1000, 1500, 2000, 3000 or more contiguous nucleic acids of SEQ ID NO. 1 and/or SEQ ID NO:2.

It is understood that due to the degeneracy of the genetic code, various nucleic acid sequences may encode the same amino acid sequence. For optimal expression in a host, the isolated nucleic acid sequences according to the invention can be codon-optimized by adapting the codon usage to that most preferred in plant genes, particularly to genes native to the plant genus or species of interest (Bennetzen & Hall, 1982, J. Biol. Chem. 257, 3026-3031; Itakura et al., 1977 Science 198, 1056-1063) using available codon usage Tables (e.g. more adapted towards expression in the plant of interest). Codon usage Tables for various plant species are published for example by Ikemura (1993, In "Plant Molecular Biology Labfax", Croy, ed., Bios Scientific Publishers Ltd.) and Nakamura et al. (2000, Nucl. Acids Res. 28, 292.) and in the major DNA sequence databases (e.g. EMBL at Heidelberg, Germany). Accordingly, synthetic DNA sequences can be constructed so that the same or substantially the same proteins are produced. Several techniques for modifying the codon usage to that preferred by the host cells can be found in patent and scientific literature. The exact method of codon usage modification is not critical for this invention.

Small modifications to a DNA sequence such as described above can be routinely made, i.e., by PCR-mediated mutagenesis (Ho et al., 1989, Gene 77, 51-59., White et al., 1989, Trends in Genet. 5, 185-189). Modifications to a DNA sequence can also be routinely introduced by de novo DNA synthesis of a desired coding region using available techniques.

In an embodiment, the isolated polynucleotide or variants thereof according to the invention can be modified so that the N-terminus of the DIP protein has an optimum translation initiation context, by adding or deleting one or more amino acids at the N-terminal end of the protein. Often it is preferred that the proteins of the invention to be expressed in plants cells start with a Met-Asp or Met-Ala dipeptide for optimal translation initiation. An Asp or Ala codon may thus be inserted following the existing Met, or the second codon, Val, can be replaced by a codon for Asp (GAT or GAC) or Ala (GCT, GCC, GCA or GCG). The DNA sequences may also be modified to remove illegitimate splice sites.

The isolated polynucleotides or variants thereof according to the invention, are preferably 'functional', i.e. they preferably are capable of providing diplospory function to a plant, preferably as part of gametophytic apomixis, preferably the type that occurs through diplospory, in plant or plant cell or sexual crop. In one embodiment, isolated polynucleotides or variants thereof are provided, which are homologous to the polynucleotide comprising nucleic acid sequence SEQ ID NO:1 and/or SEQ ID NO:2, which are derived from *Taraxacum*, said isolated polynucleotides being isolated from apomictic plants. Hence, the isolated polynucleotides or variants thereof according to the invention, in this embodiment, are isolated from apomictic plants. Such isolated polynucleotides or variants thereof may be in particular capable of providing the diplospory function to a plant, in plant or plant cell or (sexual) crop.

It is understood that the variants of the polynucleotides as taught herein exert the same function as the polynucleotides comprising the nucleic acid sequence of SEQ ID NO:1 or SEQ ID NO:2 as taught herein, i.e. are capable of providing diplospory function to a plant or plant cell preferably as part of inducing diplospory or gametophytic apomixis, in plant or plant cell or sexual crop, particularly when introduced in a in plant or plant cell or sexual crop. It is further understood that any isolated polynucleotides and variants thereof as taught herein may encode any of the polypeptides and variants thereof as taught herein.

In an embodiment, the expression product of the polynucleotides and variants thereof as taught herein is an RNA molecule, preferably an mRNA molecule or an siRNA or miRNA molecule.

In an embodiment, a fragment of the polynucleotides and variants thereof as taught herein and/or the expression product of said fragment and/or the protein encoded by said fragment is capable of providing diplospory function to a plant or plant cell preferably as part of inducing gametophytic apomixis.

In a preferred embodiment, the fragment as taught herein and/or the protein encoded by said fragment is capable of providing diplospory function, preferably inducing diplospory or as part of inducing gametophytic apomixis.

In an embodiment, the expression product of the fragment as taught herein is an RNA molecule, preferably a mRNA molecule or an siRNA or miRNA molecule.

In an embodiment, the fragment as taught herein may have a length of at least 20, 30, 40, 50, 100, 150, 200, 250, 300, 400, 500, 600, 700, 800, 900, 1000, 1500, 2000 or 3000 contiguous nucleotides of the isolated polynucleotides comprising the nucleic acid sequence of SEQ ID NO; 1 or SEQ ID NO:2 and variant thereof as taught herein.

In a preferred embodiment, the fragment as taught herein has the nucleic acid sequence of SEQ ID NO:4, 6 or 11.

In a further preferred embodiment, the expression product of the fragment as taught herein has the nucleic acid sequence of SEQ ID NO:5.

In an embodiment, the expression product of the fragment as taught herein encodes a polypeptide comprising the amino acid sequence as set forth in SEQ ID NO:7 and/or 12.

Chimeric Gene and Vectors

In an embodiment, a chimeric gene may comprise any of the polynucleotides, fragments and variants thereof as taught herein.

In an embodiment, any of the polynucleotides, fragments and variants thereof as taught herein, when comprised in the vector as taught herein, may be operably linked to a promoter. Any promoters known in the art, and which are suitable for linkage with the polynucleotides, fragments and variants thereof as taught herein may be used. Non-limiting examples of suitable promoters include promoters allowing constitutive or regulated expression, weak and strong expression, and the like. Any known methods in the art may be used to incorporate the polynucleotides, variants or fragments thereof as taught herein in a chimeric gene.

In certain embodiment, it may be advantageous to operably link the polynucleotides, fragments and variants thereof as taught herein to a so-called 'constitutive promoter'. Alternatively, it may be advantageous to operably link the polynucleotides, fragments and variants thereof as taught herein to a so-called 'inducible promoter'. An inducible promoter may be a promoter that is physiologically (e.g. by external application of certain compounds) regulated.

In an embodiment, the promoter which is operably linked to isolated polynucleotides, variants or fragments thereof as taught herein may be for example a constitutively active promoter, such as: the strong constitutive 35S promoters or enhanced 35S promoters (the "35S promoters") of the cauliflower mosaic virus (CaMV) of isolates CM 1841 (Gardner et al., 1981, Nucleic Acids Research 9, 2871-2887), CabbB-S (Franck et al., 1980, Cell 21, 285-294) and CabbB-JI (Hull and Howell, 1987, Virology 86, 482-493); the 35S promoter described by Odell et al. (1985, Nature 313, 810-812) or in U.S. Pat. No. 5,164,316, promoters from the ubiquitin family (e.g. the maize ubiquitin promoter of Christensen et al., 1992, Plant Mol. Biol. 18, 675-689, EP 0 342 926, see also Cornejo et al. 1993, Plant Mol. Biol. 23, 567-581), the gos2 promoter (de Pater et al., 1992 Plant J. 2, 834-844), the emu promoter (Last et al., 1990, Theor. Appl. Genet. 81, 581-588), *Arabidopsis* actin promoters such as the promoter described by An et al. (1996, Plant J. 10, 107.), rice actin promoters such as the promoter described by Zhang et al. (1991, The Plant Cell 3, 1155-1165) and the promoter described in U.S. Pat. No. 5,641,876 or the rice actin 2 promoter as described in WO070067; promoters of the *Cassava* vein mosaic virus (WO 97/48819, Verdaguer et al. 1998, Plant Mol. Biol. 37, 1055-1067), the pPLEX series of promoters from Subterranean Clover Stunt Virus (WO 96/06932, particularly the S7 promoter), an alcohol dehydrogenase promoter, e.g., pAdh1S (GenBank accession numbers X04049, X00581), and the TR1' promoter and the TR2' promoter (the "TR1'promoter" and "TR2'promoter", respectively) which drive the expression of the 1' and 2' genes, respectively, of the T-DNA (Velten et al., 1984, EMBO J 3, 2723-2730), the Figwort Mosaic Virus promoter described in U.S. Pat. No. 6,051,753 and in EP426641, histone gene promoters, such as the Ph4a748 promoter from *Arabidopsis* (PMB 8: 179-191), or others.

As the constitutive expression of a chimeric gene, genetic construct or vector in a plant may have a high cost on fitness of the plants, it is in one embodiment preferred to use a promoter whose activity is inducible. Examples of inducible promoters are wound-inducible promoters, such as the MPI promoter described by Cordera et al. (1994, The Plant Journal 6, 141), which is induced by wounding (such as caused by insect or physical wounding), or the COMPTII promoter (WO0056897) or the PR1 promoter described in U.S. Pat. No. 6,031,151. Alternatively the promoter may be inducible by a chemical, such as dexamethasone as described by Aoyama and Chua (1997, Plant Journal 11: 605-612) and in U.S. Pat. No. 6,063,985 or by tetracycline (TOPFREE or TOP 10 promoter, see Gatz, 1997, Annu Rev Plant Physiol Plant Mol Biol. 48: 89-108 and Love et al. 2000, Plant J. 21: 579-88).

A promoter can be utilized which is not constitutive but rather is specific for one or more tissues or organs of the plant. Preferably a promoter is tissue specific. Promoters may be preferably developmentally regulated, for example leaf preferred or epidermis preferred, whereby the said nucleic acid sequence is expressed only or preferentially in cells of the specific tissue(s) or organ(s) and/or only during a certain developmental stage, preferably in female ovaries, megaspore mother cells and/or in female gametes. For example, the Dip gene(s) can be selectively expressed in the leaves of a plant by placing the coding sequence under the control of a light-inducible promoter such as the promoter of the ribulose-1, 5-bisphosphate carboxylase small subunit gene of the plant itself or of another plant, such as pea, as disclosed in U.S. Pat. No. 5,254,799 or *Arabidopsis* as disclosed in U.S. Pat. No. 5,034,322 and others.

The term 'inducible' does not necessarily require that the promoter is completely inactive in the absence of the inducer stimulus. A low level non-specific activity may be present, as long as this does not result in severe yield or quality penalty of the plants. Inducible, thus, preferably refers to an increase in activity of the promoter, resulting in an increase in transcription of the downstream encoding region following contact with the inducer.

In a preferred embodiment, the promoter of an endogenous gene is used for expressing a protein comprising an amino acid sequence of SEQ ID NO:3 or variants or fragments thereof (e.g. SEQ ID NO:7 and/or 12) thereof as taught herein. For example, the promoter of a *Taraxacum* Dip allele or corresponding promoter from another plant species may be isolated and operably linked to a nucleic acid sequence encoding a protein according to the invention. Said protein is preferably capable of providing diplospory function, preferably as part of diplospory or gametophytic apomixis. The said promoter, i.e. the upstream transcription regulatory region normally within about 2000 base pairs (bp) upstream of the transcription start site and/or translation start codon, of a polynucleotide encoding a protein comprising an amino acid sequence of SEQ ID NO:3 or fragments or a variants thereof (e.g. SEQ ID NO:7 and/or 12) as taught herein, such as the homologs of other *Taraxacum* origins and/or other plants, can be isolated from apomictic plants and/or other plants using known methods, such as TAIL-PCR (Liu et al. 1995, Genomics 25(3):674-81; Liu et al. 2005, Methods Mol. Biol. 286:341-8), Linker-PCR, or Inverse PCR (IPCR). It is understood that as the said gene sequences are part of the putative Vacuolar Protein Sorting associated protein gene, Vps13, (SEQ ID 1) of *Taraxacum officinale* sensu lato, the said promoter comprises sequences located within SEQ ID 1 which are located 5' of the gene encoding region (SEQ ID 2) or other regions of SEQ ID 1 located 5' of an expressed sub-genomic region that is expressed as mRNA, miRNA or siRNA. Expressed mRNA, siRNA or miRNA is to encompass the female gametophytic stage, i.e. its expression activity can be traced to place and time of expression of the diplospory phenotype or the developmental stage leading to the this stage.

In an embodiment of the invention, an endogenous promoter may be used which is derived from a polynucleotide encoding a protein comprising an amino acid sequence of SEQ ID NO:3 or fragments or variants thereof as taught herein, such as homologs of other *Taraxacum* origins and/or other plants. Also sequences which are longer than these sequences may be used. For any of the said nucleic acid sequence the region up to about 2000 bp upstream of the translation start codon of the coding region may comprise transcription regulatory elements. Thus, in one embodiment the nucleotide sequence which is 2000 bp, 1500 bp, 1000 bp, 800 bp, 500 bp, 300 bp or less upstream of the translation or transcription start site of the said polynucleotide may be isolated, and its promoter activity may be tested and, if functional, the sequence may be operably linked to polynucleotide encoding a protein comprising an amino acid sequence of SEQ ID NO:3 or fragments or variants thereof as taught herein, e.g. SEQ ID NO:7 and/or 12. Promoter activity of whole sequences and fragments thereof can be tested by e.g. deletion analysis, whereby 5' and/or 3' of a transcription start site regions are deleted and the promoter activity is tested using known methods (e.g. operably linking the promoter with a deletion or deletions to a reporter gene).

In another embodiment, said promoter drives the expression of the miRNA and siRNA molecules of the invention.

Whether a Dip allele originating from a plant having diplospory function or not is capable of providing or inducing diplospory, preferably as part of gametophytic apomixis, in a plant or plant cell or sexual crop according to the invention may depend on the molecular function of the polypeptide or protein encoded by the isolated polynucleotides as taught herein. In one embodiment the protein encoded by the isolated polynucleotides, fragments and variants thereof as taught herein may have a dominant function, provided by expressing or overexpressing a protein comprising an amino acid sequence of SEQ ID NO:3, or variants or fragment thereof (e.g. SEQ ID NO:7 and/or 12) as taught herein. Said isolated polynucleotide encoding the said protein when expressed in a plant is capable of providing diplospory function to a plant or enhancing diplospory function in a plant or is capable of inducing or enhancing diplospory in a plant or plant cell or crop.

For example, when a polynucleotide comprising the nucleic acid sequence of SEQ ID NO:1 and/or SEQ ID NO:2 or fragments or variants thereof (e.g. SEQ ID NO: 4, 5, 6, or 11) is expressed in a plant from a suitable plant promoter and functional amounts of the encoded protein are made, the diplospory function or the occurrence of diplospory preferably as part of gametophytic apomixis may be induced or significantly enhanced as compared with plants lacking said protein. Functionality (i.e. capacity of the polynucleotide, variant or fragment thereof as taught herein to induce or cause diplospory in a plant) can be tested by introducing such a nucleic acid sequence in a suitable host plant such that it is expressed therein, e.g. a non-diplosporous *Taraxacum* line, and analyzing the effect on diplospory function of the transformants in a bioassay, such as e.g. described in the examples as taught herein.

In an embodiment, silencing of an expressed polynucleotide, variant or fragment thereof as taught herein, which is capable of encoding a protein comprising an amino acid sequence of SEQ ID NO:3 or variants or fragments thereof (e.g. SEQ ID NOs: 7 and/or 12) may lead to loss-of-function, i.e. to reduced diplospory or absence of diplospory or non-occurrence of gametophytic apomixis through diplospory. Hence, the skilled person can easily determine whether a polynucleotide or variant or fragment thereof encoding a protein comprising an amino acid sequence of SEQ ID NO:3 or fragments or variants thereof (e.g. SEQ ID NOs: 7 and/or 12) and/or fragment thereof as described herein is capable of providing diplospory preferably as part of gametophytic apomixis in a plant or plant cell or crop.

In one embodiment, the chimeric gene as taught herein is provided comprising any one of the isolated polynucleotides (SEQ ID NO:1 or SEQ ID NO:2), variants or fragments thereof (e.g. SEQ ID NO: 4, 5, 6, or 11) as taught herein. Said chimeric gene is preferably capable of providing diplospory function to a plant in a plant or plant cell or crop according to the invention.

In an embodiment, the polynucleotides (e.g. SEQ ID No:1 or SEQ ID NO:2), variants or fragments thereof (e.g. SEQ ID NO: 4, 5, 6, or 11) as taught herein or the chimeric gene as taught herein may be comprised in a genetic construct.

In a preferred embodiment, the genetic construct as taught herein may comprise an open reading frame of the isolated polynucleotides of the invention (e.g. SEQ ID:2), variants or fragments thereof (e.g. SEQ ID NO: 4, 5, 6, or 11) as taught herein.

In an embodiment, the isolated polynucleotides (e.g. SEQ ID NO:1 or SEQ ID NO:2), variants or fragments thereof (e.g. SEQ ID NO: 4, 5, 6 or 11) as taught herein may be comprised in a nucleic acid vector.

The construction of chimeric genes, genetic constructs and vectors according to the invention is generally known in the art. Said chimeric genes, genetic constructs and vectors are preferably capable of providing diplospory function to a plant or capable of inducing diplospory or gametophytic apomixis through diplospory in a plant, plant cell or crop. Chimeric genes may be generated by modifying endogenous gene sequences. For example, a recessive allele (i.e. dip) may be modified such that it is changed into a dominant allele (i.e. Dip) in case the dominant allele is capable of providing diplospory function or capable of inducing diplospory or gametophytic apomixis through diplospory in a plant, plant cell or crop. Or, alternatively, endogenous genes that would be capable of providing diplospory function or capable of inducing diplospory or gametophytic apomixis through diplospory but that are not expressed may be modified, e.g. by modifying the endogenous promoter sequences such that the endogenous genes will be expressed. Such modifications may include (targeted) mutagenesis whereby at least 1, 5, 10, 20, 50, 100, 200, 500, or 1000 nucleotides of an endogenous gene are mutated. An example of such a modification may be found in example 5, wherein the four mutations found in the EMS mutation to confer a loss of diplospory phenotype, hence, reversing said mutations may provide for a gain of diplospory phenotype.

In an embodiment, the chimeric genes as taught herein may be generated by operably linking the nucleic acid sequence encoding a protein (or variant or fragment) according to the invention to a promoter sequence, suitable for expression in the host cells, using standard molecular biology techniques. The promoter sequence may already be present in a vector so that the nucleic acid sequence is simply inserted into the vector downstream of the promoter sequence. In one embodiment a chimeric gene comprises a suitable promoter for expression in plant cells or microbial cells (e.g. bacteria), operably linked to a nucleic acid sequence according to the invention, optionally followed by a 3' non-translated nucleic acid sequence. The nucleic acid sequence according to the invention is optionally preceded by a 5' untranslated sequence region (UTR). The promoter, 3' UTR and/or 5' UTR may, for example, be from an endogenous Dip gene, or may be from other sources, as described below. In addition, the nucleic acid sequence according to the invention may also include intronic sequences, which can be included in the 3' UTR or 5' UTR sequence, but may also be introduced in coding sequence of the nucleic acid sequence according to the invention.

In an embodiment, the chimeric genes, genetic constructs and vectors as taught herein are preferably capable to express a nucleic acid sequence encoding an amino acid sequence according to the invention, wherein said amino acid sequence according to the invention is preferably capable of providing diplospory function to a plant preferably as part of gametophytic apomixis in a plant or plant cell or crop. Hence, said chimeric genes, genetic constructs and vectors preferably comprise dominant Dip alleles according to the invention.

In an embodiment, the nucleic acid vector as taught herein may comprise a promoter sequence active in plant cells operably linked to any one of isolated polynucleotides (e.g. SEQ ID NO:1 or SEQ ID NO:2), variants or fragments thereof (e.g. SEQ ID NO: 4, 5, 6, or 11) as taught herein or a chimeric gene as taught herein or a genetic construct as taught herein.

In a preferred embodiment, the promoter sequence of the nucleic acid vector as taught herein, may comprise:
  a) the native promoter sequence of the nucleic acid sequence of SEQ ID NO:1 and/or SEQ ID NO:2;
  b) a functional fragment of the promoter sequence of a); or
  c) a nucleic acid sequence comprising at least 70%, preferably at least 80%, more preferably at least 90%, most preferably at least 95% sequence identity with the native promoter sequence of the nucleic acid sequence of SEQ ID NO:1 and/or SEQ ID NO:2;
  d) the native promoter sequence of the nucleic acid sequence of SEQ ID NO:6;
  e) a functional fragment of the promoter sequence of d); or
  f) a nucleic acid sequence comprising at least 70%, preferably at least 80%, more preferably at least 90%, most preferably at least 95% sequence identity with the native promoter sequence of the nucleic acid sequence of SEQ ID NO:6.

In a preferred embodiment, the promoter of the nucleic acid vector as taught herein is a female ovary-specific promoter, preferably a megaspore mother cell-specific promoter and/or female gamete-specific promoter.

Isolated Polypeptide

In a third aspect, the present invention relates to an isolated polypeptide comprising the amino acid sequence of SEQ ID NO:3, or an amino acid sequence having at least 50% or 70%, preferably at least 80%, more preferably at least 90%, even more preferably at least 95%, yet even more preferably at least 96% or 97%, most preferably at least 98% or 99% sequence identity to the amino acid sequence of SEQ ID NO:3.

In a preferred embodiment, the polypeptide as taught herein has the amino acid sequence of SEQ ID NO:3 or variants or fragments thereof.

In an embodiment, the isolated polypeptides as taught herein comprising the amino acid sequence of SEQ ID NO:3 and variants or fragments thereof as taught above may be referred to as DIP polypeptide or protein' or 'apomixis-related polypeptides or proteins'.

In an embodiment, the DIP polypeptides or proteins and variants or fragments thereof as taught above are capable of providing diplospory function to a plant or plant cell, preferably as part of inducing diplospory or gametophytic apomixis in crops. Thus in an embodiment, the isolated polypeptides or proteins as taught herein may be used to produce offspring that are genetically identical to the parent plant without the need for fertilization and cross-breeding.

In a preferred embodiment, the DIP polypeptides or proteins and variants or fragments thereof, preferably as part of gametophytic apomixis, as taught above are capable of providing diplospory function to a plant or plant cell or capable of inducing diplospory, in crops, particularly when introduced into a plant or plant cell.

The polypeptides or proteins having the amino acid sequence of SEQ ID NO:3 or variants thereof as taught herein were identified to be the putative Vacuolar Protein Sorting associated protein gene, Vps13, of *Taraxacum officinale* sensu lato or part thereof. The Vps13 gene is a large gene. Hence, said amino acid sequences of SEQ ID NO:3 may be comprised in a single isolated protein, i.e. being part of the same amino acid sequence, or parts of that same amino acid sequence. The isolated protein may hence comprise both SEQ ID NO:3 or variants thereof. It is understood that as the Vps13 gene may constitute a large protein, when compared to the size of the amino acid sequences of SEQ ID NO:3 or variants thereof, that the percentage of sequence identity may be relative not to the complete sequence of the isolated protein. Rather, only the amino acid sequence comprised in said isolated protein may have the said percentage of sequence identity with SEQ ID NO:3. It is thus understood that the percentage of sequence identity is then to be calculated relative to the amino acid sequence, which is comprised in the isolated protein, of which the first and last amino acid of the amino acid sequence align with the amino acid sequence of SEQ ID NO:3. Hence, when the percentage of sequence identity is to be calculated preferably it is only relative to the sequence corresponding to SEQ ID NO:3.

It is understood that the polypeptides as taught herein also includes variant polypeptides having the amino acid sequence of SEQ ID NO:3, the amino acid sequences of said variants having more than 50%, preferably more than 55%, more than 60%, more than 65%, more than 70%, preferably more than 75%, more than 80%, more than 85%, more than 90%, more than 95%, preferably more than 96%, preferably more than 97%, preferably more than 98%, and preferably more than 99% sequence identity with the amino acid sequence of SEQ ID NO:3. Variants polypeptide having the amino acid sequence of SEQ ID NO:3 also include polypeptides, which have been derived, by way of one or more amino acid substitutions, deletions or insertions, from the polypeptide having the amino acid sequence of SEQ ID NO:3. Preferably, such polypeptides comprise from 1, 2, 3, 4, 5, 6, 7, 8, 9, 10 or more up to about 100, 90, 80, 70, 60, 50, 45, 40, 35, 30, 25, 20, 15 amino acid substitutions, deletions or insertions as compared to the polypeptide having the amino acid sequence of SEQ ID NO:3.

In an embodiment, the variants polypeptides as taught herein may differ from the provided amino acid sequences by one or more amino acid deletions, insertions and/or replacements and include natural and/or synthetic/artificial variants.

In an embodiment, the term 'variant polypeptides' also encompasses natural variant polypeptides which are found in nature, e.g. in cultivated or wild lettuce plants and/or other plants. Isolated proteins also include fragments, i.e. non-full length peptides, of the isolated proteins. Fragments include peptides comprising or consisting of at least 10, 20, 30, 40, 50, 100, 150, 200, 250, 300, 400, 500, 600, 700, 800, 900, 1000 or more contiguous amino acids of the amino acid sequences encoded by SEQ ID NO:3, or variants thereof, especially comprising or consisting of at least 10, 20, 30, 40, 50, 100, 150, 200, 250, 300, 400, 500, 600, 700, 800, 900, 1000, or more contiguous amino acids of SEQ ID NO:3 or variants thereof.

The isolated polypeptides or variants thereof as taught herein are preferably capable of providing diplospory function to a plant, preferably capable of inducing diplospory or gametophytic apomixis in a plant or plant cell or crop. Diplospory is. This means that the isolated polypeptides, fragments and variants according to the invention are capable of inducing diplospory. Diplospory function according to the invention includes skipping of the first female reduction division (Meiosis I), resulting in two unreduced megaspores with the same genotype as the mother plant. One of these megaspores degenerates and the other surviving unreduced megaspore gives rise to the unreduced megagametophyte (or embryo sac), containing an unreduced egg cell. This unreduced egg cell develops without fertilization into an embryo and has the same genotype as the mother plant, i.e. is a clone of the mother plant.

In an embodiment, the isolated polypeptides or variants thereof as taught herein may be isolated from natural sources, synthesized de novo by chemical synthesis (using e.g. a peptide synthesizer such as supplied by Applied Biosystems) or produced by recombinant host cells by expressing the nucleic acid sequence encoding the isolated polypeptides, fragments and variants thereof as taught herein.

In an embodiment, the isolated polypeptides or variants thereof as taught herein may comprise conservative amino acid substitutions within the categories:
basic (e.g. Arg, His, Lys);
acidic (e.g. Asp, Glu);
nonpolar (e. g. Ala, Val, Trp, Leu, Ile, Pro, Met, Phe, Trp); or
polar (e. g. Gly, Ser, Thr, Tyr, Cys, Asn, Gln).

In addition, non-conservative amino acid substitutions may also fall within the scope of the invention.

In an embodiment, the isolated polypeptides or variants thereof as taught herein may also be a chimeric polypeptide, such as a polypeptide composed of at least two different domains. Since SEQ ID NO:3 is derived, or partially derived, from the Vps13 gene, SEQ ID NO:3 or variants thereof, may be exchanged with the corresponding sequence in a Vps13 protein, which is not or which is less capable of providing diplospory function or not capable of inducing gametophytic apomixis through diplospory in a plant or plant cell or crop. This way, a chimeric polypeptide or protein may be obtained which is capable of providing diplospory function or improved function or which is capable of diplospory or improved diplospory in a plant or plant cell or crop. The chimeric polypeptide as taught herein may also have a part or parts of the amino acid sequences of SEQ ID NO:3. Further, the chimeric polypeptide as taught herein may comprise an N-terminal of one protein (e.g. obtained from *Taxaracum* or another plant species) and a middle domain and/or C-terminal domain of another protein (e.g. obtained from *Taxaracum* or another plant species). Such chimeric proteins may have improved diplospory function over the native protein or help improve the induction or may help improve diplospory in a plant or plant cell or crop.

Amino acid sequence identity may be determined by any suitable means available in the art. For instance, amino acid sequence identity may be determined by pairwise alignment using the Needleman and Wunsch algorithm and GAP default parameters as defined above. It is also understood that many methods can be used to identify, synthesize or isolate variants of the polypeptides as taught herein, such as western blot, immunohistochemistry, ELISA, amino acid synthesis, and the like.

It is also understood that any variants or fragments of the DIP polypeptides as taught herein exert the same function and/or have the same activity as the DIP polypeptide as taught herein. The functionality or activity of any DIP polypeptides or variants thereof may be determined by any known methods in the art, which the skilled person would consider suitable for these purposes.

In an embodiment, a fragment of the polypeptides (SEQ ID NO:3) or variants thereof as taught herein is capable of providing diplospory function to a plant or plant cell capable of inducing diplospory or gametophytic apomixis.

In an embodiment, fragment of the polypeptides and variants thereof as taught herein may have a length of at least 10, 20, 30, 40, 50, 100, 150, 200, 250, 300, 400, or 500 contiguous amino acids of said polypeptides.

In an embodiment, the fragment of the polypeptides and variants thereof as taught herein has the amino acid sequence of SEQ ID NO:7 and/or 12.

Methods

In a further aspect, the present invention relates to a method for producing apomictic seed, comprising the steps of:
a) transforming a plant, plant part or plant cell with any of the polynucleotides (e.g. SEQ ID NO:1 or SEQ ID NO:2) or variants or fragments thereof (e.g. SEQ ID NO: 4, 5, 6 or 11) as taught herein or the chimeric gene as taught herein or the genetic construct as taught herein and/or the nucleic acid vector as taught herein to produce a primary transformant;
b) growing a flowering plant and/or a flower from said primary transformant, whereby the polynucleotide, variant or fragment, chimeric gene, construct and/or vector as taught above is present and/or expressed at least in a female ovary, preferably in a megaspore mother cell and/or in a female gamete; and
c) pollinating said primary transformant in order to induce production of seeds, preferably with pollen of a tetraploid plant or with self pollen of said primary transformant. It is to be understood that step c) may be omitted when said primary transformant develops autonomous endosperm.

In an embodiment, the apomictic seed obtained by the method as taught herein is a clone of the primary transformant as taught herein.

In one embodiment in step (a), the plant or plant part may be transformed with a chimeric gene comprising any of the polynucleotides (e.g. SEQ ID NO:1 or SEQ ID NO:2) or variants or fragments thereof (e.g. SEQ ID NO:4 or SEQ ID NO:5) as taught herein.

In a preferred embodiment, the chimeric gene comprises SEQ ID NO:2.

In an embodiment, the chimeric gene may be comprised in a genetic construct or vector according to the invention.

In a further embodiment, the chimeric gene may also comprise an endogenous gene which has been modified. Such modification may include modification by targeted mutagenesis or the use of nucleases such as Crispr/Cas, but is not limited thereto. Said chimeric gene preferably is capable of providing diplospory function or capable of inducing diplospory or gametophytic apomixis through diplospory in a plant, plant part or plant cells when introduced in said plant, plant part or plant cells. A vector may be used to transform host cells inserting the chimeric gene in the nuclear genome or into the plastid, mitochondrial or chloroplast DNA and such that it can be expressed using a suitable promoter (e. g., Mc Bride et al., 1995 Bio/Technology 13, 362; U.S. Pat. No. 5,693,507). One advantage of plastid genome transformation is that the risk of spread of the transgene(s) can be reduced. Plastid genome transformation can be carried out as known in the art, see e.g. Sidorov V A et al. 1999, Plant J. 19: 209-216 or Lutz K A et al. 2004, Plant J. 37(6):906-13.

In one embodiment, the polynucleotide or variant or fragment as taught herein, which is comprised in a chimeric gene as taught above, is operably linked to a promoter sequence, wherein the promoter sequence comprises:
(a) the endogenous promoter sequence of the nucleic acid sequence of SEQ ID NO:1 and/or SEQ ID NO:2.;
(b) a functional fragment of said native promoter sequence;
(c) a nucleic acid sequence comprising at least 70% sequence identity with the endogenous promoter sequence of the nucleic acid sequence of SEQ ID NO:1 or SEQ ID NO:2; or
(d) a functional fragment of the nucleic acid sequence of (c);
e) the native promoter sequence of the nucleic acid sequence of SEQ ID NO:6;
f) a functional fragment of the promoter sequence of d);
g) a nucleic acid sequence comprising at least 70%, preferably at least 80%, more preferably at least 90%, most preferably at least 95% sequence identity with the native promoter sequence of the nucleic acid sequence of SEQ ID NO:6; or
h) a functional fragment of the nucleic acid sequence of g).

It is understood that, as said above, the chimeric gene according to the invention may represent a dominant allele. Hence, transforming a plant, plant part or plant cell with such a dominant chimeric gene would suffice to provide diplospory function to said plant, plant part or plant cell or to induce diplospory or gametophytic apomixis through diplospory in said plant, plant part or plant cells.

In one embodiment, polynucleotides are provided which are capable of encoding a protein (SEQ ID NO:3) or variants or fragments thereof (e.g. SEQ ID NO:7 and/or 12) as taught herein and which are capable of providing diplospory function to a plant, plant part or plant cell or to induce gametophytic apomixis through diplospory in said a plant, plant part or plant cell, as described above. Such polynucleotides may be used to make chimeric genes, and vectors comprising these for transfer of the chimeric gene into a host cell and production of the protein(s) in host cells, such as cells, tissues, organs or organisms derived from transformed cell(s). Vectors for the production of said protein (or protein fragments or variants) in plant cells are herein referred to as i.e. 'expression vectors'. Host cells are preferably plant cells.

Any plant may be a suitable host, but most preferably the host is a plant species which could benefit from enhanced or reduced diplospory. Especially cultivars or breeding lines having otherwise good agronomic characteristics are preferred. It is easy to test whether a gene and/or a protein (or variants or fragments thereof) provided herein confer the required increase of diplospory onto the host plant, by generating transgenic plants and inducing diplospory, together with suitable control plants.

In an embodiment, suitable host plants may be selected from maize/corn (*Zea* species), wheat (*Triticum* species), barley (e.g. *Hordeum vulgare*), oat (e.g. *Avena sativa*), sorghum (*Sorghum bicolor*), rye (*Secale cereale*), soybean (*Glycine* spp, e.g. *G. max*), cotton (*Gossypium* species, e.g. *G. hirsutum, G. barbadense*), *Brassica* spp. (e.g. *B. napus, B. juncea, B. oleracea, B. rapa*, etc), sunflower (*Helianthus annus*), safflower, yam, *cassava*, alfalfa (*Medicago sativa*), rice (*Oryza* species, e.g. *O. sativa* indica cultivar-group or *japonica* cultivar-group), forage grasses, pearl millet (*Pennisetum* spp. e.g. *P. glaucum*), tree species (*Pinus*, poplar, fir, plantain, etc), tea, *coffea*, oil palm, coconut, vegetable species, such as pea, zucchini, beans (e.g. *Phaseolus* species), hot pepper, cucumber, artichoke, asparagus, eggplant, broccoli, garlic, leek, lettuce, onion, radish, turnip, tomato, potato, Brussels sprouts, carrot, cauliflower, chicory, celery, spinach, endive, fennel, beet, fleshy fruit bearing plants (grapes, peaches, plums, strawberry, mango, apple, plum, cherry, apricot, banana, blackberry, blueberry, *citrus*, kiwi, figs, lemon, lime, nectarines, raspberry, watermelon, orange, grapefruit, etc.), ornamental species (e.g. Rose, *Petunia, Chrysanthemum, Lily, Gerbera* species), herbs (mint, parsley, basil, thyme, etc.), woody trees (e.g. species of *Populus, Salix, Quercus, Eucalyptus*), fibre species e.g. flax (*Linum usitatissimum*) and hemp (*Cannabis sativa*).

In a preferred embodiment, the host plant may be a plant species selected from the group consisting of the genera *Taraxacum, Lactuca, Pisum, Capsicum, Solanum, Cucumis, Zea, Gossypium, Glycine, Tryticum, Oryza* and *Sorghum*.

In an embodiment, the polynucleotides (SEQ ID NO:1 or SEQ ID NO:2), variants or fragments thereof (e.g. SEQ ID NO:4, 5, 6, or 11), which are preferably comprised in a chimeric gene according to the invention, and which are capable of encoding a protein (SEQ ID NO:3) or variant or fragments thereof (e.g. SEQ ID NO:7 and/or 12), and which are capable of providing diplospory function to a plant, plant part or plant cell or inducing diplospory or gametophytic apomixis through diplospory in a plant, plant part or plant cell, can be stably inserted in a conventional manner into the nuclear genome of a single plant cell, and the so-transformed plant cell can be used in a conventional manner to produce a transformed plant that has an altered phenotype due to the presence of the said protein in certain cells at a certain time. In this regard, a T-DNA vector, comprising polynucleotide, variants or fragments thereof as taught herein, which are capable of encoding a protein or variants or fragments as taught herein, which is capable of providing diplospory function or inducing diplospory or gametophytic apomixis through diplospory, in *Agrobacterium tumefaciens* can be used to transform the plant cell, and thereafter, a transformed plant can be regenerated from the transformed plant cell using the procedures described, for example, in EP 0 116 718, EP 0 270 822, PCT publication WO84/02913 and published European Patent application EP 0 242 246 and in Gould et al. (1991, Plant Physiol. 95, 426-434). The construction of a T-DNA vector for *Agrobacterium* mediated plant transformation is well known in the art. The T-DNA vector may be either a binary vector as described in EP 0 120

561 and EP 0 120 515 or a co-integrate vector which can integrate into the *Agrobacterium* Ti-plasmid by homologous recombination, as described in EP 0 116 718. Lettuce transformation protocols have been described in, for example, Michelmore et al., 1987 and Chupeau et al. 1989.

Preferred T-DNA vectors each contain a promoter operably linked to nucleic acid sequence function encoding a protein capable of providing diplospory (e.g. encoding SEQ ID NO:3 or variants or fragments thereof (e.g. SEQ ID NO:7 and/or 12)). The promoter being operably linked to said nucleotide sequence or sequences between T-DNA border sequences, or at least located to the left of the right border sequence. Border sequences are described in Gielen et al. (1984, EMBO J 3, 835-845). Of course, other types of vectors can be used to transform the plant cell, using procedures such as direct gene transfer (as described, for example in EP 0 223 247), pollen mediated transformation (as described, for example in EP 0 270 356 and WO85/01856), protoplast transformation as, for example, described in U.S. Pat. No. 4,684,611, plant RNA virus-mediated transformation (as described, for example in EP 0 067 553 and U.S. Pat. No. 4,407,956), liposome-mediated transformation (as described, for example in U.S. Pat. No. 4,536,475), and other methods. Introduction of the T-DNA vector into *Agrobacterium* can be carried out using known methods, such as electroporation or triparental mating.

Likewise, selection and regeneration of transformed plants from transformed cells is well known in the art. Obviously, for different species and even for different varieties or cultivars of a single species, protocols are specifically adapted for regenerating transformants at high frequency.

The plant or plant part or plant cells obtainable by the method as taught herein have an altered level of diplospory, especially transgenic plants comprising a significantly enhanced level of diplospory. Such plants can be made using different methods, as described further herein below.

The plant obtained by, or obtainable by, the methods of the invention can be used in a conventional plant breeding scheme to produce more transformed plants containing the transgene as taught herein. Single copy transformed plants can be selected, using e.g. Southern Blot analysis or PCR based methods or the Invader® Technology assay (Third Wave Technologies, Inc.). Transformed cells and plants can easily be distinguished from non-transformed ones by the presence of the chimeric gene. The sequences of the plant DNA flanking the insertion site of the transgene can also be sequenced, whereby an 'event specific' detection method can be developed, for routine use. See for example WO0141558, which describes elite event detection kits (such as PCR detection kits) based for example on the integrated sequence and the flanking (genomic) sequence.

In an embodiment, the polynucleotides, variants or fragments thereof as taught herein, which are capable of providing diplospory function to a plant, plant part or plant cell or inducing diplospory or gametophytic apomixis through diplospory in a plant, plant part or plant cell, e.g. by expression a protein, variants or fragments thereof according to the invention, which is capable of providing diplospory function or inducing gametophytic apomixis through diplospory in a plant, plant part or plant cell, is inserted in a plant cell genome so that the inserted coding sequence is downstream (i.e. 3') of, and under the control of, a promoter which can direct the expression in the plant cell. This may be preferably accomplished by inserting the chimeric gene in the plant cell genome, particularly in the nuclear or plastid (e. g. chloroplast) genome.

The nucleic acid sequence according to the invention, which is capable of providing diplospory function to a plant, or a sequence corresponding thereto, is preferably inserted into the plant genome so that the coding sequence is upstream (i.e. 5') of a suitable 3' end nontranslated region ("3'-end" or 3'UTR). Suitable 3'ends include those of the CaMV 35S gene ("3' 35S"), the nopaline synthase gene ("3' nos") (Depicker et al., 1982 J. Mol. Appl. Genetics 1, 561-573.), the octopine synthase gene ("3'ocs") (Gielen et al., 1984, EMBO J 3, 835-845) and the T-DNA gene 7 ("3' gene 7") (Velten and Schell, 1985, Nucleic Acids Research 13, 6981-6998), which act as 3'-untranslated DNA sequences in transformed plant cells, and others. In one embodiment the 3'UTR and/or 5'UTR of the *Taraxacum* allele capable of providing diplospory function, i.e. comprising SEQ ID NO:1 and/or SED ID NO:2 (or a variant or fragment thereof) is used. The 3'UTR and/or 5'UTR may also be used in another embodiment, as it may also be used in combination with other coding regions or other nucleic acid constructs.

A DIP encoding nucleic acid sequence can optionally be inserted in the plant genome as a hybrid gene sequence whereby the sequence capable of providing diplospory function to a plant is linked in-frame to a gene encoding a selectable or scorable marker (U.S. Pat. No. 5,254,799; Vaeck et al., 1987, Nature 328, 33-37), such as for example the neo (or nptII) gene (EP 0 242 236) encoding kanamycin resistance, so that the plant expresses a fusion protein which is easily detectable.

Preferably, for selection purposes but also for weed control options, the transgenic plants of the invention may also be transformed with a DNA encoding a protein conferring resistance to herbicide, such as a broad-spectrum herbicide, for example herbicides based on glufosinate ammonium as active ingredient (e.g. Liberty® or BASTA; resistance is conferred by the PAT or bar gene; see EP 0 242 236 and EP 0 242 246) or glyphosate (e.g. RoundUp®; resistance is conferred by EPSPS genes, see e.g. EP0 508 909 and EP 0 507 698). Using herbicide resistance genes (or other genes conferring a desired phenotype) as selectable marker further has the advantage that the introduction of antibiotic resistance genes can be avoided.

Alternatively, other selectable marker genes may be used, such as antibiotic resistance genes. As it may be not accepted to retain antibiotic resistance genes in transformed host plants, these genes can be removed again following selection of the transformants. Different technologies exist for removal of transgenes. One method to achieve removal is by flanking the chimeric gene with lox sites and, following selection, crossing the transformed plant with a CRE recombinase-expressing plant (see e.g. EP506763B1). Site specific recombination results in excision of the marker gene. Another site specific recombination system is the FLP/FRT system described in EP686191 and U.S. Pat. No. 5,527,695. Site specific recombination systems such as CRE/LOX and FLP/FRT may also be used for gene stacking purposes. Further, one-component excision systems have been described, see e.g. WO9737012 or WO9500555.

All or part of a nucleic acid sequence according to the invention, which is capable of providing diplospory function to a plant e.g. as it encodes a protein according to the invention, can also be used to transform microorganisms, such as bacteria (e.g. *Escherichia coli, Pseudomonas, Agrobacterium, Bacillus*, etc.), fungi, or algae or insects, or to make recombinant viruses. Transformation of bacteria, with all or part of a nucleic acid sequence of this invention, incorporated in a suitable cloning vehicle, can be carried out in a conventional manner, preferably using conventional electroporation techniques as described in Maillon et al. (1989, FEMS Microbiol. Letters 60, 205-210.) and WO 90/06999. For expression in prokaryotic host cell, the codon usage of the nucleic acid sequence may be optimized accordingly. Intron sequences should be removed and other adaptations for optimal expression may be made as known.

The DNA sequence of the nucleic acid sequence according to the invention can be further changed in a translational neutral manner, i.e. with regard to amino acid sequence, to modify possibly inhibiting DNA sequences present in the gene part and/or by introducing changes to the codon usage, e. g., adapting the codon usage to that most preferred by plants, preferably the specific relevant plant genus, as described above.

As said, according to an embodiment of this invention, the proteins according to the invention, or chimeric proteins, which are capable of providing diplospory function to a plant are targeted to intracellular organelles such as plastids, preferably chloroplasts, mitochondria, and may also be secreted from the cell, potentially optimizing protein stability and/or expression. Similarly, the protein may be targeted to vacuoles. For this purpose, in one embodiment of this invention, the chimeric genes of the invention comprise a coding region encoding a signal or target peptide, linked to the protein coding region according to the invention. Particularly preferred peptides to be included in the proteins of this invention are the transit peptides for chloroplast or other plastid targeting, especially duplicated transit peptide regions from plant genes whose gene product is targeted to the plastids, the optimized transit peptide of Capellades et al. (U.S. Pat. No. 5,635,618), the transit peptide of ferredoxin-NADP+oxidoreductase from spinach (Oelmuller et al., 1993, Mol. Gen. Genet. 237, 261-272), the transit peptide described in Wong et al. (1992, Plant Molec. Biol. 20, 81-93) and the targeting peptides in published PCT patent application WO 00/26371. Also preferred are peptides signalling secretion of a protein linked to such peptide outside the cell, such as the secretion signal of the potato proteinase inhibitor II (Keil et al., 1986, Nucl. Acids Res. 14, 5641-5650), the secretion signal of the alpha-amylase 3 gene of rice (Sutliff et al., 1991, Plant Molec. Biol. 16, 579-591) and the secretion signal of tobacco PR1 protein (Cornelissen et al., 1986, EMBO J. 5, 37-40). Particularly useful signal peptides in accordance with the invention include the chloroplast transit peptide (e.g. Van Den Broeck et al., 1985, Nature 313, 358), or the optimized chloroplast transit peptide of U.S. Pat. No. 5,510,471 and U.S. Pat. No. 5,635,618 causing transport of the protein to the chloroplasts. Also a secretory signal peptide or a peptide targeting the protein to other plastids, mitochondria, the ER, or another organelle can be used. Signal sequences for targeting to intracellular organelles or for secretion outside the plant cell or to the cell wall are found in naturally targeted or secreted proteins, preferably those described by Klösgen et al. (1989, Mol. Gen. Genet. 217, 155-161), Klösgen and Weil (1991, Mol. Gen. Genet. 225, 297-304), Neuhaus & Rogers (1998, Plant Mol. Biol. 38, 127-144), Bih et al. (1999, J. Biol. Chem. 274, 22884-22894), Morris et al. (1999, Biochem. Biophys. Res. Commun. 255, 328-333), Hesse et al. (1989, EMBO J. 8, 2453-2461), Tavladoraki et al. (1998, FEBS Lett. 426, 62-66.), Terashima et al. (1999, Appl. Microbiol. Biotechnol. 52, 516-523), Park et al. (1997, J. Biol. Chem. 272, 6876-6881), Shcherban et al. (1995, Proc. Natl. Acad. Sci USA 92, 9245-9249).

In one embodiment, several protein encoding nucleic acid sequences according to the invention, which are capable of providing diplospory function to a plant, are co-expressed in a single host, optionally under control of different promoters. A co-expressing host plant is easily obtained by transforming a plant already expressing a protein of this invention, or by crossing plants transformed with different proteins of this invention. Hence, the invention also provides for plants or plant parts having multiple nucleic acid sequences of the same or different isolated nucleic acid sequences of the invention, of which each may be capable of providing diplospory function to a plant. It is understood that the term multiple in this respect means per cell. Alternatively, several nucleic acid sequences according to the invention, each of which may be capable of providing diplospory function to a plant, may be present on a single transformation vector or be co-transformed at the same time using separate vectors and selecting transformants comprising multiple chimeric genes. Similarly, one or more genes encoding a protein capable of providing diplospory function according to the invention may be expressed in a single plant together with other chimeric genes, for example encoding other proteins which enhance or suppress diplospory, or that are involved in apomixis. It is understood that the different proteins can be expressed in the same plant, or each can be expressed in a single plant and then combined in the same plant by crossing the single plants with one another. For example, in hybrid seed production, each parent plant can express a single protein. Upon crossing the parent plants to produce hybrids, both proteins are combined in the hybrid plant.

It is also an embodiment to generate plants which several chimeric genes according to the invention, preferably under the control of different promoters. This way, enhancement or suppression of the diplospory phenotype can be fine-tuned by expressing a suitable amount of a protein according to the invention which is capable of providing diplospory function to a plant, at a suitable time and location. Such fine-tuning may be done by determining the most appropriate promoter and/or by selecting transformation "events" which show the desired expression level.

Transformants expressing desired levels of a protein according to the invention capable of providing diplospory function are selected by e.g. analysing copy number (Southern blot analysis), mRNA transcript levels (e.g. RT-PCR using primer pairs or flanking primers) or by analysing the presence and level of said diplospory protein in various tissues (e.g. SDS-PAGE; ELISA assays, etc). For regulatory reasons, preferably single copy transformants are selected and the sequences flanking the site of insertion of the chimeric gene is analysed, preferably sequenced, to characterize the result of the transformation. High or moderate DIP expressing transgenic events are selected for further development until a high performing elite event with a stable Dip transgene is obtained.

Also, it is envisaged that plants having several chimeric genes may have a first chimeric gene encoding a protein capable of providing diplospory function, and a second chimeric gene capable of suppressing or silencing the first chimeric gene. Said second chimeric gene preferably is under control of an inducible promoter. Such a plant may be particularly advantageous, as it allows to control the diplospory function. By inducing expression from said promoter, diplospory function in a plant may be lost. Furthermore, such control may also be obtained or is obtainable by introducing in a diplospory plant, a chimeric gene according to the invention which is also capable of suppressing or silencing the endogenous gene that provides diplospory function to the plant, i.e. which naturally encodes an amino acid sequence according to the invention.

By selecting conserved nucleic acid sequence parts of the nucleic acid sequence according to the invention, an allele in a host plant or plant parts can be silenced. Said silencing may result, as described above, in the suppression of diplospory function of a plant. Hence, encompassed herein are also plants comprising a chimeric gene which includes a transcription regulatory element operably linked to a sense and/or antisense DNA fragment of a nucleic acid sequence according to the invention and which is capable of exhibiting suppressed or enhanced diplospory. Said transcription regulatory element may be a suitable promoter, which may be an inducible promoter.

Transformed plants expressing one or more proteins capable of providing diplospory function to a plant according to the invention may also comprise other transgenes, such as genes conferring disease resistance or conferring tolerance to other biotic and/or abiotic stresses. To obtain such plants with "stacked" transgenes, other transgenes may either be introduced into the transformed plants, or the transformed plants may be transformed subsequently with one or more other genes, or alternatively several chimeric genes may be used to transform a plant line or variety. For example, several chimeric genes may be present on a single vector, or may be present on different vectors which are co-transformed.

In one embodiment the following genes are combined with one or more chimeric genes according to the invention: known disease resistance genes, especially genes conferring enhanced resistance to necrotrophic pathogens, virus resistance genes, insect resistance genes, abiotic stress resistance genes (e.g. drought tolerance, salt tolerance, heat- or cold tolerance, etc.), herbicide resistance genes, and the like. The stacked transformants may thus have an even broader biotic and/or abiotic stress tolerance, to pathogen resistance, insect resistance, nematode resistance, salinity, cold stress, heat stress, water stress, etc. Also, as described above, in this embodiment silencing or suppression of diplospory function approaches may be combined with gene expression approaches in a single plant.

It is understood that the plants or plants parts comprising a chimeric gene according to the invention preferably do not show non-desired phenotypes, such as yield reduction, enhanced susceptibility to diseases (especially to necrotrophs) or undesired architectural changes (dwarfing, deformations) etc. and that, if such phenotypes are seen in the primary transformed plants, these can be removed by conventional methods. Any of the plants described herein may be homozygous or hemizygous for the chimeric gene according to the invention.

In a further aspect, the present invention relates to a method for producing clones of a hybrid plant, comprising the steps of:
a) cross-fertilizing a sexually reproducing plant with pollen of a plant as taught herein to produce F1 hybrid seed;
b) selecting F1 plants that comprise and/or express the polynucleotides or variants or fragments thereof as taught herein or a polypeptide or variants or fragments thereof as taught herein at least in a female ovary, preferably in a megaspore mother cell and/or in a female gamete;
c) optionally, pollinating said selected F1 plants in order to induce production of seeds, preferably with pollen of a tetraploid plant; and
d) harvesting seed; and
e) optionally, growing a hybrid clone plant from said seed.

Step c) may be omitted when the selected F1 plants develop autonomous endosperm.

In an embodiment, the clone of step (e) of the method as taught herein is an apomictic clone.

In an embodiment, the method as taught herein comprises obtaining said hybrid plant.

In a further aspect, the present invention relates to a method for conferring diplospory to a plant, plant part or plant cell or for inducing gametophytic apomixis through diplospory in a pant, plant part or plant cell, comprising the steps of:
a) transforming said plant, plant part or plant cell with any of the polynucleotides, variants or fragments thereof as taught herein, the chimeric gene as taught herein, the genetic construct as taught herein, and/or the nucleic acid vector as taught herein; and
b) optionally regenerating a plant, whereby said polynucleotide, variant or fragment, gene, construct and/or vector is present and/or expressed at least in a female ovary, preferably in a megaspore mother cell and/or in a female gamete.

In an embodiment, the polynucleotides, variants or fragments thereof as taught herein are integrated into the genome of said plant, plant part or plant cell.

In an embodiment, the method as taught herein comprises obtaining a diplosporous plant.

In a further aspect, the present invention relates to a method for conferring diplospory on, or inducing diplospory in, a plant, plant part or plant cell or for inducing gametophytic apomixis through diplospory in a pant, plant part or plant cell, comprising the steps of:
a) modifying an endogenous polynucleotide, variant or a fragment of a polynucleotide, preferably of a Vacuolar Protein Sorting-associated protein gene, in the plant, plant part or plant cell such that after modification the plant, plant part or plant cell comprises any one of the polynucleotide, variant or fragments thereof as taught herein; and
b) optionally regenerating a plant.

In an embodiment, the modified polynucleotide, variants or fragment of a polynucleotide of step (a) of the method as taught herein is expressed and/or encodes a polypeptide.

In an embodiment, the modified polynucleotide or fragment of a polynucleotide of step (a) of the method as taught herein is present at least in a female ovary, preferably in a megaspore mother cell and/or in a female gamete.

In an embodiment, the modification of step (a) of the method as taught herein is performed by:
a) introducing or expressing at least one site-specific nuclease in said plant, plant part or plant cell, preferably wherein said nuclease is selected from the group consisting of Cas9/RNA CRISPR nuclease, zinc-finger nuclease, meganuclease, and TAL-effector nuclease; and/or by
b) oligonucleotide-directed mutagenesis using an oligonucleotide, preferably wherein the oligonucleotide is a single-stranded oligonucleotide; and/or by
c) chemical mutagenesis, preferably with ethyl methanesulfonate.

In an embodiment, the method as taught herein comprises obtaining a diplosporous plant.

In an embodiment, said modification, particularly in *Taraxacum*, comprises the deletion of nucleotides encoding amino acid residues GGGGW (SEQ ID NO: 14) corresponding to position 96-100 of the endogenous dip amino acid sequence as set forth in SEQ ID NO: 10 and/or the deletion of nucleotides encoding residues PPT corresponding to position 108-110 of the endogenous dip amino acid sequence as set forth in SEQ ID NO:10. In other organisms, nucleotides encoding amino acid residues corresponding to amino acid residues GGGGW (SEQ ID NO: 14) or PPT as found in *Taraxacum officinale* may be deleted. The skilled person will be capable of identifying the correct amino acid residues to be deleted as well as the corresponding nucleotide sequences that encode these amino acid residues.

In an embodiment, said modification comprises one or more, e.g. all, of the differences between dip (sexual allele; SEQ ID NO:13) and Dip (diplosporous allele) nucleotide sequences as set forth in FIG. 2.

In an embodiment, whole plants, seeds, cells, tissues and progeny of any of the transformed plants obtainable by the methods as taught herein are encompassed herein and can be identified by detecting the presence of the chimeric gene, genetic construct or vector as taught herein in the DNA, for example by PCR analysis using total genomic DNA as template and using specific PCR primer pairs, e.g. specific primer pairs designed against sequences SEQ ID NO:1 and/or SEQ ID NO:2 and/or SEQ ID NO:4, 6 or 11, or variants thereof such as described above. Also 'event specific' PCR diagnostic methods can be developed, where the PCR primers are based on the plant DNA flanking the inserted chimeric gene, see U.S. Pat. No. 6,563,026. Similarly, event specific AFLP fingerprints or RFLP fingerprints may be developed which identify the transformed or modified plant or any plant, seed, tissue or cells derived there from.

Plants and Seeds

In a further aspect, the present invention relates to a plant, plant part or plant cell comprising the chimeric gene as taught herein, the genetic construct as taught herein, and/or the nucleic acid vector as taught herein, whereby the gene, construct and/or vector is present and/or expressed at least in a female ovary, preferably in a megaspore mother cell and/or in a female gamete.

In an embodiment, the seeds of the plant as taught herein are apomictic seeds.

In an embodiment, the seed as taught herein is a clone of the plant as taught herein on which it developed.

In a preferred embodiment, the plant, plant part, plant cell or seed as taught herein is from a species selected from the group consisting of the genera *Taraxacum, Lactuca, Pisum, Capsicum, Solanum, Cucumis, Zea, Gossypium, Glycine, Triticum, Oryza, Allium, Brassica, Helianthus, Beta, Cichorium, Chrysanthemum, Pennisetum, Secale, Hordeum, Medicago, Phaseolus, Rosa, Lilium, Coffea, Linum, Canabis, Cassava, Daucus, Cucurbita, Citrullus,* and *Sorghum*.

Uses

In a further aspect, the present invention relates to uses of any of the isolated polynucleotides, variants or fragments thereof as taught herein for inducing diplospory in plants.

In a further aspect, the present invention relates to uses of any of the isolated polynucleotides or fragments or variants thereof as taught herein for prevention of the segregation of multiple genes, QTLs or transgenes.

In a further aspect, the present invention relates to uses of any of the isolated polynucleotides or fragments or variants thereof as taught herein for stacking of genes.

In a further aspect, the present invention relates to uses of any of the isolated polynucleotides or fragments or variants thereof as taught herein for development and/or identification of markers for the diplospory trait.

In an embodiment, the polynucleotides (SEQ ID NO:1 or SEQ ID NO:2), variants or fragments thereof (e.g. SEQ ID NO:4, 5, 6, or 11) as taught herein, which are capable of encoding the protein (SEQ ID NO:3) or variants or fragments thereof (e.g. SEQ ID NOs:7 and/or 12) as taught herein, and also polynucleotide sequences encoding any proteins and variants thereof capable of providing diplospory function or inducing diplospory or gametophytic apomixis through diplospory in a plant, may be used as genetic markers for marker assisted selection of the alleles capable of providing diplospory function of *Taraxacum* species (and/or of other plant species) and for the transfer and/or combination of different or identical diplospory alleles to/in plants of interest and/or to/in plants which can be used to generate intraspecific or interspecific hybrids with the plant in which the diplospory allele (or variant) is found.

A large variety of different marker assays can be developed based on these sequences. The development of a marker assay generally involves the identification of polymorphisms between alleles, so that the polymorphism is a genetic marker which "marks" a specific allele. The polymorphism(s) is/are then used in a marker assay. For example the nucleic acid sequences of SEQ ID NO:1 and/or SEQ ID NO:2 and/or SEQ ID NO:4, 5, 6, or 11, or variants thereof according to the invention may be correlated with the presence, absence, reduction, suppression or enhancement of diplospory. This is for example done by screening diplosporous plant material and/or non-diplosporous plant material for one or more of such sequences in order to correlate specific alleles with absence or presence of diplospory function. Thus, PCR primers or probes may be generated which detect the presence or absence SEQ ID NO:1 and/or SEQ ID NO:2 and/or SEQ ID NO:4, 5, 6, or 11 or variants or fragments thereof in a sample (e.g. an RNA, cDNA or genomic DNA sample) obtained from plant material. The sequences or parts thereof are compared and polymorphic markers may be identified which may correlate with diplospory. A polymorphic marker, such as a SNP marker linked to a Dip or dip allele can then be developed into a rapid molecular assay for screening plant material for the presence or absence of the diplospory allele. Thus, the presence or absence of these "genetic markers" is indicative of the presence of the Dip allele linked thereto and one can replace the detection of the Dip allele with the detection of the genetic marker. Example of such markers are disclose in the Examples section.

Preferably, easy and fast marker assays are used, which enable the rapid detection of specific Dip or dip alleles (e.g. of an allele which confers diplospory, such as Dip, versus an allele which does not, such as for instance dip) or allele combinations in samples (e.g. DNA samples). Thus, in one embodiment the use is provided of the nucleic acid sequences of SEQ ID NO:1 and/or SEQ ID NO:2, or variants or fragments thereof (SEQ ID NO:4 or SEQ ID NO:5, 6 or 11) thereof comprising at least 70%, 80%, 90%, 95%, 98%, 99% or more nucleic acid identity therewith, or one or more fragments thereof, in a molecular assay for determining the presence or absence of a Dip allele and/or a dip allele in the sample and/or whether the sample is homozygous or heterozygous with regard to said allele.

Such an assay may for example involve the following steps:
(a) providing diplospory and non-diplospory plant material and/or nucleic acid samples thereof;
(b) determining nucleotide sequences derived from the Vps13 gene, e.g. including sequences corresponding to SEQ ID NO:1 and/or SEQ ID NO:2 or variants and/or fragments thereof (SEQ ID NO:4, 5, 6, or 11), in the material from (a) in order to identify polymorphisms between the nucleotide sequences;

(c) correlating polymorphisms with the diplosporous characteristics of the plant, thereby correlating polymorphisms with diplospory and non-diplospory alleles of the Dip locus;

The correlated polymorphisms identified may be optionally further used in a step (d)

(d) using said polymorphic markers to develop a marker assay for use in germplasm screening or characterization and MAS.

Thus, in one embodiment of the invention PCR primers and/or probes, molecular markers and kits for detecting DNA or RNA sequences derived from alleles of the diplosporous gene are provided (i.e. Dip and/or dip allele). Degenerate or specific PCR primer pairs which may amplify Dip and/or dip DNA (such as a nucleic acid sequence from SEQ ID NO:1 and/or SEQ ID NO:2 or variants or fragments thereof (e.g., SEQ ID NO:4, 5, 6, or 11) from samples can be synthesized based on said sequences (or variants thereof) which is well known in the art (see Dieffenbach and Dveksler (1995) PCR Primer: A Laboratory Manual, Cold Spring Harbor Laboratory Press, and McPherson at al. (2000) PCR-Basics: From Background to Bench, First Edition, Springer Verlag, Germany). For example, any stretch of 9, 10, 11, 12, 13, 14, 15, 16, 18 or more contiguous nucleotides of those sequences (or the complement strand) may be used as primer or probe. The polynucleotide sequences of the invention can be used as hybridization probes as well. A Dip gene/allele detection kit may comprise Dip and/or dip allele specific primers and/or Dip and/or dip allele specific probes. An associated protocol may be used for the primers and/or probe to detect Dip and/or dip DNA in a sample. Such a detection kit may, for example, be used to determine, whether a plant has been transformed with an Dip gene (or part or variant thereof) of the invention or to screen *Taraxacum* germplasm and/or other plant species germplasm for the presence of Dip alleles (or Dip homologs or orthologs) and optionally zygosity determination.

In one embodiment therefore a method of detecting the presence or absence of a nucleotide sequence encoding an DIP protein in a plant tissue, e.g. in *Taraxacum* tissue, or a nucleic acid sample thereof is provided. The method comprises:

a) obtaining a plant tissue sample, e.g. a *Taraxacum* tissue sample, or nucleic acid sample thereof, b) analyzing the nucleic acid sample using a molecular marker assay for the presence or absence of one or more markers linked to an Dip allele, wherein the marker assay detects any one of SEQ ID NO:1 and/or SEQ ID NO: 2 and/or SEQ ID NO:4, 5, 6, or 11, or a sequence comprising at least 70% nucleotide identity therewith in said sample, and optionally c) selecting the plant (e.g. the *Taraxacum* plant) comprising one or more of said markers.

Further Applications of Diplospory

Diplospory is an element of apomixis and a gene for diplospory may be used in combination with a gene for parthenogenesis to generate apomixis and to use it for the applications listed above. These genes can be introduced into sexual crops by transformation. Knowledge of the structure and function of the apomixis genes can also be used to modify endogenous sexual reproduction genes in such a way that they become apomixis genes. The preferred use would be to bring the apomixis genes under a inducible promoter such that apomixis can be switched off when sexual reproduction generates new genotypes and switched on when apomixis is needed to propagate the elite genotypes.

However, a diplospory polynucleotide or gene of the invention could also be used in entirely new ways, not directly as an element of apomixis. A diplospory gene could be used for sexual polyploidization, to generate polyploid offspring from diploid plants. Polyploid plants often are heterotic and produce higher yields than diploid plants (Bingham, E. T., R. W. Groose, D. R. Woodfield & K. K. Kidwell, 1994. Complementary gene interactions in alfalfa are greater in autopolyploids than diploids. Crop Sci 34: 823-829.; Mendiburu, A. O. & S. J. Peloquin, 1971. High yielding tetraploids from 4×-2× and 2×-2× matings. Amer Potato J 48: 300-301). The Dip gene, i.e. a gene (or chimeric gene, or vector or genetic construct) capable of providing diplospory function to a plant according to the invention, avoids female Meiosis I, and therefore generates First Division Restitution (FDR) egg cells, which transfer the full maternal genome, including all heterozygosity and epistatic gene interactions (Mok, D. W. S. and S. J. Peloquin. 1972. Three mechanisms of 2n pollen formation in. diploid potatoes. Am. Potato J. 49:362-363.; Ramanna, M. S., 1979. A re-examination of the mechanisms of 2n gamete formation in potato and its implications for breeding. Euphytica 28: 537-561). Offspring produced by FDR gametes is superior to offspring produced by Second Division Restitution (SDR) gametes, which transfer only a part of the parental heterozygosity and epistasis to the offspring. Both FDR and SDR types of unreduced gametes result in hybrid offspring after crossing, with a much increased heterozygosity compared to somatic polyploidization by chemical treatment (e.g. colchicine). Therefore FDR gametes, like the ones induced by the Dip-gene, are the most preferred type of gametes for sexual polyploidization. FDR gametes have proven their use for the improvement of autopolyploid crops such as potato, alfalfa, *Vaccinium* spp., and some of the fodder grasses (Ramanna, M. S. and Jacobsen E. 2003. Relevance of sexual polyploidization for crop improvement—a review. Euphytica 133:3-8; Mariani, A. & S. Tavoletti, 1992. Gametes with Somatic Chromosome Number in the Evolution and Breeding of Polyploid Polysomic Species. Proc Workshop, Perugia, Tipolithographia Porziuncola-Assisi (PG) Italy, pp. 1-103; Veilleux, R., 1985. Diploid and polyploid gametes in crop plants: Mechanisms of formation and utilization in plant breeding. Plant Breed Rev 3: 252-288). In these applications it is highly beneficial that the Dip gene is only expressed during female megasporogenesis and that male meiosis is reductional. This allows the introgression of the Dip-gene into the diploid gene pool through reduced pollen grains, creating new beneficial gene combinations by crosses. Another very useful property of the Dip-gene for plant breeding is its dominance such that heterozygotes express the diplosporous phenotype. This significantly simplifies the use of the Dip-gene in breeding schemes.

One specific application of sexual polyploidization is the production of triploids which can be used to produce seedless fruits. Triploids can also function as a source for trisomics, which are very useful for mapping studies.

Whereas in apomixis both diplospory and parthenogenesis are combined in a single plant, the use of diplospory in one generation and the use of parthenogenesis in the next generation would link sexual gene pools of a crop at the diploid and at the polyploid level, by going up in ploidy level by apomeiosis and going down in ploidy level by parthenogenesis. This is very practical because polyploid populations may be better for mutation induction because they can tolerate more mutations. Polyploid plants can also be more vigorous. However diploid populations are better for selection and diploid crosses are better for genetic mapping, the construction of BAC libraries etc. Parthenogenesis in polyploids generates di-haploids which can be crossed with diploids. Diplospory in diploids generates unreduced FDR egg cells which can be fertilized by pollen from polyploids to produce polyploid offspring. Thus, an alternation of diplospory and parthenogenesis in different breeding generations links the diploid and the polyploid gene pools.

The following non-limiting Examples illustrate the different embodiments of the invention. Unless stated otherwise in the Examples, all recombinant DNA techniques are carried out according to standard protocols as described e.g. in Sambrook et al. (1989) Molecular Cloning: A Laboratory Manual, Second Edition, Cold Spring Harbor Laboratory Press, and Sambrook and Russell (2001) Molecular Cloning: A Laboratory Manual, Third Edition, Cold Spring Harbor Laboratory Press, NY; and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Croy, jointly published by BIOS Scientific Publications Ltd (UK) and Blackwell Scientific Publications, UK.

EXAMPLES

Example 1. Genetic Mapping of the DIP Locus 1.1 Apomixis Recombination Population For the genetic mapping of the Diplosporous (Dip) locus, a cross was made between a diploid sexual *Taraxacum officinale* plant TJX3-20 and a triploid apomict A68. TJX3-20 was chosen as a male sterile (no pollen production) seed parent in order to prevent the production of a high proportion of selfed offspring, which is normally the case in diploid X triploid *Taraxacum officinale* crosses, as a consequence of mentor pollen effects (Tas en Van Dijk 1999). Average seed set in the TJX3-20×A68 cross was low, between 1-3%. A large number of crosses resulted in a total of 190 offspring. Only viable euploid offspring was produced: 97 diploids, 92 triploids and 1 tetraploid (ploidy level was determined with a PARTEC flow cytometer, Van Dijk et al. 2003). None of the diploids was apomictic, in contrast to the triploids which segregated for apomixis/no apomixis.

1.2 Diplospory Phenotyping

In order to map the DIP locus genetically, the triploid progeny plants were phenotyped for diplosporous versus non-diplosporous (meiotic). The triploid progeny plants that produced triploid seeds without cross pollination, were apomictic and thus also diplosporous, For diplospory phenotyping of non-apomictic plants so called pseudo-test crosses were made (Ozias Akins and Van Dijk 2007). Triploid offspring from the TJX3-20×A68 cross was crossed with diploid sexual pollen donors. Seeds were harvested and germinated and the ploidy level of the progeny was determined by flow cytometry (Partec Ploidy Analyser, van Dijk et al. 2003). If the progeny consisted solely of tetraploid plants, it was concluded by subtraction that the triploid mother plant had been diplosporous, since the diploid pollen donor produced haploid pollen grains. If the progeny consisted of plants with a triploid or lower ploidy level, it was concluded that the egg cells of the mother plants had a reduced chromosome number and that the mother plant itself was non-diplosporous.

1.3 a Genetic Map of the DIP Chromosomal Region

Single dose dominant markers (simplex e.g. 001) can be mapped in autopolyploid plants according to the method described in Wu et al. (1992). Seven AFLP (Vos et al. 1995) markers that were closely linked to the Dip locus (from Vijverberg et al 2004) were mapped in 76 triploid progeny plants from TJX3-20×A68 cross: (for AFLP primer code, see Table 1) E40M60-505 (505 indicates the size of the fragment in base pairs; short code: S4), E38M48-215 (S8), E42M50-440 (S7), E35M52-235 (S10), E38M48-215 (S9), E45M53-090 (A4) and E37M59-135 (A5). To position the Dip locus, the triploid progeny plants were phenotyped for diplospory using the pseudo-test cross method, described above. Table 2 indicates the genotypes of four triploid progeny plants (AS99, AS112, AS193 and AS196) with a recombination event in the DIP chromosomal region.

EcoRI

TABLE 1

Selective nucleotides of the used AFLP primers.

| | Selective nucleotides |
|---|---|
| EcoRI | |
| E35 | ACT |
| E37 | ACG |
| E38 | ACT |
| E40 | AGC |
| E42 | AGT |
| E43 | ATA |
| E45 | ATG |
| E49 | CAG |
| E60 | CTC |
| MseI | |
| M40 | AGC |
| M42 | AGT |
| M48 | CAC |
| M50 | CAT |
| M52 | CCC |
| M53 | CCG |
| M59 | CTA |
| M60 | CTC |

TABLE 2

Recombination (TJX320 × A68) and deletion (A68_i124) marker map of the Dip region.

| | Plant | | | | |
|---|---|---|---|---|---|
| Marker/gene | AS196 | AS99 | AS112 | AS193 | I124 deletion |
| S4 | + | − | − | − | + |
| S8 | + | − | − | − | + |
| S7 | + | − | − | − | + |
| S10 | + | + | − | − | + |
| S9 | + | + | − | − | − |
| DD1 | − | + | − | − | − |
| DD2 | − | + | − | − | − |
| DD3 | − | + | − | − | − |
| Dip | − | + | − | − | − |
| A4 | − | + | + | − | − |
| A5 | − | + | + | + | + |

(+) sign means marker present;
(−) sign means marker absent.

Example 2. Deletion Mapping of the DIP Locus 2.1 Apomixis Deletion Population

Because seed set in the TJX3-20×A68 cross was too low to generate the thousands of seeds needed for genetic fine mapping, an alternative method was needed. Therefore a deletion mapping approach was used for the fine mapping of this chromosomal region. Gamma irradiation causes random deletions of variable size, throughout the genome, irrespective of recombination hot or cold spots. Gamma irradiation deletions have been successfully used to map apomixis genes in *Hieracium* species (Catanach A S, Erasmuson S K, Podivinsky E, Jordan B R, Bicknell R A (2006) Deletion mapping of genetic regions associated with apomixis in *Hieracium*. Proc Natl Acad Sci USA 103(49): 18650-18655). First the optimal dose of gamma irradiation for clone A68 (50% seedling survival) was determined in a series of test doses, ranging from 100 to 800 Gray produced by a 60Co source (at Isotron B. V., Ede, The Netherlands) exposing dry *Taraxacum* seeds. For the final experiment 3×2000 seeds were irradiated with three different doses: one third with 250 Gy, one third with 300 Gy and one third with 400 Gy. Seeds were put to germinate on wet filter paper in petri dishes at room temperature. In total 3075 plants were grown in pots in the greenhouse (350 of 200 Gy, 1600 of 300 Gy and 1125 of 400 Gy treatment). The plants were grown for two months in a heated greenhouse (21° C. day, 16 hrs light and 18° C. at night). Next, plants were kept for two month at 2-10° C. in order to induce flowering. After this vernalization period, the plants were again grown in the heated greenhouse at the conditions indicate above. Over 90 percent of the plants flowered and produced seeds. Plants were classified whether or not they showed a Loss-of-Apomixis phenotype (LoA). Apomictic A68 plants produce seeds spontaneously and form large white seed heads, with a dark brown center, where the seeds (in botanical terms achenes: one-seeded fruits) are attached to the receptacle (see FIG. 1A).

In the case of Loss-of-Apomixis phenotypes the center of the seed head was lighter and often the seed heads are reduced in diameter, because the seeds do not develop properly. More than 13000 seed heads were screened for Loss-of-Apomixis phenotype. Finally 102 plants were identified as Loss-of-Apomixis phenotypes. Most of these plants produced both Loss-of-Apomixis and Apomixis seed heads, indicating that they were chimaeras. This is due to the fact that the shoot meristems of the irradiated seeds were multicellular (M1 generation).

2.2 Loss-of-Diplospory Phenotyping

Figure 1B:
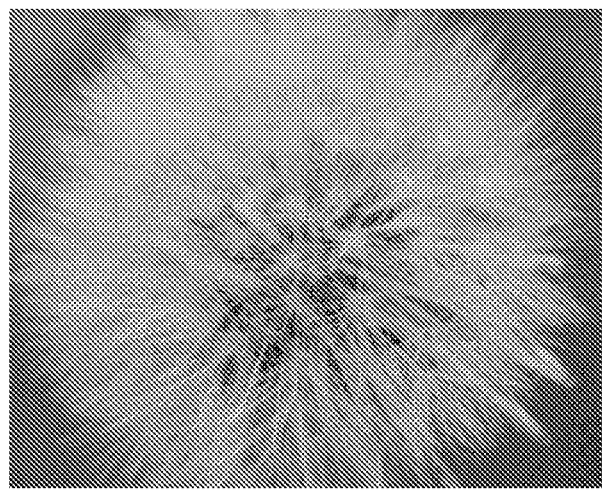
FIG. 1B. Typical seed head of a Loss of Diplospory (LoD) deletion mutant of A68, in the absence of cross-pollination. Typically LoD mutants under these conditions have smaller seed heads than A68 wildtype. Note the speckled center, with many white non-developing seeds, without the Parthenogenesis gene and a few developing seeds, with the Parthenogenesis gene. Parthenogenesis is a gametophytically expressed gene and therefore segregates when diplospory is lost and is replaced by meiosis.

Loss-of-Apomixis in irradiated plants could be due to Loss-of-Diplospory, Loss-of-Parthenogenesis or to other causes. Loss-of-Diplospory among Loss-of-Apomixis plants were detected by pseudo-test crosses (see above). Loss-of-Diplospory plants also produced spontaneously (thus without any cross pollination; see FIG. 1B) low numbers of triploid and hypo-triploid offspring, because these non-Dip plants had retained the parthenogenesis phenotype. Since parthenogenesis is gametophytically expressed, it segregates in the egg cells of non-diplosporous plants.

2.3 Low Resolution Deletion Mapping

When a part of one of the three homologous chromosomes is deleted, the single dose AFLP/SCAR markers located in the deleted region will be lost. In order to determine which of the 102 Loss-of Apomixis plants had lost parts of the Dip locus, the presence/absence of the following Dip-linked single dose markers was investigated: S8, S7, S9, S10, A4 and A5.

In total 23 Loss-of-Apomixis plants had lost two or more of these markers. Most of these plants could also be phenotyped as Loss-of-Diplospory, confirming that the Dip-gene was lost by the deletion. The number of lost markers is an indication of the size of the deletion (Catanach et al 2006). Plant i124 had retained all these markers, except S9 and A4, suggesting that this plant had the smallest deletion in the Dip-locus. The five plants with the smallest deletions (including i124) were made non-chimeric through tissue culture. Leaves were sterilized and explants were grown in vitro to regenerate whole plants. AFLP analysis confirmed that these plants were homogeneous and still carried the DIP deletions.

Example 3. DNA Sequencing of the DIP Locus 3.1 Fine Mapping of the DIP Locus Using AFLP Markers in the Deletion Population In order to find new AFLP markers within the smallest Dip-deletion detected (i124), a new marker screening strategy, Bulked Deletion Analysis (BDA), analogous to Bulked Segregation Analysis (Michelmore et al. 1991), was developed. Three DNA samples were compared for the presence or absence of AFLP fragments: Sample A: DNA from the plant with the smallest Dip deletion (i124), Sample B: A DNA pool of three plants with larger deletions in the Dip region, and Sample C: DNA from the A68 clone, non-irradiated. Only AFLPs which lacked in both sample A and sample B would be located in the smallest deletion. Taking pooled sample B into consideration prevented the selection of deletions outside the Dip locus. Candidate AFLPs from the BDA were verified on individual Loss-of-Diplospory deletion plants. Screening of 966 different AFLP primer combinations resulted into three new Dip Deletion markers (DD1: E43M40-68, DD2: E49M42-215 and DD3: E60M42-76), located within the Dip deletion of plant i124. Based on the number of AFLP markers screened with 966 AFLP primer combinations and the three markers lost, the size of the Dip deletion in plant i124 was estimated to be less than 450 kb. The DD2 marker was successfully cloned and sequenced (SEQ ID NO:12).

3.2 Gene Isolation by BAC Landing and Walking

For the construction of a complete physical BAC contig of the Dip-locus of apomictic clone A68, a BAC library was screened. A BAC library of A68 was constructed by the Arizona Genome Institute and can be obtained through the AGI website (http://www.genome.arizona.edu/orders/) as TO_Ba. This BAC library has an average insert size of 113 kb covering 10 genome equivalents (*Taraxacum* Genome Size: 835 Mb/1 C). It was constructed in the HindIII site of the pAGIBAC1 vector and contains 73728 clones. The BAC insert library was double spotted on four nylon filters. DNAs from clones in the BAC library were also pooled (192 super pools: plate pools of 384 BACs; each plate was also pooled in 4 pools of 96 BAC DNA's). The BAC insert library was screened for BACs containing the S10, A4, DD1, DD2 and DD3 markers by AFLP analysis of the pooled BAC DNA's. The BAC library was also screened by overgo hybridization of the nylon filters, using the DD2 sequence (SEQ ID NO:12) (Ross et al. 1999). For each marker one BAC insert was selected which was entirely sequenced using the GS-FLX sequence technology. By using the ends of the seed-BACs to develop new overgo probes, it is possible to extend the BAC contig (BAC walking).

In addition to BAC walking a physical map of the A68 BAC library was made using sequence based tags (Whole Genome Profiling—Van Oeveren et al 2011). BAC walking and WGP mapping gave consistent BAC contigs for the DIP region. A minimal BAC tiling path was constructed based on the shared WGP tags, using the Finger Printed Contig (FPC) software. The Minimal Tiling Path BACs were sequenced using GS FLX technology. Newbler software was used to assemble the individual 454 reads. In most cases two BAC variants were found, between which sequence identity varied between 95-99%. These variants were interpreted as different alleles or haplotypes. The presence of the DD2 marker (SEQ ID NO:12) distinguished between the Dip and the dip BAC minimal tiling path.

3.3 Mapping of the Deletion Break Points on the BAC Minimal Tiling Path

To map the deletion breakpoints and to be sure that the minimal tiling path covered the smallest Dip deletion in i124, PCR primers were designed for one gene per BAC sequence. Genes were PCR amplified and DNA was directly Sanger sequenced on the ABI 3730XL. This generated a complex raw sequencing data in the ABI trace file of A68, with many double peaks. In i124 however, patterns were often simplified, and were subsets of the A68 pattern, which is expected when one of the alleles (the most divergent) is deleted. When the sequence patterns of a gene had double peaks in both A68 and i124, it was concluded that this gene was not deleted in i124. BACs in the middle of the minimal tiling path often showed deleted genes, whereas BAC at the ends showed no signs of deletion. It was therefore concluded that the minimal tiling path spanned the deletion in i124.

Example 4. Unbiased Identification of the Diplospory Gene within the Dip-Locus 4.1 Generation of EMS Apomixis Knockouts We reasoned that when apomixis in *Taraxacum* is genetically controlled, it should be possible to generate knock-out mutations by mutagens such as ethyl methane sulphonate (EMS). Since we could predict the genes within the Dip locus, it should be possible to identify the Dip-gene by resequencing the genes in the Dip locus of the Loss-of-Diplospory mutants. When we would find several diplospory mutants they should have mutations in the same gene (the Dip gene), whereas mutations in genes in the Dip locus but not related to diplospory phenotype would not be enriched. This would thus identify the functional Dip gene.

To generate EMS apomixis knockouts 1800 plants were grown from A68 seeds treated with 0.35 percent EMS for 16 hours at room temperature. After seed set the plants were screened for Loss-of-Diplospory phenotypes (for a description see above). In total six putative Loss of DIP mutants (LoD1 to LoD6) were detected, although in two of them, LoD3 and LoD5, did not produce seeds in pseudo-test crosses. Since the LoD plants segregated for parthenogenesis some viable M2 seeds were produced and from these M2 plants were grown. As far as we know this is the first time Loss-of-Apomixis mutants have been successfully made by EMS treatments. Attempts to generate Loss-of-Apomixis by EMS treatment in other species have been unsuccessful (Asker and Jerling 1990, Praekelt and Scott 2001).

4.2 High-Throughput Re-Sequencing of Genes Predicted in Loss of Diplospory Physical Interval Map in Loss of Apomixis EMS Mutants With the Augustus gene prediction software (Stanke M., R Steinkamp, S Waack and B Morgenstern (2004) "AUGUSTUS: a web server for gene finding in eukaryotes" Nucleic Acids Research, Vol. 32, W309-W312) the genes in the Dip and the dip BAC Minimal Tiling Path (see above) were predicted using the *Arabidopsis* gene model. Gene annotation was performed by BLASTing the predicted protein sequences against the non-redundant database from NCBI, with 40% protein identity as threshold. A total of 129 *Taraxacum* genes were predicted in the Dip and the dip BAC Minimal Tiling Paths Leaf material was collected from *Taraxacum* A68, A68 LoD1 to 6 EMS mutants and LoD deletion line (A68 i124). Genomic DNA was extracted using the CTAB procedure (Rogstad 1992). DNA samples were quantified using Quant-iT™ TMPicoGreen® dsDNA reagent (Invitrogen) on the FLUOstar Omega (BGM LABTHEC) using a standard procedure. DNA samples were diluted to a concentration of 20 ng/µl and subsequently LoD samples were pooled to generate 2 pools (pool A=LoD 1+LoD2+LoD3; poolB=LoD4+LoD5+Lod6).

Specific primers were designed for PCR amplification of the 129 predicted genes, in order to target mainly their coding sequences. A total of 295 primer pairs were designed. *Taraxacum* apomictic A68 clone, A68_i124 deletion line (LoD phenotype) and A68 LoD EMS mutants pool A and B were chosen as targets for amplicon screening with the aim of associating the EMS mutant phenotypes with EMS mutation and to thus identify the DIP gene(s).

From each chosen target 295 amplicons were generated by PCR reaction. Fifty µl PCR reactions were performed containing 80 ng DNA for each of the sample, 50 ng forward primer, 50 ng reverse primer, 0.2 mM dNTP, 1 U Herculase H II Fusion DNA polymerase (Stratagene) and 1×Herculase H II reaction buffer. PCRs were performed with the following thermal profile: 2 minutes at 95° C., followed by 35 cycles of 30 sec 95° C., 30 sec 55° C. and 30 sec 72° C., followed by cooling down to 4° C. Equal amounts of PCR products from samples were used for GS FLX fragment library sample.

Amplicon screening was performed using the Genome Sequencer (GS) FLX+PLATFORM (Roche Applied Science) which allows massive parallel picoliter-scale amplification and pyrosequencing of individual DNA molecules. Amplicon samples libraries were constructed using standard Roche protocols. Barcodes (Multiplex Identifiers, MIDs), were added during libraries preparation. The MID-tagged samples were pooled for simultaneous amplification and sequencing (multiplexing). One full picotiterplate (PTP) (70×75 mm) with two region was used for sequencing the amplicon libraries (A68, A68_i124, A68_EMS pools A and B). Sequencing was performed according to the manufacturer's instructions (Roche Applied Science).

The bioinformatics analysis of mutation screening consisted of 5 parts:

(1) GS FLX+data processing, using the Roche GS FLX+ software. Base-called reads were trimmed and filtered for quality and converted into FASTA format.

(2) Sample processing. The origins of the sequence reads was identified based on the specific barcode. Barcode sequences were trimmed and sequence reads of each sample were saved separately to the database.

(3) Amplicon processing. The origin of the amplicons was identified based on the target-specific primer sequences. Sequences reads per amplicon were clustered using CAP3 (95% homology, 40 nucleotides overlap).

(4) Polymorphism detection. Identification of all potential SNPs and INDELS in each clustered amplicon.

(5) Detecting EMS SNPs. Identification of SNPs that were induced by EMS treatment. Such SNPs are expected in EMS mutant plants only (EMS pool A or B). Considering that six independent EMS mutants were pooled (3 in pool A and 3 in pool B) and EMS induced SNP will be either detected in pool A or B, but not in both. SNPs were considered true EMS-SNPs if matching the following parameters: (a) not present in A68 and A68_i124; (b) detected either in pool A or in pool B.

In total 6 putative EMS mutations (C->T or G->A) were identified, of which four were found in a single gene with a very high protein BLAST homology with the Vacuolar Protein Sorting (VPS) 13 like protein of *Arabidopsis thaliana* (gi|101296531|emb|CAC08248.1|) (Table 3).

TABLE 3

Protein homology between SEQ ID NO: 3 and *Arabidopsis* VPS13 like protein (gi|10129653|emb|CAC08248.1|). Tera-BLASTP search Protein query (DeCypher, TimeLogic ™ Standard settings).

| Amino acid start | Amino acid end | Blast Score | E-value |
|---|---|---|---|
| 643 | 785 | 204.91 | 1.9e−054 |
| 1020 | 1393 | 237.65 | 2.6e−064 |
| 1645 | 2097 | 256.91 | 4.1e−070 |
| 2142 | 2618 | 303.91 | 3.0e−084 |
| 2608 | 3384 | 728.78 | 3.7e−212 |
| 3390 | 3737 | 327.79 | 1.9e−091 |
| 3621 | 3931 | 273.09 | 5.6e−075 |

This is a large gene, representing 34 of the sequenced 295 exons, which corresponds with 11% of the total re-sequenced nucleotides. An enrichment of mutations in the causal Dip gene is expected by the selection for loss-of-Diplospory phenotypes. All four ToVps13 EMS mutations were in the Dip haplotype, none was in the dip haplotype. We calculate the probability that this distribution of mutations over the sequenced genes is due to chance as follows. The size of the predicted ToVps13 is 11% of the total re-sequenced region. Since there are three haplotypes, the size of a single ToVps13 haplotype is 3.7% of the total re-sequenced region. The probability that the first EMS mutant is located in the Dip haplotype is 0.33. The probability that the second, third and fourth EMS mutations are located in the same gene in the same haplotype is 0.037× 0.037×0.037=5.1. 10E-5. The combined probability that the first EMS mutation is in the right haplotype and the second, third and fourth in the same haplotype in the same DNA region is 0.33×5.1. 10E-5=1.67E-5. Since this can also happen for other DNA regions, the probability over the whole re-sequenced region is 100/11×1.67×E-5=1.54. 10E-4. Therefore the probability that this distribution is due to chance is 1.54 in 10,000. Consequently, it is very likely that the Vps13 sequence is involved in diplospory.

In two LoD plants a second EMS mutation was found in the resequenced region, one in an oligo peptide transporter and the other in a putative transporter gene. In both cases the mutation was not in the Dip haplotype, but in a dip haplotype. Therefore we conclude that these two EMS mutations are not related to the Diplosporous phenotype. In the putative LoD3 and LoD5 plants no EMS mutation was detected in the re-sequenced region. These plants did not produce offspring in pseudo-test crosses (see above) and may have been female sterility mutations, rather than loss of apomixis mutations.

Example 5. Association Mapping of the DIP Locus in a Wide Panel of Unrelated Sexual and Apomictic Dandelions In order to provide further proof for the involvement of SEQ ID NO:1 in the diplosporous phenotype, the association between sequence SEQ ID NO:4 and diplospory was investigated in a panel of apomictic (=diplosporous) plants and a panel of sexual (=meiotic) plants. Both panels consisted of 13 unrelated plants, as diverse as possible, with respect to geographic origin and taxonomic group (different sections and different species within the genus *Taraxacum*). Ploidy levels were determined by flow cytometry, according to the method described in Tas and Van Dijk (1999, Heredity 83: 707-714). The breeding system was determined by seed set in isolation from pollinators: apomicts produce full seed set in isolation, sexuals produce no seeds in isolation. Part of SEQ ID NO:4 was resequenced, either 1-300 nt or 7-586 nt, the first by Illumia paired end sequencing, the second by sequening on the Genome Sequencer (GS) FLX+PLATFORM (Roche Applied Science). The sequences were analyzed with nucleotide BLAST against SEQ ID NO:4 using Decypher (TimeLogic) with standard settings. In Table 4 per plant the highest nucleotide sequence identity and the smallest E-values are given. From this table it is clear that all apomicts carry the sequenced region of SEQ ID NO:4, whereas none of the sexuals carries this DNA fragment. Thus there is maximum linkage disequilibrium between this sequence and diplospory. Recombination and mutagenesis will erode linkage disequilibrium between the nucleotide region and diplospory over time if the nucleotide region is not functionally involved in diplospory. The perfect association between apomixis and SEQ ID NO:4 at a large geographic and taxonomic scale therefore confirms that this sequence is essential for diplospory.

TABLE 4

Association mapping between apomixis and SEQ ID NO: 4. The sequences were analyzed with nucleotide BLAST against SEQ ID NO: 4 using Decypher (TimeLogic) with standard settings. Per plant the highest nucleotide identity and the smallest E-values are given. Indet. means indetermined. IBOT means provided by the Institute of Botany Pruhonice, Czech Republic, geographic origin not known.

| Section | Species | Origin | Ploidy |
|---|---|---|---|
| A. sexuals (meiotic) | | | |
| 1. Biennia | *T. nutans* | China, Shanxi | 2x |
| 2. Ceratoidea | *T. koksaghyz* 1 | Kazakhstan | 2x |
| 3. Ceratoidea | *T. koksaghyz* 2 | Kazakhstan | 2x |
| 4. Ceratoidea | *T. koksaghyz* 3 | Kazakhstan | 2x |
| 5. Ceratoidea | *T. koksaghyz* 4 | Kazakhstan | 2x |
| 6. Ceratoidea | *T. koksaghyz* 5 | Kazakhstan | 2x |
| 7. Ceratoidea | *T. koksaghyz* 6 | Kazakhstan | 2x |
| 8. Mongolica | *T. hallaisanense* | Korea | 2x |
| 9. Obliqua | *T. pyrenaicum* | France | 2x |
| 10. Piesis/ Primigenia | *T. cylleneum* | Greece | 2x |
| 11. Piesis | *T. bessarabicum* | Ukraine | 2x |
| 12. Piesis | *T. stenocephalum* | Russia, Caucasus | 4x |
| 13. Ruderalia | *T. officinale* 3 (*FCH72*) | Switzerland | 2x |
| B. apomicts (diplosporous) | | | |
| 1. Borealia | indet. | China, Shanxi | indet. |
| 2. Ceratoidea | *T. brevicorniculatum* | Kazakhstan | 3x |
| 3. Erythrocarpa | *T. gratum* | Caucasus | indet. |
| 4. Erythrosperma | *T. lacistophylloides* | IBOT | indet. |
| 5. Erythrosperma | *T. brachyglossum* | Chili | 3x |
| 6. Palustria | *T. validum* | IBOT | indet. |
| 7 Ruderalia | *T. officinale* 1 (*Ron*) | France | 4x |
| 8. Scariosa | *T. minimum* | Malta | 5x |
| 9. Stenoloba | indet. | Siberia, Yakutia | indet. |
| 10. Mongolica | *T. aurantiacum* | China | 4x |
| 11. Nevosa | *T. richardsianum* | UK, Wales | 4x |
| 12. Ruderalia | *T. officinale* 2 (*A68*) | Netherlands | 3x |
| 13. Scariosa | *T. hybirnum* | Russia, Crimea | 3x |

TABLE 4-continued

Association mapping between apomixis and SEQ ID NO: 4.
The sequences were analyzed with nucleotide BLAST against
SEQ ID NO: 4 using Decypher (TimeLogic) with standard
settings. Per plant the highest nucleotide identity and
the smallest E-values are given. Indet. means indetermined.
IBOT means provided by the Institute of Botany Pruhonice,
Czech Republic, geographic origin not known.

| Section | nt identity | BLAST E_Value | Region SEQ ID NO: 4 |
|---|---|---|---|
| A. sexuals (meiotic) | | | |
| 1. Biennia | 93 | 6.4e−128 | 1-300 |
| 2. Ceratoidea | 95 | 8.9e−081 | 1-300 |
| 3. Ceratoidea | 96 | 1.5e−085 | 1-300 |
| 4. Ceratoidea | 95 | 8.9e−081 | 1-300 |
| 5. Ceratoidea | 93 | 5.3e−076 | 1-300 |
| 6. Ceratoidea | 95 | 8.9e−081 | 1-300 |
| 7. Ceratoidea | 96 | 1.5e−085 | 1-300 |
| 8. Mongolica | 96 | 1.3e−150 | 1-300 |
| 9. Obliqua | 99 | 7.1e−100 | 1-300 |
| 10. Piesis/Primigenia | 95 | 3.7e−083 | 1-300 |
| 11. Piesis | 97 | 2.5e−090 | 1-300 |
| 12. Piesis | 91 | 5.5e−116 | 1-300 |
| 13. Ruderalia | 96 | 1.3e−150 | 1-300 |
| B. apomicts (diplosporous) | | | |
| 1. Borealia | 100 | 4.4e−172 | 1-300 |
| 2. Ceratoidea | 100 | 4.4e−172 | 1-300 |
| 3. Erythrocarpa | 100 | 4.4e−172 | 1-300 |
| 4. Erythrosperma | 100 | 4.4e−172 | 1-300 |
| 5. Erythrosperma | 100 | 4.4e−172 | 1-300 |
| 6. Palustria | 100 | 4.4e−172 | 1-300 |
| 7. Ruderalia | 100 | 4.4e−172 | 1-300 |
| 8. Scariosa | 100 | 4.4e−172 | 1-300 |
| 9. Stenoloba | 100 | 4.4e−172 | 1-300 |
| 10. Mongolica | 100 | 0.000000 | 7-586 |
| 11. Nevosa | 100 | 0.000000 | 7-586 |
| 12. Ruderalia | 100 | 0.000000 | 7-586 |
| 13. Scariosa | 100 | 0.000000 | 7-586 |

Example 6. Expression of the DIP Gene in the Megaspore Mother Cell of a Apomict and a Near Isogenic Loss of Diplospory Mutant With the aim to study the expression of the DIP candidate gene, RNAseq was performed from isolated Megaspore Mother Cell (MMC) and Female Gametophyte (FG) of the apomictic (A68) and its isogenic deletion line (i124). Pilot studies made clear that megasporogenesis in *Taraxacum* occurs in the buds of very young inflorescences (~0.5 cm in diameter), before stem elongation, when the bud is still in the rosette of the plant. For the later stage (Female Gametophyte; FG) buds were collected with a stem length of 1 cm.

Fresh ovaries were cut open and were macerated in a mannitol mixture of pectinase, pectolyase, hemicellulase and cellulase. Ovules were separated from surrounding tissues by manual micro-dissection using a needle. Isolated ovules were collected in batches of 20 ovules using a CellTram® Oil device (Eppendorf) and immediately frozen in a −80° C. freezer until further processing. RNA was extracted from pools of 20 ovules with an Arcturus® Picopure® RNA Isolation Kit. RNA was linearly amplified by in vitro reverse transcription using an Ambion MessageAmp™II aRNA amplification kit. Different pools of 20 ovules from the same genotype and tissue, were considered as biological replicates.

In total 10 samples were sequenced in 6 Illumina HiSeq lanes (3 biological replicas of A68 MMC, 3 biological replicas of FG and 4 biological replicas of MMC i124). Per sample, overlapping read pairs were merged using FLASH software (http://ccb.jhu.edu/software/FLASH/). The merged (unfiltered) reads were assembled using Trinity software (http://trinityrnaseq.sourceforge.net/). For each sample, transcript abundances were estimated according to Trinity's "Abundance Estimation Using RSEM" protocol (http://trinityrnaseq.sourceforge.net/analysis/abundance_estimation-.html). Differentially expressed isoforms were then identified following the "Identifying Differentially Expressed Trinity Transcripts" protocol (http://trinityrnaseq.sourceforge.net/analysis/diff_expression_analysis.html).

Among the de novo assembled expressed genes, more than 40 meiotic genes were detected (e.g. Dmc1, Spo11, Rad50) indicating that the right developmental ovule stages, MMC and FG, were studied. SEQ ID NO:4 was de novo assembled and shown to be expressed in the apomict A68 at moderate expression levels, in both the MMC and the FG stage. In Table 5 the expression is quantified as FPKM values (Fragments Per feature Kilobase per Million reads mapped). In the deletion mutant i124 SEQ ID NO:4 is not expressed, but in its diplosporous homolog A68 is. The expression data therefore confirm that the Vps13 gene is in the deletion and that it is expressed at the MMC and FG developmental stages.

The expression and association mapping analyses performed so far indicate that the nucleic acid molecule as set forth in SEQ ID NO:4, currently annotated as the 3 prime terminus of the Vps13 gene, is transcribed independently, either as a novel gene or as a differential splicing variant of the Vps13 gene, similar to the sporulation gene Spo2 of *Saccharomyces pombe*. The Spo2 gene encodes a 15-kDa protein composed of 133 amino acid residues that was incorrectly annotated as being the last exon of the *S. pombe* Vps13 gene. Actually the Spo2 gene is immediately downstream of the Vps13 gene and transcribed independently (Nakase et al 2008, Molecular Biology of the Cell. Vol. 19, 2476-2487).

It is noteworthy that the mRNA sequence of SEQ ID NO:5 does not contain an ATG start codon, and that possible translated Open Reading Frames are short. However, using ribosome profiling in budding yeast (*Saccharomyces cerevisiae*) the Brar lab (University of California—Berkeley http://www.unal-and-brar-labs.org/brar-sorfs) has identified noncanonical translation of thousands of new short peptides during meiosis. These meiosis-specifically expressed short Open Reading Frames (sORFs) have no ATG start codons and their translated peptides are shorter than 80 amino acids and will therefore not be predicted by standard gene software. sORFs are located in regions previously not known to contain expressed sequences. sORFs can also be short alternative isoforms of proteins with known function. The presence of these short peptides during meiosis had been confirmed by classical methods. However, the function of these thousands of these short meiosis specific peptides remains a mystery.

TABLE 5

Expression of SEQ ID NO: 4 in Megaspore Mother Cells and Female Gametophyte of the apomict A68 and the Dip deletion line i124. Absolute expression is measured as fragments per feature kilobase per million reads mapped (FPKM). The mean and the standard error are calculated. The percentage of allele-specific expression is indicated.

| Plant | Tissue | FPKM | S.E. |
|---|---|---|---|
| A68 | MMC1 | 6.80 | |
| | MMC2 | 5.96 | |

TABLE 5-continued

Expression of SEQ ID NO: 4 in Megaspore Mother Cells and Female Gametophyte of the apomict A68 and the Dip deletion line i124. Absolute expression is measured as fragments per feature kilobase per million reads mapped (FPKM). The mean and the standard error are calculated. The percentage of allele-specific expression is indicated.

| Plant | Tissue | FPKM | S.E. |
|---|---|---|---|
|  | MMC3 | 8.54 |  |
|  | Mean | 7.10 | 2.51 |
| i124 | MMC1 | 0.00 |  |
|  | MMC2 | 0.00 |  |
|  | MMC3 | 0.00 |  |
|  | MMC4 | 0.00 |  |
|  | Mean | 0.00 | 0.00 |
| A68 | FG1 | 6.45 |  |
|  | FG2 | 5.56 |  |
|  | FG3 | 6.45 |  |
|  | Mean | 6.15 | 0.69 |

Example 7. Overexpression of ToDIP and Todip in *Arabidopsis thaliana*

A ToDIP sequence fragment (SEQ ID NO:11) preceded by an artificial ATG start codon and a Todip sequence fragment (SEQ ID NO:9) preceded by an artificial ATG start codon were cloned into a vector with a 35S promoter. Three independent *Arabidopsis* floral dip transformation experiments were carried out with these constitutive overexpression vectors. In each experiment between 15 and 30 $T_0$ plants for each allele were obtained.

The 35S::Todip overexpression transformants were indistinguishable from wildtype plants and were fully fertile. In contrast, of the 35S::ToDIP overexpression transformants in all three experiments some plants were partially sterile (20% of the transformants in the first experiment, 10% in the second and third experiment).

Megaspore Mother Cell (MMC) and Female Gametophyte (FG) development were investigated by Nomarski microscopy of cleared ovules using the method of Yadegari, R., et al. (1994) Cell differentiation and morphogenesis are uncoupled in *Arabidopsis* raspberry embryos. Plant Cell, 6, 1713-1729). MMC and FG development in all investigated 35S::dip transformants looked normal, like in wildtype *Arabidopsis* plants. However, the 35S::ToDIP plants often showed abnormal megaspore mother cells, extra small nuclei next to the megaspore, as well as disrupted FG development, like arrest at FG1 stage, absence of vacuoles and collapsed embryo sacs. In an *Arabidopsis* dyad mutation, which affects female and male meiosis (Ravi M et al. (2008) Gamete formation without meiosis in *Arabidopsis*. Nature 451: 1121-1124), similar disturbances of FG development were observed. Therefore, the observed 35S::ToDIP abnormal MMC and FG phenotypes likely indicate the presence of a disrupted female meiosis.

These ToDIP phenotypes were dominant since they were observed in the hemizygous $T_0$. This is consistent with the dominance of the DIP allele in *Taraxacum*. In the first experiment, in some plants also pollen development was affected (extra nuclei), but in the second and third experiment pollen development looked normal. At least in the second and third experiment the phenotypic effect of the DIP construct is female meiosis specific, which is consistent with the DIP function in *Taraxacum*.

In conclusion, it was found that the *Taraxacum* DIP allele produces a female specific dominant on meiosis in a heterologous plant species. This effect was not found for the *Taraxacum* dip allele. The *Arabidopsis* overexpression phenotypes provide strong supportive evidence that the DIP sequence is causing the diplospory phenotype in *Taraxacum*.

Example 8. DIP Gene Functionality in *Taraxacum*

To further confirm diplospory function of SEQ ID NO: 4, *Taraxacum* i124 plants, in which the DIP allele is deleted, are transformed with plasmids containing SEQ ID NO: 4, fused with different promoters and regulatory elements in appropriate vectors. The following promoter sequences are used:

1. The native *Taraxacum* promoter of SEQ ID NO: 4 (about 1500 bp of SEQ ID NO: 1, upstream of SEQ ID NO: 4)
2. The promoter of the *Taraxacum* ortholog of *Arabidopsis* Dmc1 (At3g22880)(Klimyuk V. I. and Jones J. D. 1997. AtDMC1, the *Arabidopsis* homologue of the yeast DMC1 gene: characterization, transposon-induced allelic variation and meiosis-associated expression. Plant J.: 11:1-14). This gene has a meiosis specific promoter.
3. The 35S promoter. This promoter results in overexpression of SEQ ID NO: 4.

Protocols for the transformation of *Taraxacum* plants have been published by Wahler et al. 2009 (Plant Phys. 151, pp. 334-346). Since i124 carries all other elements of apomixis, complementation of diplospory will restore apomixis which can be easily determined by high seed set in this triploid plant and by genetic markers in the T1 progeny. The progeny plants contain the full maternal genome, with no segregation of maternal markers.

Example 9 Introduction of Diplospory in Sexual Crops by Transformation

Sexual diploid plants of rice and lettuce are used for transformation according to the protocols of Dreni, L et. al 2011 (Plant Cell 23: 2850-2863) and Dias, B. B. A. et al. 2006 (Plant Pathology 55: 187-193), respectively. The same constructs with promoters and SEQ ID NO: 4 as disclosed in Example 8 are used. After crossing $T_0$ diplosporous plants with diploid pollen donors, triploid progeny is produced. Triploidy can be determined by root tip chromosome counts or by flow cytometry. Both are standard methods (Tas and Van Dijk 1999, Heredity 83: 707-714). Further proof for diplospory can be found in the analysis of the progeny plants for genetic markers. In addition to paternal markers, the progeny will carry the full maternal genotype.

Example 10. Introduction of Diplospory in Sexual Crops by Genome Editing

Targeted genome editing technologies such as CRISPR-CAS9, TALENS and ZFN (zinc-finger nucleases are commonly used in the art to generate mutations in existing genes. Not only by creating knock out alleles, but also by introducing mutations encoded by so-called 'repair DNA'. (e.g. Doudna J. A. and Gersbach C. A. 2015 Genome editing: the end of the beginning Genome Biology (2015) 201516: 292, and references cited therein).

Such stretches of DNA typically encode fragments of a (target) gene sequence in which alterations are introduced that lead to an altered gene function. Typically such sequences replace the gene sequence targeted in the genome editing event by homologous recombination thereby introducing the mutation of choice in a targeted way in the genome of a host cell, e.g. a plant cell.

This example encompasses the introduction of alterations to the dip homolog in a given plant species that lead to a functional change into DIP, i.e. altering the function of the naturally occurring recessive non-diplosporous allele by the dominant diplosporous (DIP) allele.

Dip homologs are readily identified in many plant species. CRiSPR CAS mediated genome editing using *Taraxacum*-based 'repair' plasmid design can convert the native dip homolog into its DIP sibling by simply modifying SNPs and indels in line with the differences between the *Taraxacum* DIP and dip alleles.

The invention claimed is:

1. A polynucleotide comprising a chimeric gene that comprises:
   (a) a nucleic acid sequence comprising:
      (i) a sequence having at least 95% sequence identity with SEQ ID NO: 11; and/or
      (ii) a sequence encoding an amino acid sequence having at least 95% sequence identity with SEQ ID NO: 12; operably linked to
   (b) a promoter sequence that is not naturally associated with (a), wherein said polynucleotide, an expression product thereof, and/or a protein encoded thereby, is capable of providing diplospory function to a plant or plant cell.

2. The polynucleotide according to claim 1, wherein the nucleic acid sequence of (a) comprises:
   (i) a sequence having SEQ ID NO: 11; and/or
   (ii) a sequence encoding the amino acid sequence of SEQ ID NO: 12.

3. The polynucleotide according to claim 1, wherein the promoter sequence is active in plant cells.

4. A nucleic acid vector comprising the polynucleotide according to claim 1.

5. A plant, plant part or plant cell comprising the polynucleotide according to claim 1, wherein the polynucleotide is present and/or expressed at least in a female ovary.

6. A seed of a plant according to claim 5, wherein said seed is an apomictic seed of said plant and/or wherein said seed is a clone of the plant on which it developed.

7. The plant, plant part, or plant cell according to claim 5, wherein said plant, plant part, or plant cell is from a species selected from the group consisting of the genera *Taraxacum, Lactuca, Pisum, Capsicum, Solanum, Cucumis, Zea, Gossypium, Glycine, Triticum, Oryza, Allium, Brassica, Helianthus, Beta, Cichorium, Chrysanthemum, Pennisetum, Secale, Hordeum, Medicago, Phaseolus, Rosa, Lilium, Coffea, Linum, Canabis, Cassava, Daucus, Cucurbita, Citrullus*, and *Sorghum*.

8. A method for conferring diplospory on a plant, plant part or plant cell, comprising the steps of:
   a) transforming said plant, plant part or plant cell with the polynucleotide according to claim 1; and
   b) optionally, regenerating a plant, wherein said polynucleotide is present and/or expressed at least in a female ovary.

9. A diplosporous plant, plant part or plant cell obtainable or obtained by the method according to claim 8.

10. The polynucleotide according to claim 1, wherein the nucleic acid sequence of (a) comprises:
    (i) a sequence having at least 98% sequence identity with SEQ ID NO: 11; and/or
    (ii) a sequence encoding an amino acid sequence having at least 98% sequence identity with SEQ ID NO: 12.

11. The polynucleotide according to claim 1, wherein the nucleic acid sequence of (a) comprises:
    (i) a sequence having at least 99% sequence identity with SEQ ID NO: 11; and/or
    (ii) a sequence encoding an amino acid sequence having at least 99% sequence identity with SEQ ID NO: 12.

* * * * *

SEQUENCE LISTING

```
<160> NUMBER OF SEQ ID NOS: 14

<210> SEQ ID NO 1
<211> LENGTH: 23361
<212> TYPE: DNA
<213> ORGANISM: Taraxacum officinale

<400> SEQUENCE: 1
ttttcaccta gaagagcaca accctcttca agtgaagcac acactcgaag tgtatttccg      60
tatttcagtc cagctggaaa cagaagacca ttaatgatat tttagcaaga aagctttcat     120
tcatttgttc atcatagcag catcctactt cctacaacat tgtattttga aaaatctacc     180
aattaaatag caatatcatc caaatacaaa gcaagtttca ctgctatata ttgctaaacc     240
tctctttaat ccctagatat aataagggca aaaaagtgga acatatgtac ctttactctg     300
tcatttgatg ataaatgttg tttttaagtt agtatcaaac tgaaattgtg ctaatcacaa     360
tggtgttgaa ttgttggcaa attctattta tttaataaat cataggtaaa acaatgacat     420
ataaactatt ttactctacc atttgacaac cactcttgat gtatcaaact gattatatga     480
caccccaccc catataatca gataatcact tccaaaaagc atatccaacc acccctctat     540
attttcacta actatcccaa ttgcctgtct ataaattcag aattaataaa tctactcagc     600
tgattgattt tgaataaata ataatgacac attgcatact gatagataaa gttctgcagc     660
acccaaatca aatgtcctaa aaccttaagg tgaagaacac agcccaaagg aattgaagat     720
cgacatatac tctttaacag ttccttaata tcaatgacaa aactgaatcg aatttaacgg     780
ggggaaaaat aaatacacca atttcataac ttaaaacacc tggttaatcc tcgcgactac     840
aaatcaaaac agctgaatat ttaaccaaga gaaaaaataa aaaccctagt tgatcgcatt     900
gacatctgag ctacacacat ccaattacat aacgaaaaat acgaatcaga agtttacgaa     960
acgaaacaag atctagtcaa taaagaaaac tgaaactaag acagatcaga aaagtggttt    1020
ctcgaacgta cctgatcgaa gtgaagatgt cagatctgat aaactggtat cttgtagtaa    1080
aagatgaatc gagagataaa aatgaagaac gaatgcagaa ttgtaatata aaatacacaa    1140
aactcaagat ttatttctgt tttatgttga aaatttgaat gaaaatgatt ctaacagaga    1200
aagggtttgg tcttttcctt ctgtttctct gtcaacaaca atttagggaa ggcgtagaga    1260
gatgagagca gacagcgcac ctttgcgcgg agaatttctg ggatatatct atttatttcc    1320 cttttaccctt tcttttcatt atgtttttt tttttcttc agaaaattca aactttcttt    1380
ttcaatattc tgagtacgct aatttctagc tggcatgtag caagtcttaa tttctagctg    1440
gcatgtagca agtctttgtt gggtggtata gcatttccct cttttaata gtaagtgaaa    1500 atgacttaat agggtaaaaa cgtttcgaac ttgtccatat ttggtcatta tcctatttt    1560 tgtacacaat acaccattaa gatttatatg accggttaag tttcgtccat tgccgatttt    1620
cataggtaat catcgtgaaa tcagtaagca acctcatgaa tcacccactc ctgccgccac    1680
aaccacagcc gaagcttcat ttgagcccct ggatgaaaat ctcttctcgg atctaacccc    1740
actctgttat ttactccaat ccacctcccc caaatcaccc ccaacattaa tctttcctcc    1800
```

```
gttctaccac caccaatcct ctcaagattc atcctttctc atcgccgtga cgttttccag   1860
caaaacccat gtccaccacc gccgccgtca aaccagtccg gaaattcccg ccatcgtgcc   1920
cggatgtaac cccgccgtca aaccagtccg gaaatcaaca acacaacccc ctgttttgca   1980
tcaccagagc ttgaatccgg gtcgtggagt tcgatttaaa ctatcttcaa ctcaaaatct   2040
ggtaacatta gcagctagtt ccaccaatca taccccctgat ttcgattcta ggtttccaaa   2100
tcacgattcc tcatacatga caactggtc taatcaagaa gaagacaacg acgatgggtg   2160
tcttgatgac tctacaatta atgaaacctc gattcatccg ggtaccaaaa tcacaagagt   2220
gtgaaaggag gaattcggat aaaatcctca attccatccc acctcgggcc gagaaagttg   2280
agcaaggctg ctcatgaaca tgaagtcgat gaggatggtg aaatgtggat taaagtgcct   2340
agaaacacaa atttgtttta cgggaaccat caaaacggca atagttttaa tcctaattgg   2400
gatcaaggga agaaaagaag aaatgaaggg atataggagg tggttcaatc gattaagcta   2460
ttaggagatg ggttcatgaa gatgctgact gatttcagga ggttgctgac tgatttcacg   2520
atgattacct attaaaaccg gtaaatggac gaaacttaac cggtcatata aaccttaatg   2580
gtgtattgtg tacaaaaaaa taggataatg accaaatgtt gacaagttcg aaacgttttt   2640
accctattaa gtcattttcc ctaatagtta actaattatt cttttcggct ctaaattatt   2700
ttttgttata atttcttcta aatagactgg tttatctttc ttaattactg tatgaaacat   2760
ttcacaaact tattactttt taaaaatata tcatatttct caagataaaa agtaagataa   2820
aagaattaat atatctatgt gttacaaatc aaaaaatgat aaattgttgg atgccgtagt   2880
attttgccac gactaaaagt taacatatta tttctagggc attttaata ataaagaaac    2940 tgacttatat atatgtaaca tattatttgt tcatatttag tcattatata tcttttgtca   3000
tattattaaa tttgttacaa ttttttatat ttagccacta caatttgcaa ttgcaggtca   3060
tagtgaccaa atgtaaacaa ttgcaacaag ttcgatggta taatgtgaca aaaaaatata   3120
atgaataaat atgttttcaa acattctttt ttatatttag ccactacaat ttgtcatctg   3180
agttggaata aatatgtttt caaacattct ttttttaaat tcaaaatgaa tgttctcgtg   3240
taaatcacag caatcactta ttatgatttt acattattgt gaactaaaat aaaacttctc   3300
gacgaaatac atatattgta tataatatct ttacttccgg tagtcgtgtt tttaaaatat   3360
attcaatctt attatatgta caattaaata ggttaattaa taaaacataa ttattatatt   3420
aaatatattt attgatagat acaaaaaata gaagttagta tagctaaatg gaaaaaaacc   3480
ataaaaaaat gattaatagg ttattggtgt catatttatt ctaaacgcta acatatatg    3540 gttctaaaaa aatgtctgat gaatgttcaa aatatggtac aaaataatgt ctcaagaact   3600
gtaacatcct taattttag aagttatgtt ttaagttaaa attaactaat taggacctaa     3660
tttgttaagt tttaggataa taatgaaaga aataaagaga ctcaaggtta ttttgcattt   3720
ttgacaagta gagggaccac taatgaaaaa tgtggaaatt aaaagcctgg aactctcttc   3780
cagcttctaa gatcgcgaga gaaagagagc agtgaaaggg agggcgatt ttgagagcaa    3840 accaagaaca agagctaaat tctgatcatt gaagagatta ggagtgatac taaagaggat   3900
tcaagcacaa aaaggtaaga aatcatcttc tatttacaag aaattcgttt ttgatgttga   3960
gggtagaaac ccaaaatcga atcagatga aattgaaggt ttaagggctg gattctaacc    4020
tcttttggtc attagaagtg atttctagct tttgctcacc tttgaattga ttatttgaag   4080
gttttgggga agatcaccat gaacttagaa tttgctattg ggtttgatt atatgctttg    4140 attccatccc ttagacatgt cataaagcct gtaaatgagt gataagaagt attgctaaaa   4200
```

```
ggttaggact tgtagaccaa agtttggaag ttgcaagaaa ttggaaaaga gaagctgcct   4260
agactgcgga cacgggtcgt gtcccacagg ctggaatcat tttgagtttc gatttcttta   4320 ttttttatc caattccaat aattccaagt gcaataagct tagatatgat gataaatgag    4380
ttgcacaaaa gttgaatata tttggaaata cccaagggta ttttggtcat tttaatgacc   4440
tttagactat tgttttgtag aaaacaaacg aagggagcaa taggaaggag gtctagctgg   4500
gggttgcaag tatctgaaaa cctctacaac ctaaggtgag tacgtgtgat tcatttcccc   4560
tctttgaggg tatgtttatg tgataggaat ctatgtatgc aaagtaggtt gttattgtaa   4620
agggaaatgt tagtctttct agttgcaggt actatgttgc tatgatgatg tatagaatga   4680
tatgaagata tgaatgctag aaagaatgtg tacgaaatga atgagaatgt tgtccggact   4740
atgagagcct cgcaaggggg cctagaggat tctattggga cggtacctcc cttcgcgaaa   4800
tagaactcct aatgtgtatg agagccttgg tggactgatt tgttcttttc accttggcct   4860
agacttgggg tggttcctaa taggacatag accctaagtg taaaggaatg atcattgaag   4920
gggatcccga tatattgtgg ataatggcac aagaattaaa tagaattgat gatgttataa   4980
attgaattta aatgaatgtt ttagattata tccgcgtatc tcaccagacc ttgtctgata   5040
tgttgttttg tgccatgtat tccaggtagt agttctcatg cataggagat ttggatattt   5100
tgaagttata ttagcaagtg gaatgaagac ccggttgtta tccattctcc aattcagttt   5160
atactatggt tgttttgat acaagttgtt aaatacccca aacttaatta catcttttga    5220
aagtaaatgt ttatgatatg taaatagttt taaacttgat atgttttctt ggttaaacca   5280
tagtcataaa aaatatttt aaaaagttat gaaaggttgg ggtgtttcaa gaacagtccg    5340
acagcggccc tcctccgacg gtgtttcccg gcgagttcct ttctactccg gctagcttcc   5400
ccattattgg attaacctat tactgcacct ctccctccgt ctcgaacatg tcacattgtt   5460
ctcggttctc tctgccatga ccataacaac aaacatatgt atagttgtgt gtaggcattg   5520
agtttaaacg gaggagaaaa tatgccatgg ccagctcacc cgctgtcgcc atcccagcca   5580
gcattagccc agccgtcgct cacatccacc gaaaagctga tttccacatc gtcgctcccg   5640
gccgtcacct acacgtaggt tcgtaagttt ccaatatctt agttgcgttt tcggatggct   5700
gataaaaatg catccgttga caaggaagat attgtgattt gtgagtaaac tattttgctg   5760
gaggaaggtg agttagatca catggcgagc atggtaagat gtgaggtggg taaatttcca   5820
ttcaattact tggggcttcc catagggca aacatgaaat tatctaaaca ttggaacatt    5880
atagttgata agtttgagaa aagattatca aactggaaag ctgagaattt gtccttttagg  5940 gggcggctga ctttgataaa atcggtgatg gggagtcttc cgttgtttta tttctcgatg   6000
tttagggctc cgaagaaagt ggtcgataag ctagaaggga taagaagaag gttcttatgg   6060
ggcggtaaga agtcggaaaa aaagattcac tgggtttcgt gggagaaggt gataaaatca   6120
aaagataaag aaggtttagg ggtgaatgga ttgagcagca tgaatatggc cttgctagtg   6180
aaatggtttt ggcggctcaa aactgaaagg gacagcctgt gggttagatg tgtcacggct   6240
tgtcataata tcaaacttat tgatgggaaa cgggtggcta agcttccctt gaaaggagta   6300
tggtggaaca tcatgagctg tgttgaagag ttaaaaacga aaggaatttc tgtggagtca   6360
aagttagtaa ggcaactggg aaacggcaaa cacacgcatt tttggaagga tagatggtta   6420
cacaacaaag ttttaaaaga tgaccttccg gagttgtaca aatagaaggg gacaaaaat    6480 tgtatggtaa accaaagact ggtttgggac aacaacgaga aaatattcaa gcaagcttgg   6540
```

```
gactggaaaa gaccgatcag gagaggaaga gaaaccaaag aactcgaaac tttaataatt      6600
ttgacaaatg ggatacaatt aaaggaaata gaagataatt ggagatggaa ggagggatcg      6660
gacgggaaat tttcggtggg aaaattgagg aaactctttg cttatcagga gcaggccgag      6720
gttgatggtg gattcgattg gatcaattgg gtccccttga aggtgaattg ctttgcctgg      6780
aggttgaaac aagagcgagt tcctgtgatg tgtaaattag caaagagagg ggtatatgtg      6840
gaatccaaaa tatgtaaaat ctgtcaacag gaagaagagg aaaccgaaca tgctttttc      6900 aggtgtgcac atgcgcatca ggtgtgggac tggttcaaga tgtggtcggg tctgatgcgg      6960
gaaatccctc taaacttcag atccatggag gcggagatca aggctggtgc tggtgacaaa      7020
aaatcggtga aactaggaat ggctttggct tatgtgatgc tgtggactat ctggaaaatc      7080
aggaatggtg cagtcttcaa aacagaaaa gcgagggcaa tgaacacgac ggatgaggtt      7140
caattaatct cctttaattg gataaaaaat agaagtagat gcaattggat caaatggtgt      7200
gattggggtg ttaagccttg catgaactgt aatatgtagc tgtactcttt gtttctctag      7260
catcttgcta gaagttttgt tttgctttta taataccaac gccgttcaaa aaaaaaaaaa      7320
ctattttgct gagttttga cgaaatgagt gttattttta aaacattttt cgctttgtta      7380
ttttaaaaca tttaccaaaa gggtagtaaa catatttaca aaaagagtgt tttttaaaat      7440
taacaaccag tgcgtaaaac accccggtt ccttcttcct tgcgtcgact tcagaaatcc      7500
atctcctacc ggccgacttc accagcggcg gctccctctc catctccggc gccctctcca      7560
gcgaccgctc cctctccacc ggcgacgtct tctccagagc cggcgaccca caggtagggt      7620
tcttgtttct ttaggggacg tctttgaatt tgcctgaaat tgcctgaaac aacagtgaga      7680
tttcaagtca aatagttgtt gacctgaaat tgcttttgt gtttcaaatg gaaaggaata      7740
ggtgttgatt taaatcaata gcttgcatag cctacagtgg gattcaagtc acaggtaggg      7800
ttcttctttt agaaattgcc tgaaacacct atttgaccta ttcctttcca ttcgaaattg      7860
cttgcatagc ctacagtggg attcaagtca aagctattgt gattaaaata atataaaggt      7920
cgtacagcag acaacttgta aaggaacatg ctctgatcat gatccatccc ctgtcagtca      7980
tttgatcctg tagtagcccc atgctaattg gcactgaggt gactgtcttc aggtaacaca      8040
ttattgtgta ttacttcaat taatcatgtc catttttatgt tttcatctat gttaatcatt      8100
tcccgctatt tattattccg tgcttactgt actaacattg cagttttata attggtatag      8160
gaaatgtttg aaggtttagt acggcagctg atattaggtt atcttggcca atatattaaa      8220
gatatacaca gagaacaact caagatcaca ctgtggaatg gtaagtcacc actctctatc      8280
atattcatga caaatagttc acgtagtttg ttattcatgg cttgctactt ttcattaata      8340
tcagcacaat atatttactt ttagtcattt acatttatgt ggttttaag ggtataacag      8400 cataagctga atactcatat cactcacatt tatggtgaac accaatatgc catttcttct      8460 atgcccctt cctctttatt tatttatttg taacttggtc tgaggcatgt tttctcgtct      8520
ttgatctctt tatgactcct tcaatatttc gccatattat atattcgtat caatatccag      8580
tgaattcctt atatctgatg tcatttttat gtgaagaaca tactgatcac aatctatgct      8640
attgaaattt tgctctcatt ttaatgcaga ggaagtgttt ttggaaaatg tggagttaat      8700
tctggaagct tttgattatc ttgaacttcc gtttgctcta aagcaaggtg atcaataata      8760
tccgtaaact ttcaagtttc aatactttgt ttatattgtt attttgatg tggtttctca      8820 tttttgggtt ggttgtcatt atttgacaca tgtgagtggt tgataggacg ggttgggagg      8880
ctaagcatta gaattccttg gaaaaagctt ggttgggatc ctattataat aatcttagag      8940
```

```
gatatattag tttgtgcctc tcaacgtgag gatgaagagg taagtagtat ctcatttcaa    9000
ggtataataa gtattgtgca tctccattat attatataac ttttcactaa tgtgaacagt    9060
tatccttttt gtagtggagt gttgatgatg ttgaaagacg agaattttct ggaaaaaagg    9120
ccaaacttgc tgcagcagaa ttggcaaagt tatcgcaacg tgtatgtggt gagtgactat    9180
tttccatttc tatgtttcat tgttataact cctgttattc attgtggact atgataatat    9240
gcattaattt aaagaagttg aagactacca ttgctggtag gctttgtatt ttagtgaaat    9300
agtaactatg ttttgccagt cctatatgta aattaaacag cttttcagc tttcttcact     9360
gttggcagtc tttttaatgc tcagatcttc cagagtttta taagatcacc ttttactat     9420
acttttttat tgttgtaggg aaaagtcagt gttagttaat catagctata tacttatatt    9480
cactgttaat gcatttaatt ctttcatccc aaaagatgca ttttttgac acaatacata     9540
ataaaaatgt tggttattgg tcaaatataa aaatattca tttatgaggt caaaataaag     9600
attttattt tttgaaccag aatcaaaatt tcggatatta ataacaata gttaatggga      9660
aaacacatta agaaatgttg cttgtcgtat atgtatatgg atatatggga atatgggatc    9720
agtgacattc ttggatacac cctttttttt ttttgcataa aaccagtaaa atctttttca    9780
cattatttgt gctaatatgt tgtctttttc tgcagataat cagactggga aatcatttat    9840
gtcatacatt actgccaagg tagtgagatt tcatgttgct tgaacttgtt aaaaatgtca    9900
aaaagtcata tgcctgtttt tccgttttac ttatcatgta atcttagttt tcttaatctt    9960
catttgaaat caggtttgat tttacgtgta aatggtctga tagttgtgtc actagtattt   10020
atttatctat ttattcccat ccagattatt gatggcattc aagtcaccat caggaatgtc   10080
catatcgtat atagagatat ttcaaatgaa aaatcccaaa ctgtatttgg tgtgaagttg   10140
gctagtttga ctgcaatgaa gcaaaactat gctgggtata cctcttttc ttactctaca    10200
gtcaatcaca tacttaaatt ttcacaaaac tcttaatgac tttgatatat gtatatatat   10260
cttcagggta ttaagtggaa aggtgagagt tggccaagta aacaaaattg ttgagataca   10320
aggtttggaa atatactgta aaacctttca tggatcttca acagacatcc atactgaaaa   10380
tggtgaagac tccatggcaa tggtggctgc aagttatgat aatgatgaac atgctcactt   10440
gttggcccca gtcaacgtat ctgcttctct ttcggtatgc atcatgcact tgtaccatct   10500
cataacaaat tttctagatt tttattgtta tgttgtactt tgcaggtgaa taggtctgga   10560
aggctggaga ataatgcagc acaatactcg gttgatattg agttgtctgg cttggttagt   10620
tagttcctta acttttctaa tcataattaa ttattaagtt attatgtcag attatctaac   10680
atgttagtat gtcaccattt ttaggtattg tccctagatg aagatcagtt gcagcaaata   10740
ctgtatctat atgaatatct atgcacatgt cggctaagag agaagtgagt ggattgctttt  10800
ttcaccacct tatcctttag aattacattt tcattatcct tttattgttt ttttaagata   10860
tggacgatat cgtccttggg ggaaacctat atcagagaga caattgggat ggcagataca   10920
gtggtggcat tatgctcaac actctgtgtt atctgatgtt cgtaaaagac tgaagaaaac   10980
ttcatggaaa taccttggag aacgtctgta agtttaattc tttatttaat ttaacatat    11040
acctgcaagt ttttatgat gaaatcttga atctgttac atgtacagag gcagaaaacg     11100
acggtatgta aatctgtaca aattgaaact cgaatgtctt cgaaaagaac aggtgagttt   11160
tcatgattta aacatcaagg tgtatatgat ttaaacatta ttttaaatta tgaattatga   11220
tcagcctttg gatgatgaaa ttgtaatgga gttggaccaa atggagaaag tgtctgatat   11280
```

```
agaagatata ttgagttaca gatctgctgc tgagaatgaa cttcaggtat gattaagatc   11340
attgctattg gtatctataa cacatgcatt tatttaactt atacctttta ttaaagacta   11400
tgaaaatgta ggagttcttg gtggattcac cttctggtat tggaggtagt gaagtgaata   11460
ctaccattga caagtcaatg gatgatgacc aaacatctgg caaaccgcaa ggatggttga   11520
aatggctgtc ccgtggtatg ctaggtgctg gaggtacaga cgattccagc cagttttctg   11580
gtgttgtttc agatgaagta atcaaggtaa ggtgaaatga tttcaattcc aattgaatta   11640
attaatcatt atattaattt gatacaggat atttatgagg caacaaagtt tcatcctgct   11700
ccttcccctg tcttggatgc ttctggaact gatagggttc ttttgacctc catcaaatgc   11760
tctatacatc aaatttctgc aacacttcgc aataagtatg acgtattaat taattaatta   11820
aatatctaat tatctaatta tctttatagt tttgtaagac ttacttcttt tttctaggaa   11880
gttggatcga gctattggtg aagtggtttt tgaggggaat gttgtggagt gcatgatttg   11940
ggaggaatct gctgttgtta ctgcatcaat caattctgta gagatgatta atccattaaa   12000
caatcaagcc attttactta ttaaaagggt gtgtgttctt tttgtttttg ttacatggaa   12060
agtcttgagt tatttatttt tgaatctttt tctatttctt tcaggtcatc tctgaggaga   12120
gttttcttga agaggagaaa ccgtctttaa atatccaagc ttacattcca caagcaaatc   12180
gtgagggtga cttgacattg aaggtacccc accttgcatt ttttgaaaaa tattttcttg   12240
tgctataaat ttctgataat tacagtgact cttaaacttc attttaggtt ttgcttgagc   12300
cgattgaagt gacgtgtgat ccaacatatc ttgttaattt catggagcta tatactgtgt   12360
tgggttccta tacctctcat gaagaaaggg tcagttttta catttctcaa agtagatttc   12420
ttttaagaac cttctggaag atgcagattg gaagttatat ctagatagtg aattcaatgt   12480
ttctcatata aaaacactga acatacttta ccttatgaga ttttgaataa caacttccat   12540
tagtttaatg ttacaggtcc taaactcgct taatgggata aatgatgtaa agtcacgtct   12600
aatatccaaa gccaagtatg tcatctacta tacccttagg gtctagtaat gggattgata   12660
gcaacttcat gtttaaagct atatctatct cttctcttct tttgttttgc aggtatattt   12720
tgtcaggccg gaagagaatg atgtgggata ttagtttgat aaacatcaag ataaatattc   12780
catgggagaa tgggaactca gagatgcata aattggtaat ttaatttctt attacatggt   12840
ctacaaactc acattatttg cattaacttt aaacaaaaac atccaggtac ttgaattaac   12900
agctgtcacc tttgcatcca agcgcgatat cggctctttt gcaccagata tcaatgtacc   12960
atctcaattc atgaggaatc tgattgatga caattcttca aacgagcttc tagaaggaac   13020
tcacattcaa gatctgtacg atctcttgga aatcaaaata atcgacttcc aggtcagcat   13080
atcccatcat ctctcatctt tcacatcact gatgtttgac tttgactttg actttgactt   13140
cctgcagata aacttgtttg tgcctttcta tccatatact tttcctatct tggagaaact   13200
caatgcctct tctgctttat catggtgcat tgttcaggac gaatctttac taaaagcact   13260
agaggtaggt aaacggtaaa tctcacattt actaattact gttgattttt ttggcacact   13320
ttttaccatc aataattggt ttcaggttta tgtattggtg gctaccettt tggcacatgt   13380 gtcaccatca ataattggct cattttagga actagttgaa agcatgaaca tgctgcatca   13440
tacttcacaa ttgggcgcca catcagcaac ctcgtcaatt gaaccaagga actctagcag   13500
tatctctgtt attgctaatt tggagtctgc tagcatcatt gttgaccttg aaaatggctt   13560
agaagctagc tgcacactaa ctgtgtctct tcaggacttg gatatgagga tgggtagtat   13620
gaaatccaca caatctttct ggatatgtac aagggattta aaagtaactt ctcggttgtt   13680
```

```
ggaaagtggt gatgacctgg accttataat atgtctgcct caaagtactt cacctaatga   13740
tgggtgtctt gtgctacatt atgatggtaa tttgagcata tgtttgagtg atttggatct   13800
tcattgctat ccacatattg ttggattgct ggttgagttt tctggaaagc tatccacata   13860
tagtccttca aatgccaaaa atcaagattt tgtggacagt aacagtaaca ctatactctc   13920
agattcttat atagacttcc agaggtttgg ttgttccaaa atttcagtta atcattaccc   13980
ttttgttaca atatacaatg acagatctct tcttaacctc gatacttcac ttattaacat   14040
caagaaggtt cataagacaa atagttcaaa gttgagggca aaaaggata atcatcaagt   14100 aggtgctcta gttgtaatga atcttgatct caacagcatt agactacatc ttcatgactc   14160
ttcatccatt gttgcatctg ttacacttcc tgtttccaaa tcctcttttg ctatccatga   14220
gaactttctg gatgtgttat tttcaactga gggattgagt ctttcatcac agtggtatcc   14280
tcagactcta caagactctc tgtggggccc tgcttcactg aatctttctc cagtgatcaa   14340
cattcgtgtg agaaaaggga accatggaat cgaactggat tttagtgttc aaaatgtttc   14400
ctgcatattg ccaactgagt tcctggctgc actcattggt tacttctcat tgcctgattg   14460
gagctactca aatccaaatg agtcatcacc tactactacc aacaccaata ccaataacaa   14520
cagcatcagt ttcacttaca agtttgagat attggactcg gttttattta cacctgtggc   14580
taatcctgat cacgagtttta taaagcttaa tattccacag atgtactgca cattcattga   14640
tagcattgat tcagacactc tgttgaaaga aatccctta gagtgctctg ttccagttgg   14700
atttactgga aatcagaatt attgtctgaa tgtatttggg agggatttat ctctacatca   14760
tattatttgt cgaaaagaca atgcttctga agtgacaagt gtcagcttga tcgcgccttt   14820
tagtggcgat atatggatca caataccata tgaatctaat tcttcttatg caacatgtat   14880
catgtcaagg gttagtaaat gtcagtttac tgttgaaggt aaatatttttc taccaaactc   14940 tgagttttgt tcatgtttga tacttgatta atgcaatggt gtttcatttt tccaggaaga   15000
gaaatacttg gctgcattgg agcattacag gatgttgtcg accaattctc atctgttggc   15060
aatctatcca cttgtttcac ttctgatgtc tcagagtttc tcaatttaaa agaaaattat   15120
gtggttccag ttcccattga atcttcaact gtcagcttta cagaaatcag atgctctgtt   15180
caatccatgt cagtagaact ttactctgac aagatgaatg gtaacagact tatcgccaaa   15240
tccgacatga aattcgcatg tggaatatca atgaaaacag acaagcctct ttctcttgat   15300
atatcattca cttgtttcac actttcctca cttcttacct ctgttgtctt actggaatgc   15360
acatcatgta ccaaaaatgt accggttctc aacatgcagt tcttgatgtc agatgatggt   15420
aaaaaccacc tgcgattctc ccttccttgt gttaacattt ggttgttctt gtctgaatgg   15480
agtcaagttt tgacctggt caattcttgc tgtgaacctg caatccagaa tgaggaaccg   15540
gaaaaatcca catcagctcc ggtttctcgt gttgatactg cagaaaactc acctcaatcc   15600
accactgtct ccagctatcc atctttagaa gatcggtttt cattaaccgt aaagtcggat   15660
cttattggtg taaaaatccg tattcctgtt caagtttctg gagaagtagt taaatacttt   15720
ggggccccac aagttcgaga gcagagttta gttacaggaa gagatcacgg aagttttctg   15780
tttatttatc tacaaagtag gtgcactgag gtgaacatga agggcgaaac ggtaaatttg   15840
aagtcgaatc tggggaaagc aatgggaaca gttgaactgt tcagaacaa gagtgtccat   15900 tcttggcccc ttttcagtt actggaaatc gatatagaag ccgaatctgg taatgatgat   15960
atggaccgca tgcatttaaa gacagagatt cactgtgata atcttgatgt ttggctctca   16020
```

-continued

```
catcatgcat tttacttctg gcaaactatg ctgtttatgt ttccggaagg ttccggatcc    16080
gaatctcctc aacttccagt tggcagtgtc aatttcagat tccacttacg aaaactctcc    16140
attcttttaa cagatgaaaa ggtatgtaaa ctgtaaactg taaagtaaac tgttttctca    16200
tattaaaaaa tataatgaaa ctaatttcaa gttttaatt agtggagctc caatggtcct     16260
ttattggaga ttctcatggg aagtttgtta tttcacggaa tcataactgc aaacatgatg    16320
gaagggtcaa tcgacagtga ccttcaagtc aactacaaca acatccataa agtcctatgg    16380 gagcctttc tcgaaccatg gaagttccaa ataaccttaa gaagacaaca aggaaaaagc     16440
accctcgaga acagtccagt catgaccgat atccgcctcg agtcatcaac aaacctcaac    16500
atcaatgtca ccgaatcctt catcgaggtc gctttcagaa cattcgacat gatcaaagac    16560
gcctcagatc tcataagtct taacattctt cctgaaaaca attcaagatt gacaaaaccc    16620
catacaaatg aaaacacact cgcgaataga tacgccccctt acacactcga aaacttgaca   16680
tcacttcctc tggtatttta catctcaaaa ggtgaggggt tcaatatgac atcattgaaa    16740
gatggaaaac acgtgcagcc aggctgttca tatcccgtga atattgataa caacccggaa    16800
gaacaaacgt ttgggtttag gcctagtcat tctactgaca atctaggtgg cgacatgcaa    16860
ttcgctgatg ctcaacatca ttatatagtt gttcaacttg aaggaacttc tacactttcg    16920
gctccagttt ctattgatct tgttggtgtc agcttctttg aggtggattt ttctactaat    16980
ataggacttg atgtttctaa aggtggctat gttgttcctg tagtaatcga tgtttcagtc    17040
caacggtaca caaagctagt ccgcttgtac tcaacggtac gtttatttct ttccactcct    17100
aatatatata tacatatata tatatatata tattgatgtg atgacgtggc aggtcatact    17160
gacgaatgca acatcaatgc catttgaagt acggttcgat atcccatttg gtgtatctcc    17220
caagattcta gaccctgtat accccggcca tgagtttcct cttcctctac atttagcaga    17280
atcagggcga ataagatggc gtccattagg aagcacttac ctatggagtg aagcttacag    17340
catttcaaat attctctcaa atgaaagcaa gattggacat ttgcggtcgt ttgtctgtta    17400
tccttctctt ccaagtagcg accccctttcg gtgttgtgtg tccgttcatg atgtgtgttt    17460
gccatctgct ggaagggtaa taaacaagag gggatcatct tcatctctgt ataatattaa    17520
tactcatgat catggtgaca agatagagaa ccaggatctc tcgaataaga ggtgtattca    17580
cttgattact ttgagtaatc ctttgatagt gaaaaactat ttgccagttg aagtgtctgt    17640
ggtgattgag agtggtggag tttcacgtag catgctgctt tcagaggttg ttatcagtta    17700
tcttattata aactttgaca ttttcttaat gtattgtttt ataacatatg caggttgaaa    17760 cttttttta tcatattgat tcttcacatg atctttcgtt aacttttgag atacacgggt     17820
ttagaccttc tcttttgaag tttccacgtg ctgaaaagtt cagtggaatt gctaaattca    17880
gtggaacaaa gttttcttct tcagaatcca tcaactttgc tgctgataat tctaaaggtg    17940
ctgcacactt acttttctca tctccctttt tctctcttac attaaaagaa gctgatgtgt    18000
ctttgtttag gtccattata tgtgacaatg gaaaggtga tggatgcatt ctctgggct      18060 cgtgaaatct gcatatttgt gcccttctta ttgtacaact gctgtggttt tccccttacg    18120
attgcaaatt cgactaatga tctcacaatg cgtgacactt tgccttcatg ttatgatttg    18180
gatgaagagg acccgttttt gggcaaaaaa gatggtctaa gccttttgtt ttccaaccaa    18240
gtttccaata atgatcctat gagtaatctt gttccacta gaaaggaatc tttcacctca     18300
tctggatcaa ccaaaaaaaa catcggcaca caaaaaccgt ctttacacga tcaggaaaaa    18360
agtcaacttt cgcatagtca acaacttgac tttgacgaaa caactcgcaa aaaagtcaac    18420
```

```
ttccgcatgt attctcccga ccctaacatc gcttcgagtg agatcatggt gagagttagt    18480
cgatgccggt ctgatgctga catggcaagt acctcagact acacgtggtc cagtcaattc    18540
ttcctggtcc caccagccgg ttcaaccaca gtccttgtcc cccgatcatc aaccaatgct    18600
tcatatgtat tatcagttgc ctctagtgct atttccgggc catattctgg aaggacaagg    18660
attatcaatt ccagcctag atacgttatc agtaatgcat gcagtcagga cttgtgctat     18720
aggcagaaag gttccgactt tatataccat ttgaaagcag acaacactc ccatatccat     18780
tggacagaca taacaaggta catcaatcat tttcccctaa ctttctgtta ccaaattcac    18840
atgcttatgt ggcagttgca taaaataaaa cagggagtta ctggtgtctg ttcgtttcga    18900
tgagccaggg tggcagtggt caggctgctt ttttccagaa catctaggtg atacacagct    18960
gaagatgaga aactatgtta gtggtgcagt tagtatggtt cgtgtagagg tccaaaatgc    19020
tgacgatgca atcagagatg acaagattgt tgggacccct catggtgaat ctgggacaaa    19080
tttgattctt ttgtctgatg atgatactgg ctttatgcca tacagggttg ataatttctc    19140
aaaggaggtt agttacttac tccattcttc atttctaatt ctttccattt gatctatgat    19200
ataagtttgg tgaaatgttg ccagaggtta cgtatttacc aacaaaaatg tgaagcattt    19260
gagactgtta tacattcata tacgtcttgc ccttacgcat gggatgaacc ctcctaccca    19320
catcgtttaa ctgttgaggt atgcatttga tttaaaaaca gttggctatt aaattattca    19380
tatattcatt ctgttgttaa atctccaagg tgtttgctga gagggtagta gggtcttaca    19440
ctctagatga tgctaaagag tacaaacctg tggttttacc ttcaacctcc gaggtaaatt    19500
tgtaattttt acaaacatgg atgggttaaa tctgtaacta actactcttt catgatttct    19560
tttggtagaa acctgaaaga aggttgctaa tatctgtcca tgctgaagga gcattgaagg    19620
tcctgagcat cattgattca agctatcata tatttgatga tgtaaaaatc ccacgttctc    19680
ctcggttaac tgagaaaaga gaatacgacc aaaaacaaga aagttcactt ctttatcaag    19740
aaagagtatc gatttccatt ccattcattg ggatttctgt tatgagctct caaccacagg    19800
taccattact ttatacaaat atcttgtcta tatgtggtga atttcaccat tcttataaaa    19860
tgtattttgt aggagttgct ttttgcatgt gcaaggaaca caatgattga cctggttcaa    19920
agtctggacc agcaaaatct ttccttgaaa atctcctctt tacagattga taaccaactg    19980
ccaaccacac cctaccccgt tatattatct ttcgaccatg agtataaaca actcccaacc    20040
tctcagataa aaacaaaga tgagcctgtg ttctcattgg ctgcagcaaa atggaggaat    20100
aaagatagag ctttgctttc attcgagcat ataaacttaa ggtacatgat tataacaata    20160
tgtcaataaa tagacagtca gaaattagtc aattactgag aattttggtt gttgcagaat    20220
ggcagatttc catcttgagc ttgaacagga tgtgatttta agtctgtttg atttctccaa    20280
ggcagtatcc tcaaggttcc atagcagagg aatgccacat atggattcag tcgtgcatcc    20340
tctttcctca aacttgagtg gaaataaagc aactaaattg gctgaaaaga ctgaaattga    20400
gggtgaaagt ttccctcttt taccatcaat agtgccaatt ggtgcaccat ggcagaaaat    20460
atatctcctg gcaagaaaac agaagaaaat atatgtggaa cttcttgaag tggcccccat    20520
cactttaacc ctaaggtaag acgatcgaca ctcagagggg catatgtgta aatgtgttga    20580
attggtcttt ttttcctgca gcttttcgag cagtccatgg atgctaagga atggaatact    20640
tacatcagga gaatatctta tccatgtaag tgtgaccatt ggaatagggt tactgatagt    20700
agtaaagagt aatttgtatg ggattgcaga gaggtctgat ggctcttgct gacgtggagg    20760
```

```
gagcacggat ccatctaagg cggttaacaa tctctcatca gttggccagc ttggaatcca    20820
tacgagagat cttaatcata cattataccc gccaacttct ccacgaaatg tacaaggtta    20880
gattacatct ctacatatat aaatcttcaa ttgtgattat ttttcttttt cttcttcagg    20940
tatttggttc agctggggta ataggcaacc ccatgggttt cgcaagaagt gtaggacttg    21000
gcatccgaga cttcctctca gttccagcca gaagcttcat gcaggtaata aataaataat    21060
taaatattaa atccaagtta attagtaatg tcaattttaa ttatatcgca gagccccgca    21120
ggacttatca cggggatggc acagggaact acaagtcttc taagcaatac ggtttacgcc    21180
ataagtgatg ctgccaccca agtcagtaga gccgcacaca aggtatatat atatatacat    21240
tatattatac ttttctcaat tctaagattt catcatttac ttgaagggca ttgttgcatt    21300
tacaatggac gaccccccat ctgcagcaga aatgggcaaa ggtgtaataa atgaagtttt    21360 ggagggggctg actggtcttc tccaatcacc aataagagga gctgaaaaac acgggcttcc    21420
aggagtcctt tcaggtatag cactaggagt aacgggtcta gtggcaaggc cagccgccag    21480
catactggaa gtaacagaaa aaaccgcccg cagcataaga aaccgaagca aactctacca    21540
catccgcctc cgggtccgcc tcccgagacc gctaaccccc aaccaccacc cgttaaaacc    21600
ctactcgtgg gaccaagcag tcggcctctc cgtcctcacc aataccaatt ccaattccga    21660
ttccgacctc aaagacgaaa ccctcgtcct ctccaaatcc ctcaaacaaa agggcaaatt    21720
cgtcattatc acccaacggt tactcctcat tgttacctcc tcgagcctaa cgaatttagg    21780
tcaacccaat ttcaaaggcg tccctgcgga ccccgattgg gtggttgaag ccgagataac    21840
gttggatagt gtgatacacg tggatgttga tggagaggtg gtgcatattg tcgggagtag    21900
ttctgatgtg gtggttagac agaatgttgg tgggaagcag cggtggtata atccgttgcc    21960
gctgtttcag acgaatttgg agtgtttagg aaggaggag gcggggggagt tgttgaaggt    22020 gttgttggtg acgattgaga gagggaagga gagagggtgg ggccgggggt gtgtgtaccg    22080
tctgcatcag agtaatgtta ggtgatgtat atttttttc tacatataaa gttactatag    22140
gagaaaaagg actggatatt atattataca tacctgaaac aaggaaacgt tttctttcaa    22200
aattttggct gtattattat tttgtcgacc atgttgggct aaaatggcca attatttact    22260
tatgacatgg ttaaaaaata ttggtgtctt gttttgtata attacaattt atattagtat    22320
cgatgcaatg taagattgta gaaagcgcta ccgtataaaa caacataagt catgaggtta    22380 cacccctagtg gggtcaaggg aacaaaaaca ttttaaacgt ttttcagatt tgcatttcca    22440
gccgcctata actaccattc taattcttat ccgacatctt aacacgatat agggattttt    22500
actttacttg tcaaaacttg aagttgacag tttgataata tccagtcctc ttttccaata    22560
gtaacttttc cagccgccca taactatcat tcttttctttg ttataactat gttctatcta    22620
atttagttgt tttttattat ttttgataaa aatatgtttt agttgtttct gattttgttt    22680
atatttaatt attattgttt tttttgctaa aacatatcaa atttgttttg aattttgtct    22740
atgtatagtt tttatgataa attatttgta aatttagccg gttaaaatga attttcggc    22800 caagcatgaa catttcgatg aacgaacgca catgcttttt ataggttatc tacttgagca    22860
cgtgcttcaa tttcatattt gcattcaata atccattgaa ctacttgtaa ttttgctcta    22920
gttccttgcc agagtggttt tctttattat agggatattt tcatttatat ggtgacttt    22980 tctaaaaaag gtaaacattt ttttagattt gcaaataatc ggtcataagg actggaaaaa    23040
tcaaaaacaa caatgatgca ttttactaaa aaaaacaata gtgacaaaat atgaacaaaa    23100
tcagaaataa tgacgtttta cataaaaaat aacgactaaa tatagacaaa acgagaacta    23160
```

```
agttatcctt gtaagttatt atccctgat tatattatca aacaaatttc gtatgacaca     23220
atacaggtct aaaaacctac ctcaactact tacatccgcc aaaatttaca tcttatctat     23280
tcatattaaa cctatacttt gaaattttga actccatgaa ttaaatgcta aaatttctaa     23340
aatgatgaaa accctaattc a                                               23361

<210> SEQ ID NO 2
<211> LENGTH: 11799
<212> TYPE: DNA
<213> ORGANISM: Taraxacum officinale

<400> SEQUENCE: 2
atgtcagatc tgataaactg taagcaacct catgaatcac ccactcctgc cgccacaacc       60
acagccgaag cttcatttga gcccctggat gaaaatctct tctcggatct aaccccactc      120
tgttatttac tccaatccac ctcccccaaa tcaccccaa cattaatctt cctccgttc       180 taccaccacc aatcctctca agattcatcc tttctcatcg ccgtgacgtt ttccagcaaa      240
acccatgtcc accaccgccg ccgtcaaacc agtccggaaa ttcccgccat cgtgcccgga      300
tgtaaccccg ccgtcaaacc agtccggaaa tcaacaacac aaccccctgt tttgcatcac      360
cagagcttga atccgggtcg tggagttcga tttaaactat cttcaactca aaatctggta      420
acattagcag ctagttccac caatcatacc cctgatttcg attctaggtt tccaaatcac      480
gattcctcat acatgaacaa ctggtctaat caagaagaag acaacgacga tgggtgtctt      540
gatgactcta caattaatga aacctcgatt catccgggag tgatactaaa gaggattcaa      600
gcacaaaaag gcattgagtt taaacggagg agaaaatatg ccatggccag ctcacccgct      660
gtcgccatcc cagccagcat tagcccagcc gtcgctcaca tccaccgaaa agctgatttc      720
cacatcgtcg ctcccggccg tcacctacac gtaggttcgg ctccgaagaa agtggtcgat      780
aagctagaag ggataagaag aaggttctta tggggcggta agaagtcgga aaaaagatt      840 cactgggttt cgtgggagaa ggtgataaaa tcaaaagata agaaggttt aggggtgaat      900 ggattgagca gcatgaatat ggccttgcta gtgaaatggt tttggcggct caaaactgaa      960
agggacagcc tgtgggttag atgtgtcacg gcttgtcata atatcaaact tattgatggg     1020
aaacgggtgg ctaaagcttc cttgaaagga gtatggtgga acatcatgag ctgtgttgaa     1080
gagttaaaaa cgaaaggaat ttctgtggag tcaaagttag taaggcaact gggaaacggc     1140
aaacacacgc attttttggaa ggatagatgg ttacacaaca aagttttaaa agatgacctt     1200
ccggagttgt acaaaataga aggggacaaa aattgtatgg taaaccaaag actggtttgg     1260
gacaacaacg agaaaatatt caagcaagct tgggactgga aagaccgat caggagagga     1320 agagaaacca aagaactcga aactttaata attttgacaa atgggataca attaaaggaa     1380
atagaagata attggagatg gaaggaggga tcggacggga aattttcggt gggaaaattg     1440
aggaaactct tgcttatca ggagcaggcc gaggttgatg gtggattcga ttggatcaat     1500
tgggtcccct tgaaggaaga agaggaaacc gaacatgctt ttttcaggtg tgcacatgcg     1560
catcaggtgt gggactggtt caagatgtgg tcgggtctga tgcgggaaat ccctctaaac     1620
ttcagatcca tggaggcgga gatcaaggct ggtgctggtg acaaaaaatc ggtgaaacta     1680
ggaatggctt tggcttatgt gatgctgtgg actatctgga aaatcaggaa tggtgcagtc     1740
ttcaacaaca gaaaagcgag ggcaatgaac acgacggatg agaaatccat ctcctaccgg     1800
ccgacttcac cagcggcggc tccctctcca tctccggcgc cctctccagc gaccgctccc     1860
```

```
tctccaccgg cgacgtcttc tccagagccg gcgacccaca gccccatgct aattggcact    1920
gaggaaatgt ttgaaggttt agtacggcag ctgatattag ttatcttgg  ccaatatatt    1980 aaagatatac acagagaaca actcaagatc acactgtgga atgaggaagt gttttttggaa   2040 aatgtggagt taattctgga agcttttgat tatcttgaac ttccgtttgc tctaaagcaa    2100
ggacgggttg ggaggctaag cattagaatt ccttggaaaa agcttggttg ggatcctatt    2160
ataataatct tagaggatat attagtttgt gcctctcaac gtgaggatga agagtggagt    2220
gttgatgatg ttgaaagacg agaattttct ggaaaaaagg ccaaacttgc tgcagcagaa    2280
ttggcaaagt tatcgcaacg tgtatgtgat aatcagactg ggaaatcatt tatgtcatac    2340
attactgcca agattattga tggcattcaa gtcaccatca ggaatgtcca tatcgtatat    2400
agagatattt caaatgaaaa atcccaaact gtatttggtg tgaagttggc tagtttgact    2460
gcaatgaagc aaaactatgc tggggtatta agtggaaagg tgagagttgg ccaagtaaac    2520
aaaattgttg agatacaagg tttgaaaata tactgtaaaa cctttcatgg atcttcaaca    2580
gacatccata ctgaaaatgg tgaagactcc atggcaatgg tggctgcaag ttatgataat    2640
gatgaacatg ctcacttgtt ggccccagtc aacgtatctg cttctctttc ggtgaatagg    2700 tctgaaggc tggagaataa tgcagcacaa tactcggttg atattgagtt gtctggcttg     2760
gtattgtccc tagatgaaga tcagttgcag caaatactgt atctatatga atatctatgc    2820
acatgtcggc taagagagaa atatggacga tatcgtcctt gggggaaacc tatatcagag    2880
agacaattgg gatggcagat acagtggtgg cattatgctc aacactctgt gttatctgat    2940
gttcgtaaaa gactgaagaa aacttcatgg aaataccttg gagaacgtct aggcagaaaa    3000
cgacggtatg taaatctgta caaattgaaa ctcgaatgtc ttcgaaaaga acagcctttg    3060
gatgatgaaa ttgtaatgga gttggaccaa atggagaaag tgtctgatat agaagatata    3120
ttgagttaca gatctgctgc tgagaatgaa cttcaggagt tcttggtgga ttcaccttct    3180
ggtattggag gtagtgaagt gaatactacc attgacaagt caatggatga tgaccaaaca    3240
tctggcaaac cgcaaggatg gttgaaatgg ctgtcccgtg gtatgctagg tgctggaggt    3300
acagacgatt ccagccagtt ttctggtgtt gtttcagatg aagtaatcaa ggatatttat    3360
gaggcaacaa agtttcatcc tgctccttcc cctgtcttgg atgcttctgg aactgatagg    3420
gttcttttga cctccatcaa atgctctata catcaaattt ctgcaacact tgcaataag    3480 aagttggatc gagctattgg tgaagtggtt tttgagggga atgttgtgga gtgcatgatt    3540
tgggaggaat ctgctgttgt tactgcatca atcaattctg tagagatgat taatccatta    3600
aacaatcaag ccattttact tattaaaagg gtcatctctg aggagagttt tcttgaagag    3660
gagaaaccgt ctttaaatat ccaagcttac attccacaag caaatcgtga gggtgacttg    3720
acattgaagg ttttgcttga gccgattgaa gtgacgtgtg atccaacata tcttgttaat    3780
ttcatggagc tatatactgt gttgggttcc tatacctctc atgaagaaag ggtcctaaac    3840
tcgcttaatg ggataaatga tgtaaagtca cgtctaatat ccaaagccaa gtatattttg    3900
tcaggccgga agagaatgat gtgggatatt agtttgataa acatcaagat aaatattcca    3960
tgggagaatg ggaactcaga gatgcataaa ttggtacttg aattaacagc tgtcaccttt    4020
gcatccaagc gcgatatcgg ctcttttgca ccagatatca atgtaccatc tcaattcatg    4080
aggaatctga ttgatgacaa ttcttcaaac gagcttctag aaggaactca cattcaagat    4140
ctgtacgatc tcttggaaat caaaataatc gacttccagg acgaatcttt actaaaagca    4200
ctagaggttt atgtattggt ggctacccct ttggcacatg tgtcaccatc aataattggc    4260
```

```
tcattttag aactagttga aagcatgaac atgctgcatc atacttcaca attgggcgcc    4320
acatcagcaa cctcgtcaat tgaaccaagg aactctagca gtatctctgt tattgctaat    4380
ttggagtctg ctagcatcat tgttgacctt gaaaatggct tagaagctag ctgcacacta    4440
actgtgtctc ttcaggactt ggatatgagg atgggtagta tgaaatccac acaatctttc    4500
tggatatgta caagggattt aaaagtaact tctcggttgt tggaaagtgg tgatgacctg    4560
gaccttataa tatgtctgcc tcaaagtact tcacctaatg atgggtgtct tgtgctacat    4620
tatgatggta atttgagcat atgtttgagt gatttggatc ttcattgcta tccacatatt    4680
gttggattgc tggttgagtt ttctggaaag ctatccacat atagtccttc aaatgccaaa    4740
aatcaagatt ttgtggacag taacagtaac actatactct cagattctta tatagacttc    4800
cagaggtttg gttgttccaa aatttcagtt aatcattacc cttttgttac aatatacaat    4860
gacagatctc ttcttaacct cgatacttca cttattaaca tcaagaaggt tcataagaca    4920
aatagttcaa agttgagggc aaaaaaggat aatcatcaag taggtgctct agttgtaatg    4980
aatcttgatc tcaacagcat tagactacat cttcatgact cttcatccat tgttgcatct    5040
gttacacttc ctgtttccaa atcctctttt gctatccatg agaactttct ggatgtgtta    5100
ttttcaactg agggattgag tctttcatca cagtggtatc ctcagactct acaagactct    5160
ctgtggggcc ctgcttcact gaatctttct ccagtgatca acattcgtgt gagaaaaggg    5220
aaccatggaa tcgaactgga ttttagtgtt caaaatgttt cctgcatatt gccaactgag    5280
ttcctggctg cactcattgg ttacttctca ttgcctgatt ggagctactc aaatccaaat    5340
gagtcatcac ctactactac caacaccaat accaataaca acagcatcag tttcacttac    5400
aagtttgaga tattggactc ggttttattt acacctgtgg ctaatcctga tcacgagttt    5460
ataaagctta atattccaca gatgtactgc acattcattg atagcattga ttcagacact    5520
ctgttgaaag aaatcccttt agagtgctct gttccagttg gatttactgg aaatcagaat    5580
tattgtctga atgtatttgg gagggattta tctctacatc atattatttg tcgaaaagac    5640
aatgcttctg aagtgacaag tgtcagcttg atcgcgcctt ttagtggcga tatatggatc    5700
acaataccat atgaatctaa ttcttcttat gcaacatgta tcatgtcaag ggttagtaaa    5760
tgtcagttta ctgttgaagg aagagaaata cttggctgca ttggagcatt acaggatgtt    5820
gtcgaccaat tctcatctgt tggcaatcta tccacttgtt tcacttctga tgtctcagag    5880
tttctcaatt taaagaaaa ttatgtggtt ccagttccca ttgaatcttc aactgtcagc    5940
tttacagaaa tcagatgctc tgttcaatcc atgtcagtag aactttactc tgacaagatg    6000
aatggtaaca gacttatcgc caaatccgac atgaaattcg catgtggaat atcaatgaaa    6060
acagacaagc ctctttctct tgatatatca ttcacttgtt tcacacttttc ctcacttctt    6120 acctctgttg tcttactgga atgcacatca tgtaccaaaa atgtaccggt tctcaacatg    6180
cagttcttga tgtcagatga tggtaaaaac cacctgcgat tctcccttcc ttgtgttaac    6240
atttggttgt tcttgtctga atggagtcaa gttgttgacc tggtcaattc ttgctgtgaa    6300
cctgcaatcc agaatgagga accggaaaaa tccacatcag ctccggtttc tcgtgttgat    6360
actgcagaaa actcacctca atccaccact gtctccagct atccatcttt agaagatcgg    6420
ttttcattaa ccgtaaagtc ggatcttatt ggtgtaaaaa tccgtattcc tgttcaagtt    6480
tctggagaag tagttaaata ctttggggcc ccacaagttc gagagcagag tttagttaca    6540
ggaagagatc acggaagttt tctgtttatt tatctacaaa gtaggtgcac tgaggtgaac    6600
```

```
atgaagggcg aaacggtaaa tttgaagtcg aatctgggga aagcaatggg aacagttgaa   6660
ctgtttcaga acaagagtgt ccattcttgg ccccttttc agttactgga aatcgatata   6720
gaagccgaat ctggtaatga tgatatggac cgcatgcatt taaagacaga gattcactgt   6780
gataatcttg atgtttggct ctcacatcat gcattttact tctggcaaac tatgctgttt   6840
atgtttccgg aaggttccgg atccgaatct cctcaacttc cagttggcag tgtcaatttc   6900
agattccact tacgaaaact ctccattctt ttaacagatg aaaagtggag ctccaatggt   6960
cctttattgg agattctcat gggaagtttg ttatttcacg gaatcataac tgcaaacatg   7020
atggaagggt caatcgacag tgaccttcaa gtcaactaca acaacatcca taaagtccta   7080
tgggagcctt ttctcgaacc atggaagttc caaataacct aagaagaca acaaggaaaa   7140 agcaccctcg agaacagtcc agtcatgacc gatatccgcc tcgagtcatc aacaaacctc   7200
aacatcaatg tcaccgaatc cttcatcgag gtcgctttca gaacattcga catgatcaaa   7260
gacgcctcag atctcataag tcttaacatt cttcctgaaa acaattcaag attgacaaaa   7320
ccccatacaa atgaaaacac actcgcgaat agatacgccc cttacacact cgaaaacttg   7380
acatcacttc ctctggtatt ttacatctca aaggtgagg ggttcaatat gacatcattg   7440
aaagatggaa aacacgtgca gccaggctgt tcatatcccg tgaatattga taacaacccg   7500
gaagaacaaa cgtttgggtt taggcctagt cattctactg acaatctagg tggcgacatg   7560
caattcgctg atgctcaaca tcattatata gttgttcaac ttgaaggaac ttctacactt   7620
tcggctccag tttctattga tcttgttggt gtcagcttct ttgaggtgga tttttctact   7680
aatataggac ttgatgtttc taaaggtggc tatgttgttc ctgtagtaat cgatgtttca   7740
gtccaacggt acacaaagct agtccgcttg tactcaacgg tcatactgac gaatgcaaca   7800
tcaatgccat ttgaagtacg gttcgatatc ccatttggtg tatctcccaa gattctagac   7860
cctgtatacc ccggccatga gtttcctctt cctctacatt tagcagaatc agggcgaata   7920
agatggcgtc cattaggaag cacttaccta tggagtgaag cttacagcat ttcaaatatt   7980
ctctcaaatg aaagcaagat tggacatttg cggtcgtttg tctgttatcc ttctcttcca   8040
agtagcgacc cctttcggtg ttgtgtgtcc gttcatgatg tgtgtttgcc atctgctgga   8100
agggtaataa acaagagggg atcatcttca tctctgtata atattaatac tcatgatcat   8160
ggtgacaaga tagagaacca ggatctctcg aataagaggt gtattcactt gattactttg   8220
agtaatcctt tgatagtgaa aaactatttg ccagttgaag tgtctgtggt gattgagagt   8280
ggtggagttt cacgtagcat gctgctttca gaggttgaaa cttttttta tcatattgat   8340 tcttcacatg atctttcgtt aacttttgag atacacgggt ttagaccttc tcttttgaag   8400
tttccacgtg ctgaaaagtt cagtggaatt gctaaattca gtggaacaaa gttttcttct   8460
tcagaatcca tcaactttgc tgctgataat tctaaaggtc cattatatgt gacaatggaa   8520
aaggtgatgg atgcattctc tggggctcgt gaaatctgca tatttgtgcc cttcttattg   8580
tacaactgct gtggttttcc ccttacgatt gcaaattcga ctaatgatct cacaatgcgt   8640
gacactttgc cttcatgtta tgatttggat gaagaggacc cgttttgggg caaaaaagat   8700
ggtctaagcc ttttgttttc caaccaagtt tccataatg atcctatgag taatcttgtt   8760
tccactagaa aggaatcttt cacctcatct ggatcaacca aaaaaaacat cggcacacaa   8820
aaaccgtctt tacacgatca ggaaaaaagt caactttcgc atagtcaaca acttgacttt   8880
gacgaaacaa ctcgcaaaaa agtcaacttc cgcatgtatt ctcccgaccc taacatcgct   8940
tcgagtgaga tcatggtgag agttagtcga tgccggtctg atgctgacat ggcaagtacc   9000
```

```
tcagactaca cgtggtccag tcaattcttc ctggtccnac cagccggttc aaccacagtc   9060
cttgtccccc gatcatcaac caatgcttca tatgtattat cagttgcctc tagtgctatt   9120
tccgggccat attctggaag gacaaggatt atcaatttcc agcctagata cgttatcagt   9180
aatgcatgca gtcaggactt gtgctatagg cagaaaggtt ccgactttat ataccatttg   9240
aaagcaggac aacactccca tatccattgg acagacataa caagggagtt actggtgtct   9300
gttcgtttcg atgagccagg gtggcagtgg tcaggctgct ttttccaga acatctaggt    9360
gatacacagc tgaagatgag aaactatgtt agtggtgcag ttagtatggt tcgtgtagag   9420
gtccaaaatg ctgacgatgc aatcagagat gacaagattg ttgggaaccc tcatggtgaa   9480
tctgggacaa atttgattct tttgtctgat gatgatactg gctttatgcc atacagggtt   9540
gataatttct caaggagag gttacgtatt taccaacaaa aatgtgaagc atttgagact    9600
gttatacatt catatacgtc ttgcccttac gcatgggatg aaccctccta cccacatcgt   9660
ttaactgttg aggtgtttgc tgagagggta gtagggtctt acactctaga tgatgctaaa   9720
gagtacaaac ctgtggtttt accttcaacc tccgagaaac ctgaagaag gttgctaata    9780
tctgtccatg ctgaaggagc attgaaggtc ctgagcatca ttgattcaag ctatcatata   9840
tttgatgatg taaaaatccc acgttctcct cggttaactg agaaaagaga atacgaccaa   9900
aaacaagaaa gttcacttct ttatcaagaa agagtatcga tttccattcc attcattggg   9960
atttctgtta tgagctctca accacaggag ttgcttttg catgtgcaag gaacacaatg   10020
attgacctgg ttcaaagtct ggaccagcaa aatctttcct tgaaaatctc ctctttacag   10080
attgataacc aactgccaac cacaccctac cccgttatat tatctttcga ccatgagtat   10140
aaacaactcc caacctctca gataaaaac aaagatgagc ctgtgttctc attggctgca    10200
gcaaaatgga ggaataaaga tagagctttg cttttcattcg agcatataaa cttaagaatg   10260
gcagatttcc atcttgagct tgaacaggat gtgatttta gtctgttga tttctccaag    10320
gcagtatcct caaggttcca tagcagagga atgccacata tggattcagt cgtgcatcct   10380
ctttcctcaa acttgagtgg aaataaagca actaaattgg ctgaaaagac tgaaattgag   10440
ggtgaaagtt tccctctttt accatcaata gtgccaattg gtgcaccatg gcagaaaata   10500
tatctcctgg caagaaaaca gaagaaaata tatgtggaac ttcttgaagt ggcccccatc   10560
actttaaccc taagctttc gagcagtcca tggatgctaa ggaatggaat acttacatca    10620
ggagaatatc ttatccatag aggtctgatg gctcttgctg acgtggaggg agcacggatc   10680
catctaaggc ggttaacaat ctctcatcag ttggccagct tggaatccat acgagagatc   10740
ttaatcatac attataccccg ccaacttctc cacgaaatgt acaaggtatt tggttcagct   10800
ggggtaatag gcaaccccat gggtttcgca agaagtgtag gacttggcat ccgagacttc   10860
ctctcagttc cagccagaag cttcatgcag agccccgcag gacttatcac ggggatggca   10920
cagggaacta caagtcttct aagcaatacg gtttacgcca taagtgatgc tgccacccaa   10980
ggcattgttg catttacaat ggacgacccc ccatctgcag cagaaatggg caaaggtgta   11040
ataaatgaag ttttggaggg gctgactggt cttctccaat caccaataag aggagctgaa   11100
aaacacgggc ttcaggagt cctttcaggt atagcactag gagtaacggg tctagtggca    11160
aggccagccg ccagcatact ggaagtaaca gaaaaaaccg cccgcagcat aagaaaccga   11220
agcaaactct accacatccg cctccgggtc cgcctcccga gaccgctaac ccccaaccac   11280
cacccgttaa aaccctactc gtgggaccaa gcagtcggcc tctccgtcct caccaatacc   11340
```

```
aattccaatt ccgattccga cctcaaagac gaaaccctcg tcctctccaa atccctcaaa    11400
caaaagggca aattcgtcat tatcacccaa cggttactcc tcattgttac ctcctcgagc    11460
ctaacgaatt taggtcaacc caatttcaaa ggcgtccctg cggaccccga ttgggtggtt    11520
gaagccgaga taacgttgga tagtgtgata cacgtggatg ttgatggaga ggtggtgcat    11580
attgtcggga gtagttctga tgtggtggtt agacagaatg ttggtgggaa gcagcggtgg    11640
tataatccgt tgccgctgtt tcagacgaat ttggagtgtt tagggaagga ggaggcgggg    11700
gagttgttga aggtgttgtt ggtgacgatt gagagaggga aggagagagg gtggggccgg    11760
gggtgtgtgt accgtctgca tcagagtaat gttaggtga                          11799
```

<210> SEQ ID NO 3
<211> LENGTH: 3932
<212> TYPE: PRT
<213> ORGANISM: Taraxacum officinale

<400> SEQUENCE: 3

```
Met Ser Asp Leu Ile Asn Cys Lys Gln Pro His Glu Ser Pro Thr Pro
1               5                   10                  15

Ala Ala Thr Thr Thr Ala Glu Ala Ser Phe Glu Pro Leu Asp Glu Asn
            20                  25                  30

Leu Phe Ser Asp Leu Thr Pro Leu Cys Tyr Leu Leu Gln Ser Thr Ser
        35                  40                  45

Pro Lys Ser Pro Pro Thr Leu Ile Phe Pro Pro Phe Tyr His His Gln
    50                  55                  60

Ser Ser Gln Asp Ser Ser Phe Leu Ile Ala Val Thr Phe Ser Ser Lys
65                  70                  75                  80

Thr His Val His His Arg Arg Arg Gln Thr Ser Pro Glu Ile Pro Ala
                85                  90                  95

Ile Val Pro Gly Cys Asn Pro Ala Val Lys Pro Val Arg Lys Ser Thr
            100                 105                 110

Thr Gln Pro Pro Val Leu His His Gln Ser Leu Asn Pro Gly Arg Gly
        115                 120                 125

Val Arg Phe Lys Leu Ser Ser Thr Gln Asn Leu Val Thr Leu Ala Ala
    130                 135                 140

Ser Ser Thr Asn His Thr Pro Asp Phe Asp Ser Arg Phe Pro Asn His
145                 150                 155                 160

Asp Ser Ser Tyr Met Asn Asn Trp Ser Asn Gln Glu Glu Asp Asn Asp
                165                 170                 175

Asp Gly Cys Leu Asp Asp Ser Thr Ile Asn Glu Thr Ser Ile His Pro
            180                 185                 190

Gly Val Ile Leu Lys Arg Ile Gln Ala Gln Lys Gly Ile Glu Phe Lys
        195                 200                 205

Arg Arg Arg Lys Tyr Ala Met Ala Ser Ser Pro Ala Val Ala Ile Pro
    210                 215                 220

Ala Ser Ile Ser Pro Ala Val Ala His Ile His Arg Lys Ala Asp Phe
225                 230                 235                 240

His Ile Val Ala Pro Gly Arg His Leu His Val Gly Ser Ala Pro Lys
                245                 250                 255

Lys Val Val Asp Lys Leu Glu Gly Ile Arg Arg Phe Leu Trp Gly
            260                 265                 270

Gly Lys Lys Ser Glu Lys Lys Ile His Trp Val Ser Trp Glu Lys Val
        275                 280                 285

Ile Lys Ser Lys Asp Lys Glu Gly Leu Gly Val Asn Gly Leu Ser Ser
```

```
                290                 295                 300
Met Asn Met Ala Leu Leu Val Lys Trp Phe Trp Arg Leu Lys Thr Glu
305                 310                 315                 320

Arg Asp Ser Leu Trp Val Arg Cys Val Thr Ala Cys His Asn Ile Lys
                325                 330                 335

Leu Ile Asp Gly Lys Arg Val Ala Lys Ala Ser Leu Lys Gly Val Trp
                340                 345                 350

Trp Asn Ile Met Ser Cys Val Glu Glu Leu Lys Thr Lys Gly Ile Ser
                355                 360                 365

Val Glu Ser Lys Leu Val Arg Gln Leu Gly Asn Gly Lys His Thr His
                370                 375                 380

Phe Trp Lys Asp Arg Trp Leu His Asn Lys Val Leu Lys Asp Asp Leu
385                 390                 395                 400

Pro Glu Leu Tyr Lys Ile Glu Gly Asp Lys Asn Cys Met Val Asn Gln
                405                 410                 415

Arg Leu Val Trp Asp Asn Asn Glu Lys Ile Phe Lys Gln Ala Trp Asp
                420                 425                 430

Trp Lys Arg Pro Ile Arg Arg Gly Arg Glu Thr Lys Glu Leu Glu Thr
                435                 440                 445

Leu Ile Ile Leu Thr Asn Gly Ile Gln Leu Lys Glu Ile Glu Asp Asn
                450                 455                 460

Trp Arg Trp Lys Glu Gly Ser Asp Gly Lys Phe Ser Val Gly Lys Leu
465                 470                 475                 480

Arg Lys Leu Phe Ala Tyr Gln Glu Gln Ala Glu Val Asp Gly Gly Phe
                485                 490                 495

Asp Trp Ile Asn Trp Val Pro Leu Lys Glu Glu Glu Thr Glu His
                500                 505                 510

Ala Phe Phe Arg Cys Ala His Ala His Gln Val Trp Asp Trp Phe Lys
                515                 520                 525

Met Trp Ser Gly Leu Met Arg Glu Ile Pro Leu Asn Phe Arg Ser Met
530                 535                 540

Glu Ala Glu Ile Lys Ala Gly Ala Gly Asp Lys Lys Ser Val Lys Leu
545                 550                 555                 560

Gly Met Ala Leu Ala Tyr Val Met Leu Trp Thr Ile Trp Lys Ile Arg
                565                 570                 575

Asn Gly Ala Val Phe Asn Asn Arg Lys Ala Arg Ala Met Asn Thr Thr
                580                 585                 590

Asp Glu Lys Ser Ile Ser Tyr Arg Pro Thr Ser Pro Ala Ala Ala Pro
                595                 600                 605

Ser Pro Ser Pro Ala Pro Ser Pro Ala Thr Ala Pro Ser Pro Pro Ala
                610                 615                 620

Thr Ser Ser Pro Glu Pro Ala Thr His Ser Pro Met Leu Ile Gly Thr
625                 630                 635                 640

Glu Glu Met Phe Glu Gly Leu Val Arg Gln Leu Ile Leu Gly Tyr Leu
                645                 650                 655

Gly Gln Tyr Ile Lys Asp Ile His Arg Glu Gln Leu Lys Ile Thr Leu
                660                 665                 670

Trp Asn Glu Glu Val Phe Leu Glu Asn Val Glu Leu Ile Leu Glu Ala
                675                 680                 685

Phe Asp Tyr Leu Glu Leu Pro Phe Ala Leu Lys Gln Gly Arg Val Gly
                690                 695                 700

Arg Leu Ser Ile Arg Ile Pro Trp Lys Lys Leu Gly Trp Asp Pro Ile
705                 710                 715                 720
```

```
Ile Ile Ile Leu Glu Asp Ile Leu Val Cys Ala Ser Gln Arg Glu Asp
            725                 730                 735

Glu Glu Trp Ser Val Asp Val Glu Arg Arg Glu Phe Ser Gly Lys
        740                 745                 750

Lys Ala Lys Leu Ala Ala Ala Glu Leu Ala Lys Leu Ser Gln Arg Val
        755                 760                 765

Cys Asp Asn Gln Thr Gly Lys Ser Phe Met Ser Tyr Ile Thr Ala Lys
770                 775                 780

Ile Ile Asp Gly Ile Gln Val Thr Ile Arg Asn Val His Ile Val Tyr
785                 790                 795                 800

Arg Asp Ile Ser Asn Glu Lys Ser Gln Thr Val Phe Gly Val Lys Leu
            805                 810                 815

Ala Ser Leu Thr Ala Met Lys Gln Asn Tyr Ala Gly Val Leu Ser Gly
            820                 825                 830

Lys Val Arg Val Gly Gln Val Asn Lys Ile Val Glu Ile Gln Gly Leu
            835                 840                 845

Glu Ile Tyr Cys Lys Thr Phe His Gly Ser Ser Thr Asp Ile His Thr
            850                 855                 860

Glu Asn Gly Glu Asp Ser Met Ala Met Val Ala Ala Ser Tyr Asp Asn
865                 870                 875                 880

Asp Glu His Ala His Leu Leu Ala Pro Val Asn Val Ser Ala Ser Leu
                885                 890                 895

Ser Val Asn Arg Ser Gly Arg Leu Glu Asn Asn Ala Ala Gln Tyr Ser
            900                 905                 910

Val Asp Ile Glu Leu Ser Gly Leu Val Leu Ser Leu Asp Glu Asp Gln
            915                 920                 925

Leu Gln Gln Ile Leu Tyr Leu Tyr Glu Tyr Leu Cys Thr Cys Arg Leu
        930                 935                 940

Arg Glu Lys Tyr Gly Arg Tyr Arg Pro Trp Gly Lys Pro Ile Ser Glu
945                 950                 955                 960

Arg Gln Leu Gly Trp Gln Ile Gln Trp Trp His Tyr Ala Gln His Ser
                965                 970                 975

Val Leu Ser Asp Val Arg Lys Arg Leu Lys Thr Ser Trp Lys Tyr
            980                 985                 990

Leu Gly Glu Arg Leu Gly Arg Lys Arg Arg Tyr Val Asn Leu Tyr Lys
        995                 1000                1005

Leu Lys Leu Glu Cys Leu Arg Lys Glu Gln Pro Leu Asp Asp Glu
    1010                1015                1020

Ile Val Met Glu Leu Asp Gln Met Glu Lys Val Ser Asp Ile Glu
    1025                1030                1035

Asp Ile Leu Ser Tyr Arg Ser Ala Ala Glu Asn Glu Leu Gln Glu
    1040                1045                1050

Phe Leu Val Asp Ser Pro Ser Gly Ile Gly Gly Ser Glu Val Asn
    1055                1060                1065

Thr Thr Ile Asp Lys Ser Met Asp Asp Gln Thr Ser Gly Lys
    1070                1075                1080

Pro Gln Gly Trp Leu Lys Trp Leu Ser Arg Gly Met Leu Gly Ala
    1085                1090                1095

Gly Gly Thr Asp Asp Ser Ser Gln Phe Ser Gly Val Val Ser Asp
    1100                1105                1110

Glu Val Ile Lys Asp Ile Tyr Glu Ala Thr Lys Phe His Pro Ala
    1115                1120                1125
```

```
Pro Ser Pro Val Leu Asp Ala Ser Gly Thr Asp Arg Val Leu Leu
    1130            1135            1140

Thr Ser Ile Lys Cys Ser Ile His Gln Ile Ser Ala Thr Leu Arg
    1145            1150            1155

Asn Lys Lys Leu Asp Arg Ala Ile Gly Glu Val Val Phe Glu Gly
    1160            1165            1170

Asn Val Val Glu Cys Met Ile Trp Glu Ser Ala Val Val Thr
    1175            1180            1185

Ala Ser Ile Asn Ser Val Glu Met Ile Asn Pro Leu Asn Asn Gln
    1190            1195            1200

Ala Ile Leu Leu Ile Lys Arg Val Ile Ser Glu Glu Ser Phe Leu
    1205            1210            1215

Glu Glu Glu Lys Pro Ser Leu Asn Ile Gln Ala Tyr Ile Pro Gln
    1220            1225            1230

Ala Asn Arg Glu Gly Asp Leu Thr Leu Lys Val Leu Leu Glu Pro
    1235            1240            1245

Ile Glu Val Thr Cys Asp Pro Thr Tyr Leu Val Asn Phe Met Glu
    1250            1255            1260

Leu Tyr Thr Val Leu Gly Ser Tyr Thr Ser His Glu Glu Arg Val
    1265            1270            1275

Leu Asn Ser Leu Asn Gly Ile Asn Asp Val Lys Ser Arg Leu Ile
    1280            1285            1290

Ser Lys Ala Lys Tyr Ile Leu Ser Gly Arg Lys Arg Met Met Trp
    1295            1300            1305

Asp Ile Ser Leu Ile Asn Ile Lys Ile Asn Ile Pro Trp Glu Asn
    1310            1315            1320

Gly Asn Ser Glu Met His Lys Leu Val Leu Glu Leu Thr Ala Val
    1325            1330            1335

Thr Phe Ala Ser Lys Arg Asp Ile Gly Ser Phe Ala Pro Asp Ile
    1340            1345            1350

Asn Val Pro Ser Gln Phe Met Arg Asn Leu Ile Asp Asp Asn Ser
    1355            1360            1365

Ser Asn Glu Leu Leu Glu Gly Thr His Ile Gln Asp Leu Tyr Asp
    1370            1375            1380

Leu Leu Glu Ile Lys Ile Ile Asp Phe Gln Asp Glu Ser Leu Leu
    1385            1390            1395

Lys Ala Leu Glu Val Tyr Val Leu Val Ala Thr Leu Leu Ala His
    1400            1405            1410

Val Ser Pro Ser Ile Ile Gly Ser Phe Leu Glu Leu Val Glu Ser
    1415            1420            1425

Met Asn Met Leu His His Thr Ser Gln Leu Gly Ala Thr Ser Ala
    1430            1435            1440

Thr Ser Ser Ile Glu Pro Arg Asn Ser Ser Ser Ile Ser Val Ile
    1445            1450            1455

Ala Asn Leu Glu Ser Ala Ser Ile Ile Val Asp Leu Glu Asn Gly
    1460            1465            1470

Leu Glu Ala Ser Cys Thr Leu Thr Val Ser Leu Gln Asp Leu Asp
    1475            1480            1485

Met Arg Met Gly Ser Met Lys Ser Thr Gln Ser Phe Trp Ile Cys
    1490            1495            1500

Thr Arg Asp Leu Lys Val Thr Ser Arg Leu Leu Glu Ser Gly Asp
    1505            1510            1515

Asp Leu Asp Leu Ile Ile Cys Leu Pro Gln Ser Thr Ser Pro Asn
```

```
            1520                1525                1530

Asp Gly Cys Leu Val Leu His Tyr Asp Gly Asn Leu Ser Ile Cys
            1535                1540                1545

Leu Ser Asp Leu Asp Leu His Cys Tyr Pro His Ile Val Gly Leu
            1550                1555                1560

Leu Val Glu Phe Ser Gly Lys Leu Ser Thr Tyr Ser Pro Ser Asn
            1565                1570                1575

Ala Lys Asn Gln Asp Phe Val Asp Ser Asn Ser Asn Thr Ile Leu
            1580                1585                1590

Ser Asp Ser Tyr Ile Asp Phe Gln Arg Phe Gly Cys Ser Lys Ile
            1595                1600                1605

Ser Val Asn His Tyr Pro Phe Val Thr Ile Tyr Asn Asp Arg Ser
            1610                1615                1620

Leu Leu Asn Leu Asp Thr Ser Leu Ile Asn Ile Lys Lys Val His
            1625                1630                1635

Lys Thr Asn Ser Ser Lys Leu Arg Ala Lys Lys Asp Asn His Gln
            1640                1645                1650

Val Gly Ala Leu Val Val Met Asn Leu Asp Leu Asn Ser Ile Arg
            1655                1660                1665

Leu His Leu His Asp Ser Ser Ser Ile Val Ala Ser Val Thr Leu
            1670                1675                1680

Pro Val Ser Lys Ser Ser Phe Ala Ile His Glu Asn Phe Leu Asp
            1685                1690                1695

Val Leu Phe Ser Thr Glu Gly Leu Ser Leu Ser Ser Gln Trp Tyr
            1700                1705                1710

Pro Gln Thr Leu Gln Asp Ser Leu Trp Gly Pro Ala Ser Leu Asn
            1715                1720                1725

Leu Ser Pro Val Ile Asn Ile Arg Val Arg Lys Gly Asn His Gly
            1730                1735                1740

Ile Glu Leu Asp Phe Ser Val Gln Asn Val Ser Cys Ile Leu Pro
            1745                1750                1755

Thr Glu Phe Leu Ala Ala Leu Ile Gly Tyr Phe Ser Leu Pro Asp
            1760                1765                1770

Trp Ser Tyr Ser Asn Pro Asn Glu Ser Ser Pro Thr Thr Thr Asn
            1775                1780                1785

Thr Asn Thr Asn Asn Asn Ser Ile Ser Phe Thr Tyr Lys Phe Glu
            1790                1795                1800

Ile Leu Asp Ser Val Leu Phe Thr Pro Val Ala Asn Pro Asp His
            1805                1810                1815

Glu Phe Ile Lys Leu Asn Ile Pro Gln Met Tyr Cys Thr Phe Ile
            1820                1825                1830

Asp Ser Ile Asp Ser Asp Thr Leu Leu Lys Glu Ile Pro Leu Glu
            1835                1840                1845

Cys Ser Val Pro Val Gly Phe Thr Gly Asn Gln Asn Tyr Cys Leu
            1850                1855                1860

Asn Val Phe Gly Arg Asp Leu Ser Leu His His Ile Ile Cys Arg
            1865                1870                1875

Lys Asp Asn Ala Ser Glu Val Thr Ser Val Ser Leu Ile Ala Pro
            1880                1885                1890

Phe Ser Gly Asp Ile Trp Ile Thr Ile Pro Tyr Glu Ser Asn Ser
            1895                1900                1905

Ser Tyr Ala Thr Cys Ile Met Ser Arg Val Ser Lys Cys Gln Phe
            1910                1915                1920
```

-continued

```
Thr Val Glu Gly Arg Glu Ile Leu Gly Cys Ile Gly Ala Leu Gln
    1925            1930            1935

Asp Val Val Asp Gln Phe Ser Ser Val Gly Asn Leu Ser Thr Cys
    1940            1945            1950

Phe Thr Ser Asp Val Ser Glu Phe Leu Asn Leu Lys Glu Asn Tyr
    1955            1960            1965

Val Val Pro Val Pro Ile Glu Ser Ser Thr Val Ser Phe Thr Glu
    1970            1975            1980

Ile Arg Cys Ser Val Gln Ser Met Ser Val Glu Leu Tyr Ser Asp
    1985            1990            1995

Lys Met Asn Gly Asn Arg Leu Ile Ala Lys Ser Asp Met Lys Phe
    2000            2005            2010

Ala Cys Gly Ile Ser Met Lys Thr Asp Lys Pro Leu Ser Leu Asp
    2015            2020            2025

Ile Ser Phe Thr Cys Phe Thr Leu Ser Ser Leu Thr Ser Val
    2030            2035            2040

Val Leu Leu Glu Cys Thr Ser Cys Thr Lys Asn Val Pro Val Leu
    2045            2050            2055

Asn Met Gln Phe Leu Met Ser Asp Asp Gly Lys Asn His Leu Arg
    2060            2065            2070

Phe Ser Leu Pro Cys Val Asn Ile Trp Leu Phe Leu Ser Glu Trp
    2075            2080            2085

Ser Gln Val Val Asp Leu Val Asn Ser Cys Cys Glu Pro Ala Ile
    2090            2095            2100

Gln Asn Glu Glu Pro Glu Lys Ser Thr Ser Ala Pro Val Ser Arg
    2105            2110            2115

Val Asp Thr Ala Glu Asn Ser Pro Gln Ser Thr Thr Val Ser Ser
    2120            2125            2130

Tyr Pro Ser Leu Glu Asp Arg Phe Ser Leu Thr Val Lys Ser Asp
    2135            2140            2145

Leu Ile Gly Val Lys Ile Arg Ile Pro Val Gln Val Ser Gly Glu
    2150            2155            2160

Val Val Lys Tyr Phe Gly Ala Pro Gln Val Arg Glu Gln Ser Leu
    2165            2170            2175

Val Thr Gly Arg Asp His Gly Ser Phe Leu Phe Ile Tyr Leu Gln
    2180            2185            2190

Ser Arg Cys Thr Glu Val Asn Met Lys Gly Glu Thr Val Asn Leu
    2195            2200            2205

Lys Ser Asn Leu Gly Lys Ala Met Gly Thr Val Glu Leu Phe Gln
    2210            2215            2220

Asn Lys Ser Val His Ser Trp Pro Leu Phe Gln Leu Leu Glu Ile
    2225            2230            2235

Asp Ile Glu Ala Glu Ser Gly Asn Asp Asp Met Asp Arg Met His
    2240            2245            2250

Leu Lys Thr Glu Ile His Cys Asp Asn Leu Asp Val Trp Leu Ser
    2255            2260            2265

His His Ala Phe Tyr Phe Trp Gln Thr Met Leu Phe Met Phe Pro
    2270            2275            2280

Glu Gly Ser Gly Ser Glu Ser Pro Gln Leu Pro Val Gly Ser Val
    2285            2290            2295

Asn Phe Arg Phe His Leu Arg Lys Leu Ser Ile Leu Leu Thr Asp
    2300            2305            2310
```

```
Glu Lys Trp Ser Ser Asn Gly Pro Leu Leu Glu Ile Leu Met Gly
    2315                2320                2325

Ser Leu Leu Phe His Gly Ile Ile Thr Ala Asn Met Met Glu Gly
    2330                2335                2340

Ser Ile Asp Ser Asp Leu Gln Val Asn Tyr Asn Asn Ile His Lys
    2345                2350                2355

Val Leu Trp Glu Pro Phe Leu Glu Pro Trp Lys Phe Gln Ile Thr
    2360                2365                2370

Leu Arg Arg Gln Gln Gly Lys Ser Thr Leu Glu Asn Ser Pro Val
    2375                2380                2385

Met Thr Asp Ile Arg Leu Glu Ser Ser Thr Asn Leu Asn Ile Asn
    2390                2395                2400

Val Thr Glu Ser Phe Ile Glu Val Ala Phe Arg Thr Phe Asp Met
    2405                2410                2415

Ile Lys Asp Ala Ser Asp Leu Ile Ser Leu Asn Ile Leu Pro Glu
    2420                2425                2430

Asn Asn Ser Arg Leu Thr Lys Pro His Thr Asn Glu Asn Thr Leu
    2435                2440                2445

Ala Asn Arg Tyr Ala Pro Tyr Thr Leu Glu Asn Leu Thr Ser Leu
    2450                2455                2460

Pro Leu Val Phe Tyr Ile Ser Lys Gly Glu Gly Phe Asn Met Thr
    2465                2470                2475

Ser Leu Lys Asp Gly Lys His Val Gln Pro Gly Cys Ser Tyr Pro
    2480                2485                2490

Val Asn Ile Asp Asn Asn Pro Glu Glu Gln Thr Phe Gly Phe Arg
    2495                2500                2505

Pro Ser His Ser Thr Asp Asn Leu Gly Gly Asp Met Gln Phe Ala
    2510                2515                2520

Asp Ala Gln His His Tyr Ile Val Val Gln Leu Glu Gly Thr Ser
    2525                2530                2535

Thr Leu Ser Ala Pro Val Ser Ile Asp Leu Val Gly Val Ser Phe
    2540                2545                2550

Phe Glu Val Asp Phe Ser Thr Asn Ile Gly Leu Asp Val Ser Lys
    2555                2560                2565

Gly Gly Tyr Val Val Pro Val Ile Asp Val Ser Val Gln Arg
    2570                2575                2580

Tyr Thr Lys Leu Val Arg Leu Tyr Ser Thr Val Ile Leu Thr Asn
    2585                2590                2595

Ala Thr Ser Met Pro Phe Glu Val Arg Phe Asp Ile Pro Phe Gly
    2600                2605                2610

Val Ser Pro Lys Ile Leu Asp Pro Val Tyr Pro Gly His Glu Phe
    2615                2620                2625

Pro Leu Pro Leu His Leu Ala Glu Ser Gly Arg Ile Arg Trp Arg
    2630                2635                2640

Pro Leu Gly Ser Thr Tyr Leu Trp Ser Glu Ala Tyr Ser Ile Ser
    2645                2650                2655

Asn Ile Leu Ser Asn Glu Ser Lys Ile Gly His Leu Arg Ser Phe
    2660                2665                2670

Val Cys Tyr Pro Ser Leu Pro Ser Ser Asp Pro Phe Arg Cys Cys
    2675                2680                2685

Val Ser Val His Asp Val Cys Leu Pro Ser Ala Gly Arg Val Ile
    2690                2695                2700

Asn Lys Arg Gly Ser Ser Ser Ser Leu Tyr Asn Ile Asn Thr His
```

```
              2705                2710                2715
Asp His Gly Asp Lys Ile Glu Asn Gln Asp Leu Ser Asn Lys Arg
    2720                2725                2730
Cys Ile His Leu Ile Thr Leu Ser Asn Pro Leu Ile Val Lys Asn
    2735                2740                2745
Tyr Leu Pro Val Glu Val Ser Val Val Ile Glu Ser Gly Gly Val
    2750                2755                2760
Ser Arg Ser Met Leu Leu Ser Glu Val Glu Thr Phe Phe Tyr His
    2765                2770                2775
Ile Asp Ser Ser His Asp Leu Ser Leu Thr Phe Glu Ile His Gly
    2780                2785                2790
Phe Arg Pro Ser Leu Leu Lys Phe Pro Arg Ala Glu Lys Phe Ser
    2795                2800                2805
Gly Ile Ala Lys Phe Ser Gly Thr Lys Phe Ser Ser Ser Glu Ser
    2810                2815                2820
Ile Asn Phe Ala Ala Asp Asn Ser Lys Gly Pro Leu Tyr Val Thr
    2825                2830                2835
Met Glu Lys Val Met Asp Ala Phe Ser Gly Ala Arg Glu Ile Cys
    2840                2845                2850
Ile Phe Val Pro Phe Leu Leu Tyr Asn Cys Cys Gly Phe Pro Leu
    2855                2860                2865
Thr Ile Ala Asn Ser Thr Asn Asp Leu Thr Met Arg Asp Thr Leu
    2870                2875                2880
Pro Ser Cys Tyr Asp Leu Asp Glu Glu Asp Pro Phe Leu Gly Lys
    2885                2890                2895
Lys Asp Gly Leu Ser Leu Leu Phe Ser Asn Gln Val Ser Asn Asn
    2900                2905                2910
Asp Pro Met Ser Asn Leu Val Ser Thr Arg Lys Glu Ser Phe Thr
    2915                2920                2925
Ser Ser Gly Ser Thr Lys Lys Asn Ile Gly Thr Gln Lys Pro Ser
    2930                2935                2940
Leu His Asp Gln Glu Lys Ser Gln Leu Ser His Ser Gln Gln Leu
    2945                2950                2955
Asp Phe Asp Glu Thr Thr Arg Lys Lys Val Asn Phe Arg Met Tyr
    2960                2965                2970
Ser Pro Asp Pro Asn Ile Ala Ser Ser Glu Ile Met Val Arg Val
    2975                2980                2985
Ser Arg Cys Arg Ser Asp Ala Asp Met Ala Ser Thr Ser Asp Tyr
    2990                2995                3000
Thr Trp Ser Ser Gln Phe Phe Leu Val Pro Pro Ala Gly Ser Thr
    3005                3010                3015
Thr Val Leu Val Pro Arg Ser Ser Thr Asn Ala Ser Tyr Val Leu
    3020                3025                3030
Ser Val Ala Ser Ser Ala Ile Ser Gly Pro Tyr Ser Gly Arg Thr
    3035                3040                3045
Arg Ile Ile Asn Phe Gln Pro Arg Tyr Val Ile Ser Asn Ala Cys
    3050                3055                3060
Ser Gln Asp Leu Cys Tyr Arg Gln Lys Gly Ser Asp Phe Ile Tyr
    3065                3070                3075
His Leu Lys Ala Gly Gln His Ser His Ile His Trp Thr Asp Ile
    3080                3085                3090
Thr Arg Glu Leu Leu Val Ser Val Arg Phe Asp Glu Pro Gly Trp
    3095                3100                3105
```

```
Gln Trp Ser Gly Cys Phe Phe Pro Glu His Leu Gly Asp Thr Gln
3110                3115                3120

Leu Lys Met Arg Asn Tyr Val Ser Gly Ala Val Ser Met Val Arg
3125                3130                3135

Val Glu Val Gln Asn Ala Asp Asp Ala Ile Arg Asp Asp Lys Ile
3140                3145                3150

Val Gly Asn Pro His Gly Glu Ser Gly Thr Asn Leu Ile Leu Leu
3155                3160                3165

Ser Asp Asp Asp Thr Gly Phe Met Pro Tyr Arg Val Asp Asn Phe
3170                3175                3180

Ser Lys Glu Arg Leu Arg Ile Tyr Gln Gln Lys Cys Glu Ala Phe
3185                3190                3195

Glu Thr Val Ile His Ser Tyr Thr Ser Cys Pro Tyr Ala Trp Asp
3200                3205                3210

Glu Pro Ser Tyr Pro His Arg Leu Thr Val Glu Val Phe Ala Glu
3215                3220                3225

Arg Val Val Gly Ser Tyr Thr Leu Asp Asp Ala Lys Glu Tyr Lys
3230                3235                3240

Pro Val Val Leu Pro Ser Thr Ser Glu Lys Pro Glu Arg Arg Leu
3245                3250                3255

Leu Ile Ser Val His Ala Glu Gly Ala Leu Lys Val Leu Ser Ile
3260                3265                3270

Ile Asp Ser Ser Tyr His Ile Phe Asp Asp Val Lys Ile Pro Arg
3275                3280                3285

Ser Pro Arg Leu Thr Glu Lys Arg Glu Tyr Asp Gln Lys Gln Glu
3290                3295                3300

Ser Ser Leu Leu Tyr Gln Glu Arg Val Ser Ile Ser Ile Pro Phe
3305                3310                3315

Ile Gly Ile Ser Val Met Ser Ser Gln Pro Gln Glu Leu Leu Phe
3320                3325                3330

Ala Cys Ala Arg Asn Thr Met Ile Asp Leu Val Gln Ser Leu Asp
3335                3340                3345

Gln Gln Asn Leu Ser Leu Lys Ile Ser Ser Leu Gln Ile Asp Asn
3350                3355                3360

Gln Leu Pro Thr Thr Pro Tyr Pro Val Ile Leu Ser Phe Asp His
3365                3370                3375

Glu Tyr Lys Gln Leu Pro Thr Ser Gln Ile Lys Asn Lys Asp Glu
3380                3385                3390

Pro Val Phe Ser Leu Ala Ala Ala Lys Trp Arg Asn Lys Asp Arg
3395                3400                3405

Ala Leu Leu Ser Phe Glu His Ile Asn Leu Arg Met Ala Asp Phe
3410                3415                3420

His Leu Glu Leu Glu Gln Asp Val Ile Leu Ser Leu Phe Asp Phe
3425                3430                3435

Ser Lys Ala Val Ser Ser Arg Phe His Ser Arg Gly Met Pro His
3440                3445                3450

Met Asp Ser Val Val His Pro Leu Ser Ser Asn Leu Ser Gly Asn
3455                3460                3465

Lys Ala Thr Lys Leu Ala Glu Lys Thr Glu Ile Glu Gly Glu Ser
3470                3475                3480

Phe Pro Leu Leu Pro Ser Ile Val Pro Ile Gly Ala Pro Trp Gln
3485                3490                3495
```

-continued

```
Lys Ile Tyr Leu Leu Ala Arg Lys Gln Lys Lys Ile Tyr Val Glu
    3500                3505                3510
Leu Leu Glu Val Ala Pro Ile Thr Leu Thr Leu Ser Phe Ser Ser
    3515                3520                3525
Ser Pro Trp Met Leu Arg Asn Gly Ile Leu Thr Ser Gly Glu Tyr
    3530                3535                3540
Leu Ile His Arg Gly Leu Met Ala Leu Ala Asp Val Glu Gly Ala
    3545                3550                3555
Arg Ile His Leu Arg Arg Leu Thr Ile Ser His Gln Leu Ala Ser
    3560                3565                3570
Leu Glu Ser Ile Arg Glu Ile Leu Ile Ile His Tyr Thr Arg Gln
    3575                3580                3585
Leu Leu His Glu Met Tyr Lys Val Phe Gly Ser Ala Gly Val Ile
    3590                3595                3600
Gly Asn Pro Met Gly Phe Ala Arg Ser Val Gly Leu Gly Ile Arg
    3605                3610                3615
Asp Phe Leu Ser Val Pro Ala Arg Ser Phe Met Gln Ser Pro Ala
    3620                3625                3630
Gly Leu Ile Thr Gly Met Ala Gln Gly Thr Thr Ser Leu Leu Ser
    3635                3640                3645
Asn Thr Val Tyr Ala Ile Ser Asp Ala Ala Thr Gln Gly Ile Val
    3650                3655                3660
Ala Phe Thr Met Asp Asp Pro Pro Ser Ala Ala Glu Met Gly Lys
    3665                3670                3675
Gly Val Ile Asn Glu Val Leu Glu Gly Leu Thr Gly Leu Leu Gln
    3680                3685                3690
Ser Pro Ile Arg Gly Ala Glu Lys His Gly Leu Pro Gly Val Leu
    3695                3700                3705
Ser Gly Ile Ala Leu Gly Val Thr Gly Leu Val Ala Arg Pro Ala
    3710                3715                3720
Ala Ser Ile Leu Glu Val Thr Glu Lys Thr Ala Arg Ser Ile Arg
    3725                3730                3735
Asn Arg Ser Lys Leu Tyr His Ile Arg Leu Arg Val Arg Leu Pro
    3740                3745                3750
Arg Pro Leu Thr Pro Asn His His Pro Leu Lys Pro Tyr Ser Trp
    3755                3760                3765
Asp Gln Ala Val Gly Leu Ser Val Leu Thr Asn Thr Asn Ser Asn
    3770                3775                3780
Ser Asp Ser Asp Leu Lys Asp Glu Thr Leu Val Leu Ser Lys Ser
    3785                3790                3795
Leu Lys Gln Lys Gly Lys Phe Val Ile Ile Thr Gln Arg Leu Leu
    3800                3805                3810
Leu Ile Val Thr Ser Ser Ser Leu Thr Asn Leu Gly Gln Pro Asn
    3815                3820                3825
Phe Lys Gly Val Pro Ala Asp Pro Asp Trp Val Val Glu Ala Glu
    3830                3835                3840
Ile Thr Leu Asp Ser Val Ile His Val Asp Val Asp Gly Glu Val
    3845                3850                3855
Val His Ile Val Gly Ser Ser Ser Asp Val Val Arg Gln Asn
    3860                3865                3870
Val Gly Gly Lys Gln Arg Trp Tyr Asn Pro Leu Pro Leu Phe Gln
    3875                3880                3885
Thr Asn Leu Glu Cys Leu Gly Lys Glu Glu Ala Gly Glu Leu Leu
```

```
                    3890                3895                3900

Lys Val Leu Leu Val Thr Ile Glu Arg Gly Lys Glu Arg Gly Trp
        3905                3910                3915

Gly Arg Gly Cys Val Tyr Arg Leu His Gln Ser Asn Val Arg
        3920                3925                3930

<210> SEQ ID NO 4
<211> LENGTH: 909
<212> TYPE: DNA
<213> ORGANISM: Taraxacum officinale

<400> SEQUENCE: 4
gaaaccgaag caaactctac cacatccgcc tccgggtccg cctcccgaga ccgctaaccc     60
ccaaccacca cccgttaaaa ccctactcgt gggaccaagc agtcggcctc tccgtcctca    120
ccaataccaa ttccaattcc gattccgacc tcaaagacga aaccctcgtc ctctccaaat    180
ccctcaaaca aaagggcaaa ttcgtcatta tcacccaacg gttactcctc attgttacct    240
cctcgagcct aacgaattta ggtcaaccca atttcaaagg cgtccctgcg gaccccgatt    300
gggtggttga agccgagata acgttggata gtgtgataca cgtggatgtt gatggagagg    360
tggtgcatat tgtcgggagt agttctgatg tggtggttag acagaatgtt ggtgggaagc    420
agcggtggta taatccgttg ccgctgtttc agacgaattt ggagtgttta gggaaggagg    480
aggcggggga gttgttgaag gtgttgttgg tgacgattga gagagggaag gagagagggt    540
ggggccgggg gtgtgtgtac cgtctgcatc agagtaatgt taggtgatgt atatttttt    600 tctacatata aagttactat aggagaaaaa ggactggata ttatattata catacctgaa    660
acaaggaaac gttttctttc aaaattttgg ctgtattatt attttgtcga ccatgttggg    720
ctaaaatggc caattattta cttatgacat ggttaaaaaa tattggtgtc ttgttttgta    780
taattacaat ttatattagt atcgatgcaa tgtaagattg tagaaagcgc taccgtataa    840
aacaacataa gtcatgaggt tacaccctag tggggtcaag ggaacaaaaa cattttaaac    900
gtttttcag                                                            909

<210> SEQ ID NO 5
<211> LENGTH: 909
<212> TYPE: RNA
<213> ORGANISM: Taraxacum officinale

<400> SEQUENCE: 5
gaaaccgaag caaacucuac cacauccgcc uccggguccg ccucccgaga ccgcuaaccc     60
ccaaccacca cccguuaaaa cccuacucgu gggaccaagc agucggccuc uccguccuca    120
ccaauaccaa uuccaauucc gauuccgacc ucaaagacga aaccucguc cucuccaaau    180 cccucaaaca aaagggcaaa uucgucauua ucacccaacg guuacuccuc auuguuaccu    240
ccucgagccu aacgaauuua ggucaaccca auucaaagg cguccccugcg gaccccgauu    300 gggugguuga agccgagaua acguuggaua gugugauaca cguggauguu gauggagagg    360
uggugcauau ugucgggagu aguucugaug uggugguuag acagaauguu gguggggaagc    420 agcgguggua uaauccguug ccgcuguuuc agacgaauuu ggagugguuua gggaaggagg    480 aggcggggga guuguugaag guguuguugg ugacgauuga gagagggaag gagagagggu    540
ggggccgggg gugugugugac cgucugcauc agaguaaugu uaggugauguu auauuuuuu    600 ucuacauaua aaguuacuau aggagaaaaa ggacuggaua uuauauuaua cauaccugaa    660
acaaggaaac guuuucuuuc aaaauuuugg cuguauuauu auuugucga ccauguuggg    720
```

```
cuaaaauggc caauuauuua cuuaugacau gguuaaaaaa uauuggguguc uuguuuugua    780 uaauuacaau uuauauuagu aucgaugcaa uguaagauuu uagaaagcgc uaccguauaa    840
aacaacauaa gucaugaggu uacacccuag ugggucaag ggaacaaaaa cauuuuaaac    900
guuuuucag                                                            909
```

<210> SEQ ID NO 6
<211> LENGTH: 582
<212> TYPE: DNA
<213> ORGANISM: Taraxacum officinale

<400> SEQUENCE: 6

```
aaccgaagca aactctacca catccgcctc cgggtccgcc tcccgagacc gctaaccccc     60
aaccaccacc cgttaaaacc ctactcgtgg gaccaagcag tcggcctctc cgtcctcacc    120
aataccaatt ccaattccga ttccgacctc aaagacgaaa ccctcgtcct ctccaaatcc    180
ctcaaacaaa agggcaaatt cgtcattatc acccaacggt tactcctcat tgttacctcc    240
tcgagcctaa cgaatttagg tcaacccaat ttcaaggcg tccctgcgga ccccgattgg    300
gtggttgaag ccgagataac gttggatagt gtgatacacg tggatgttga tggagaggtg    360
gtgcatattg tcgggagtag ttctgatgtg gtggttagac agaatgttgg tgggaagcag    420
cggtggtata atccgttgcc gctgtttcag acgaatttgg agtgtttagg gaaggaggag    480 gcggggggagt tgttgaaggt gttgttggtg acgattgaga gagggaagga gagagggtgg    540
ggccgggggt gtgtgtaccg tctgcatcag agtaatgtta gg                       582
```

<210> SEQ ID NO 7
<211> LENGTH: 194
<212> TYPE: PRT
<213> ORGANISM: Taraxacum officinale

<400> SEQUENCE: 7

```
Asn Arg Ser Lys Leu Tyr His Ile Arg Leu Arg Val Arg Leu Pro Arg
1               5                   10                  15

Pro Leu Thr Pro Asn His His Pro Leu Lys Pro Tyr Ser Trp Asp Gln
            20                  25                  30

Ala Val Gly Leu Ser Val Leu Thr Asn Thr Asn Ser Asn Ser Asp Ser
        35                  40                  45

Asp Leu Lys Asp Glu Thr Leu Val Ser Lys Ser Leu Lys Gln Lys
    50                  55                  60

Gly Lys Phe Val Ile Ile Thr Gln Arg Leu Leu Leu Ile Val Thr Ser
65                  70                  75                  80

Ser Ser Leu Thr Asn Leu Gly Gln Pro Asp Phe Lys Gly Val Pro Ala
                85                  90                  95

Asp Pro Asp Trp Val Val Glu Ala Glu Ile Thr Leu Asp Ser Val Ile
            100                 105                 110

His Val Asp Val Asp Gly Glu Val His Ile Val Gly Ser Ser Ser
        115                 120                 125

Asp Val Val Arg Gln Asn Val Gly Gly Lys Gln Arg Trp Tyr Asn
    130                 135                 140

Pro Leu Pro Leu Phe Gln Thr Asn Leu Glu Cys Leu Gly Lys Glu Glu
145                 150                 155                 160

Ala Gly Glu Leu Leu Lys Val Leu Leu Val Thr Ile Gln Arg Gly Lys
                165                 170                 175

Glu Arg Gly Trp Gly Arg Gly Cys Val Tyr Arg Leu His Gln Ser Asn
```

<210> SEQ ID NO 8
<211> LENGTH: 51
<212> TYPE: DNA
<213> ORGANISM: Taraxacum officinale

<400> SEQUENCE: 8

```
gaattcctct atgttttgga accttcttgt tgttattccg caccacttta a            51
```

<210> SEQ ID NO 9
<211> LENGTH: 479
<212> TYPE: DNA
<213> ORGANISM: Taraxacum officinale

<400> SEQUENCE: 9

```
aattccaatt ccgattccga cctcaaagac gaaaccctcg tcctctccaa atccctcaaa    60
caaaagggca aattcgtcat tatcacccaa cggttactcc tcattgttac ctcctcgagc   120
ctaacgaatt taggtcaacc cgatttcaaa ggcgtccctg cggaccccga ttgggtggtt   180
gaagccgaga taacgttgga tagtgtgata cacgtggatg ttgatggaga ggtggtgcat   240
attgtcggga gtagttctga tgtggtggtt agacagaatg ttggtggtgg tggtgggtgg   300
gggaagcagc ggtggtataa tccgccgacg ccgttgccgc tgtttcagac gaatttggag   360
tgtttaggga aggaggaggc gggggagttg ttgaaggtgt tgttggtgac gattcagaga   420
gggaaggaga gagggtgggg ccgggggtgt gtgtaccgtc tgcatcagag taatgttag    479
```

<210> SEQ ID NO 10
<211> LENGTH: 159
<212> TYPE: PRT
<213> ORGANISM: Taraxacum officinale

<400> SEQUENCE: 10

```
Asn Ser Asn Ser Asp Ser Asp Leu Lys Asp Glu Thr Leu Val Leu Ser
1               5                   10                  15
Lys Ser Leu Lys Gln Lys Gly Lys Phe Val Ile Ile Thr Gln Arg Leu
            20                  25                  30
Leu Leu Ile Val Thr Ser Ser Ser Leu Thr Asn Leu Gly Gln Pro Asp
        35                  40                  45
Phe Lys Gly Val Pro Ala Asp Pro Asp Trp Val Val Glu Ala Glu Ile
    50                  55                  60
Thr Leu Asp Ser Val Ile His Val Asp Val Asp Gly Glu Val Val His
65                  70                  75                  80
Ile Val Gly Ser Ser Ser Asp Val Val Arg Gln Asn Val Gly Gly
                85                  90                  95
Gly Gly Gly Trp Gly Lys Gln Arg Trp Tyr Asn Pro Pro Thr Pro Leu
            100                 105                 110
Pro Leu Phe Gln Thr Asn Leu Glu Cys Leu Gly Lys Glu Glu Ala Gly
        115                 120                 125
Glu Leu Leu Lys Val Leu Leu Val Thr Ile Gln Arg Gly Lys Glu Arg
    130                 135                 140
Gly Trp Gly Arg Gly Cys Val Tyr Arg Leu His Gln Ser Asn Val
145                 150                 155
```

<210> SEQ ID NO 11
<211> LENGTH: 455

```
<212> TYPE: DNA
<213> ORGANISM: Taraxacum officinale

<400> SEQUENCE: 11
aattccaatt ccgattccga cctcaaagac gaaaccctcg tcctctccaa atccctcaaa      60
caaaagggca aattcgtcat tatcacccaa cggttactcc tcattgttac ctcctcgagc    120
ctaacgaatt taggtcaacc caatttcaaa ggcgtccctg cggaccccga ttgggtggtt    180
gaagccgaga taacgttgga tagtgtgata cacgtggatg ttgatggaga ggtggtgcat    240
attgtcggga gtagttctga tgtggtggtt agacagaatg ttggtgggaa gcagcggtgg    300
tataatccgt tgccgctgtt tcagacgaat ttggagtgtt tagggaagga ggaggcgggg    360
gagttgttga aggtgttgtt ggtgacgatt gagagaggga aggagagagg gtggggccgg    420
gggtgtgtgt accgtctgca tcagagtaat gttag                               455

<210> SEQ ID NO 12
<211> LENGTH: 151
<212> TYPE: PRT
<213> ORGANISM: Taraxacum officinale

<400> SEQUENCE: 12

Asn Ser Asn Ser Asp Ser Asp Leu Lys Asp Glu Thr Leu Val Leu Ser
1               5                   10                  15

Lys Ser Leu Lys Gln Lys Gly Lys Phe Val Ile Ile Thr Gln Arg Leu
            20                  25                  30

Leu Leu Ile Val Thr Ser Ser Leu Thr Asn Leu Gly Gln Pro Asn
        35                  40                  45

Phe Lys Gly Val Pro Ala Asp Pro Asp Trp Val Val Glu Ala Glu Ile
    50                  55                  60

Thr Leu Asp Ser Val Ile His Val Asp Val Asp Gly Glu Val Val His
65                  70                  75                  80

Ile Val Gly Ser Ser Ser Asp Val Val Val Arg Gln Asn Val Gly Gly
                85                  90                  95

Lys Gln Arg Trp Tyr Asn Pro Leu Pro Leu Phe Gln Thr Asn Leu Glu
            100                 105                 110

Cys Leu Gly Lys Glu Glu Ala Gly Glu Leu Leu Lys Val Leu Leu Val
        115                 120                 125

Thr Ile Glu Arg Gly Lys Glu Arg Gly Trp Gly Arg Gly Cys Val Tyr
    130                 135                 140

Arg Leu His Gln Ser Asn Val
145                 150

<210> SEQ ID NO 13
<211> LENGTH: 938
<212> TYPE: DNA
<213> ORGANISM: Taraxacum officinale

<400> SEQUENCE: 13
gaaaccgaag caaactctac cacatccgcc tccgggtccg cctcccaaga ccgctaaccc      60
ccaaccaccc gttaaaaccc tactcgtggg accaagcagt cggcctctcc gtcctcacca    120
attccaattc cgattccgac ctcaaagacg aaaccctcgt cctctccaaa tccctcaaac    180
aaaagggcaa attcgtcatt atcacccaac ggttactcct cattgttacc tcctcgagcc    240
taacgaattt aggtcaaccc gatttcaaag gcgtccctgc ggaccccgat tgggtggttg    300
aagccgagat aacgttggat agtgtgatac acgtggatgt tgatggagag gtggtgcata    360
```

```
ttgtcgggag tagttctgat gtggtggtta gacagaatgt tggtggtggt ggtgggtggg    420
ggaagcagcg gtggtataat ccgccgacgc cgttgccgct gtttcagacg aatttggagt    480
gtttagggaa ggaggaggcg ggggagttgt tgaaggtgtt gttggtgacg attcagagag    540
ggaaggagag agggtggggc cggggtgtg tgtaccgtct gcatcagagt aatgttaggt     600
gatgtatatt tttttgtac atataaagtt tactatagga gaaaaggac tggatattat      660 attatacata cctgaaaaca aggaaacgtt ttctttcaaa attttggctg tattattatt    720
ttgtcgacca tgttgggcta aaatggccaa ttatttactt atgacatggt taaaaaatat    780
tggtgtcttg ttttgtataa ttacaattta tattcctttt tagactataa cttatgcaat   840
gtaagattgt gtataaaaca acataagtca tgaggttaca ccctagtggg atcaaggggg   900
ctacaccccg gaacaaaaac attttaaacg tttttcag                           938

<210> SEQ ID NO 14
<211> LENGTH: 5
<212> TYPE: PRT
<213> ORGANISM: Taraxacum officinale

<400> SEQUENCE: 14

Gly Gly Gly Gly Trp
1               5
```